US010334859B2

(12) United States Patent
Saelinger et al.

(10) Patent No.: US 10,334,859 B2
(45) Date of Patent: Jul. 2, 2019

(54) METHOD AND PESTICIDAL MIXTURES FOR CONTROLLING PENTATOMIDAE PESTS

(71) Applicant: BASF SE, Ludwigshafen (DE)

(72) Inventors: Daniel Saelinger, Ludwigshafen (DE); Joachim Dickhaut, Heidelberg (DE); Karsten Koerber, Eppelheim (DE); Wolfgang Von Deyn, Neustadt (DE); Raffael Koller, Zurich (CH); Arun Narine, Mannheim (DE); Jean-Yves Wach, Zurich (CH); Jochen Dietz, Karlsruhe (DE); Diana Londono, Apex, NC (US)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/519,278

(22) PCT Filed: Oct. 16, 2015

(86) PCT No.: PCT/EP2015/074067
§ 371 (c)(1),
(2) Date: Apr. 14, 2017

(87) PCT Pub. No.: WO2016/059240
PCT Pub. Date: Apr. 21, 2016

(65) Prior Publication Data
US 2017/0238554 A1 Aug. 24, 2017

Related U.S. Application Data

(60) Provisional application No. 62/064,493, filed on Oct. 16, 2014.

(51) Int. Cl.
A01N 43/90 (2006.01)
A01N 53/00 (2006.01)
A01N 43/22 (2006.01)
A01N 43/56 (2006.01)
A01N 47/20 (2006.01)
A01N 65/00 (2009.01)
A01N 37/24 (2006.01)
A01N 37/34 (2006.01)
A01N 37/50 (2006.01)
A01N 43/40 (2006.01)
A01N 43/54 (2006.01)
A01N 47/14 (2006.01)
A01N 47/18 (2006.01)
A01N 47/24 (2006.01)
A01N 47/38 (2006.01)
A01N 51/00 (2006.01)
A01N 63/04 (2006.01)
A01N 43/653 (2006.01)

(52) U.S. Cl.
CPC .............. A01N 65/00 (2013.01); A01N 43/22 (2013.01); A01N 43/56 (2013.01); A01N 43/90 (2013.01); A01N 47/20 (2013.01); Y02A 50/322 (2018.01); Y02A 50/352 (2018.01); Y02A 50/354 (2018.01)

(58) Field of Classification Search
CPC combination set(s) only.
See application file for complete search history.

(56) References Cited

U.S. PATENT DOCUMENTS

2003/0224936 A1* 12/2003 Kretzschmar
2012/0184589 A1* 7/2012 Gewehr
2014/0073592 A1 3/2014 Pszczolkowski et al.

FOREIGN PATENT DOCUMENTS

| CN | 1398524 A | 2/2003 |
| KR | 20130026742 A | 3/2013 |
| WO | WO2005025587 A1 | 3/2005 |
| WO | WO2015055752 A1 | 4/2015 |
| WO | WO2015128338 A1 | 9/2015 |

OTHER PUBLICATIONS

Alpha-thrin 100 SC label, Villa Crop Protection Ltd., Apr. 2012.*
CABA abstract 1993:103403 (1993).*
International Preliminary Report on Patentability, issued in PCT/EP2015/074067, dated Apr. 27, 2017.
International Search Report, issued in PCT/EP2015/074067, dated Nov. 20, 2015.

* cited by examiner

Primary Examiner — John Pak
(74) Attorney, Agent, or Firm — Brinks Gilson & Lione

(57) ABSTRACT

The invention relates to a method for controlling pests from the family of Pentatonidae, comprising the step of contacting the pests, their food supply, habitat or breeding grounds with a pesticidal mixture comprising as active compound I at least one component of the ginkgo tree I, selected from the group consisting of bilobalide, ginkgolide A, ginkgolide B, ginkgolide C, ginkgolide J and ginkgolide M, and at least one pesticidally active compound II and/or at least one fungicidally active compound III, as defined in the description, in a synergistically effective amount.
The invention further relates to certain of these mixtures.

7 Claims, No Drawings

METHOD AND PESTICIDAL MIXTURES FOR CONTROLLING PENTATOMIDAE PESTS

This application is a National Stage application of International Application No. PCT/EP2015/074067, filed Oct. 16, 2015, which claims the benefit of U.S. Provisional Application No. 62/064,493, filed Oct. 16, 2014.

The invention relates to a method for controlling Pentatomidae pests, particularly in soybean crops, by applying a pesticidal mixture comprising insecticidal components of the ginkgo tree. The invention further relates to pesticidal mixtures comprising insecticidal components of the ginkgo tree, their production and uses thereof.

Stink bugs (order of Hemiptera, family of Pentatomidae) are animal pests and true bugs. They are probably one of the most common pest problems in soybean (Stewart et al., Soybean Insects—Stink bugs, University of Tennessee Institute of Agriculture, W200 09-0098).

Stink bugs feed on over 52 plants, including native and ornamental trees, shrubs, vines, weeds, and many cultivated crops such as corn and cotton, as well as numerous uncultivated plants, and their preferred hosts are nearly all wild plants. They build up on these hosts and move to soybeans late in the season as their preferred foods mature.

Stink bugs may feed on many parts of the plant, however they typically target developing seed including the pods, meaning that injury to soybean seed is the primary problem associated with stink bug infestations.

Control of stinkbugs in soybean is often vital to prevent significant economic damage.

Insecticides commonly used to control stinkbugs include pyrethroids, neonicotinoids and organophosphates, though pyrethroid insecticides are usually the method of choice for controlling stink bugs in soybean. However, there are increasing problems with insecticide resistance, particularly in brown stink bug populations and particularly to pyrethroids. *Euschistus heros* can also be difficult to manage using organophosphates or endosulfan (Sosa-Gomez et al., 2009). There is therefore a need for effective ecological methods of controlling stinkbugs in soybean.

Particularly insecticides acting on the gamma-aminobutyric acid (GABA)-gated chloride channel (disclosed in e.g. WO 2005/085216 (EP1731512), WO2009/002809 and WO2009/080250) seem to be effective for controlling stinkbugs, especially in soybean such as described in WO2012/104331.

One typical problem arising in the field of pest control lies in the need to reduce the dosage rates of the active ingredient in order to reduce or avoid unfavorable environmental or toxicological effects whilst still allowing effective pest control.

Another problem encountered concerns the need to have available pest control agents which are effective against a broad spectrum of pests.

There also exists the need for pest control agents that combine knock-down activity with prolonged control, that is, fast action with long lasting action.

Another difficulty in relation to the use of pesticides is that the repeated and exclusive application of an individual pesticidal compound leads in many cases to a rapid selection of pests which have developed natural or adapted resistance against the active compound in question. Therefore there is a need for pest control agents that help prevent or overcome resistance.

It was therefore an object of the present invention to provide pesticidal mixtures for the control of Pentatomidae pests which solve at least one of the discussed problems such as reducing the dosage rate, enhancing the spectrum of activity or combining knock-down activity with prolonged control or as to resistance management.

It has been found that this object is in part or in whole achieved by applying the combination of active components of the ginkgo tree and further pesticides defined below.

Further it has been found that mixtures of the specific active components of the ginkgo tree and further insecticidal and/or fungicidal compounds show synergistic effect in the contest of various pests and fungi.

Accordingly, in one aspect of the invention there is provided a method for controlling pests from the family of Pentatonidae, comprising the step of contacting the pests, their food supply, habitat or breeding grounds with a pesticidal mixture comprising as active compounds 1) at least one compound I, which is a component of the ginkgo tree selected from the group consisting of bilobalide, ginkgolide A, ginkgolide B, ginkgolide C, ginkgolide J and ginkgolide M, and at least one pesticidally active compound II selected from groups M and/or L consisting of II-M.1 Acetylcholine esterase inhibitors:
II-M.1A carbamates: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; and
II-M.1B organophosphates, for example acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlor-vos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;
II-M.2. GABA-gated chloride channel antagonists:
II-M.2A cyclodiene organochlorine compounds: endosulfan or chlordane; and
II-M.2B fiproles: ethiprole, fipronil, flufiprole, pyrafluprole and pyriprole;
II-M.3 Sodium channel modulators:
II-M.3A pyrethroids: acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, heptafluthrin, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin, and transfluthrin; and II-M.3B sodium channel modulators: DDT, and methoxychlor;
II-M.4 Nicotinic acetylcholine receptor agonists:
II-M.4A neonicotinoids: acetamiprid, clothianidin, cycloxaprid, dinotefuran, imidacloprid, nitenpyram, thiacloprid, and thiamethoxam;
II-M.4A.2 (2E-)-1-[(6-Chloropyridin-3-yl)methyl]-N'-nitro-2-pentylidenehydrazinecarboximidamide;
II-M.4.A.3 1-[(6-Chloropyridin-3-yl)methyl]-7-methyl-8-nitro-5-propoxy-1,2,3,5,6,7-hexahydroimidazo[1,2-a]pyridine; and
II-M.4B nicotine;
II-M.5 Nicotinic acetylcholine receptor allosteric activators from the class of spinosyns: spinosad, and spinetoram;
II-M.6 Chloride channel activators from the class of avermectins and milbemycins: abamectin, emamectin benzoate, ivermectin, lepimectin, and milbemectin;
II-M.7 Juvenile hormone mimics:
II-M.7A juvenile hormone analogues: hydroprene, kinoprene, and methoprene; and
II-M.7B fenoxycarb, and pyriproxyfen;
II-M.8 miscellaneous non-specific inhibitors:
II-M.8A alkyl halides: methyl bromide, and other alkyl halides; and
II-M.8B chloropicrin, sulfuryl fluoride, borax, and tartar emetic;
II-M.9 Selective homopteran feeding blockers: pymetrozine, and flonicamid;
II-M.10 Mite growth inhibitors: clofentezine, hexythiazox, diflovidazin, and etoxazole;
II-M.11 Microbial disruptors of insect midgut membranes: *bacillus thuringiensis, bacillus sphaericus*, and the insecticidal proteins they produce: *bacillus thuringiensis* subsp. *israelensis, bacillus sphaericus, bacillus thuringiensis* subsp. *aizawai* and *bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;
II-M.12 Inhibitors of mitochondrial ATP synthase:
II-M.12A diafenthiuron, and organotin miticides: azocyclotin, cyhexatin, and fenbutatin oxide; and
II-M.12B propargite, and tetradifon;
II-M.13 Uncouplers of oxidative phosphorylation via disruption of the proton gradient: chlorfenapyr, DNOC, and sulfluramid;
II-M.14 Nicotinic acetylcholine receptor channel blockers: bensultap, cartap hydrochloride, thiocyclam, and thiosultap sodium;
II-M.15 Inhibitors of the chitin biosynthesis type 0: bistrifluron, chlorfluazuron, diflubenzuron, flucycloxuron, flufenoxuron, hexaflumuron, lufenuron, novaluron, noviflumuron, teflubenzuron, and triflumuron;
II-M.16 Inhibitors of the chitin biosynthesis type 1: buprofezin;
II-M.17 Moulting disruptors: cyromazine;
II-M.18 Ecdyson receptor agonists: methoxyfenozide, tebufenozide, halofenozide, fufenozide or chromafenozide;
II-M.19 Octopamin receptor agonists: amitraz;
II-M.20 Mitochondrial complex III electron transport inhibitors: hydramethylnon, acequinocyl, and fluacrypyrim;
II-M.21 Mitochondrial complex I electron transport inhibitors:
II-M.21A METI acaricides and insecticides: fenazaquin, fenpyroximate, pyrimidifen, pyridaben, tebufenpyrad, and tolfenpyrad; and
II-M.21B rotenone;
II-M.22 Voltage-dependent sodium channel blockers:
II-M.22A indoxacarb;
II-M.22B metaflumizone;
II-M.22B.1 2-[2-(4-Cyanophenyl)-1-[3-(trifluoromethyl)phenyl]ethylidene]-N-[4-(difluoromethoxy)phenyl]-hydrazinecarboxamide; and
II-M.22B.2 N-(3-Chloro-2-methylphenyl)-2-[(4-chlorophenyl)[4-[methyl(methylsulfonyl)amino]phenyl]methylene]-hydrazinecarboxamide;
II-M.23 Inhibitors of the of acetyl CoA carboxylase of the class of tetronic and tetramic acid derivatives: spirodiclofen, spiromesifen, and spirotetramat;
II-M.24 Mitochondrial complex IV electron transport inhibitors:
II-M.24A phosphorous compounds: aluminium phosphide, calcium phosphide, phosphine, and zinc phosphide; and
II-M.24B cyanide;
II-M.25 Mitochondrial complex II electron transport inhibitors from the class of beta-ketonitrile derivatives: cyenopyrafen, and cyflumetofen;
II-M.28 Ryanodine receptor-modulators from the class of diamides: flubendiamide, chlorantraniliprole (Rynaxypyr®), cyantraniliprole (Cyazypyr®), tetraniliprole; and the phthalamide compounds
II-M.28.1 (R)-3-Chlor-N1-{2-methyl-4-[1,2,2,2-tetrafluor-1-(trifluormethyl)ethyl]phenyl}-N2-(1-methyl-2-methylsulfonylethyl)phthalamid;
II-M.28.2 (S)-3-Chlor-N1-{2-methyl-4-[1,2,2,2-tetrafluor-1-(trifluormethyl)ethyl]phenyl}-N2-(1-methyl-2-methylsulfonylethyl)phthalamid;
II-M.28.3 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole);
II-M.28.4 methyl-2-[3,5-dibromo-2-({[3-bromo-1-(3-chlorpyridin-2-yl)-1H-pyrazol-5-yl]carbonyl}-amino)benzoyl]-1,2-dimethylhydrazinecarboxylate;
II-M.28.5a N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide;
IIM.28.5b N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide;
II-M.28.5c N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide;
II-M.28.5d N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide;
II-M.28.5h N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;
II-M.28.5i N-[2-(5-Amino-1,3,4-thiadiazol-2-yl)-4-chloro-6-methylphenyl]-3-bromo-1-(3-chloro-2-pyridinyl)-1H-pyrazole-5-carboxamide;
II-M.28.5j 3-Chloro-1-(3-chloro-2-pyridinyl)-N-[2,4-dichloro-6-[[(1-cyano-1-methylethyl)amino]carbonyl]phenyl]-1H-pyrazole-5-carboxamide;
II-M.28.5k 3-Bromo-N-[2,4-dichloro-6-(methylcarbamoyl)phenyl]-1-(3,5-dichloro-2-pyridyl)-1H-pyrazole-5-carboxamide;
II-M.28.5l N-[4-Chloro-2-[[(1,1-dimethylethyl)amino]carbonyl]-6-methylphenyl]-1-(3-chloro-2-pyridinyl)-3-(fluoromethoxy)-1H-pyrazole-5-carboxamide; and
II-M.28.6: cyhalodiamide;

II-M.29. insecticidal active compounds of unknown or uncertain mode of action: afidopyropen, afoxolaner, azadirachtin, amidoflumet, benzoximate, bifenazate, broflanilide, bromopropylate, chinomethionat, cryolite, dicloromezotiaz, dicofol, flufenerim, flometoquin, fluensulfone, fluhexafon, fluopyram, flupyradifurone, fluralaner, metoxadiazone, piperonyl butoxide, pyflubumide, pyridalyl, pyrifluquinazon, sulfoxaflor, tioxazafen, and triflumezopyrim;

II-M.29.3: 11-(4-chloro-2,6-dimethylphenyl)-12-hydroxy-1,4-dioxa-9-azadispiro[4.2.4.2]-tetradec-11-en-10-one;

II-M.29.4: 3-(4'-fluoro-2,4-dimethylbiphenyl-3-yl)-4-hydroxy-8-oxa-1-azaspiro[4.5]dec-3-en-2-one;

II-M.29.5: 1-[2-fluoro-4-methyl-5-[(2,2,2-trifluoroethyl)sulfinyl]phenyl]-3-(trifluoromethyl)-1H-1,2,4-triazole-5-amine, and actives on basis of *bacillus firmus* (Votivo, 1-1582); and II-M.29.6a (E/Z)—N-[1-[(6-chloro-3-pyridyl)methyl]-2-pyridylidene]-2,2,2-trifluoro-acetamide;

II-M.29.6b (E/Z)—N-[1-[(6-chloro-5-fluoro-3-pyridyl)methyl]-2-pyridylidene]-2,2,2-trifluoro-acetamide;

II-M.29.6c (E/Z)-2,2,2-trifluoro-N-[1-[(6-fluoro-3-pyridyl)methyl]-2-pyridylidene]acetamide;

II-M.29.6d (E/Z)—N-[1-[(6-bromo-3-pyridyl)methyl]-2-pyridylidene]-2,2,2-trifluoro-acetamide;

II-M.29.6e (E/Z)—N-[1-[1-(6-chloro-3-pyridyl)ethyl]-2-pyridylidene]-2,2,2-trifluoro-acetamide;

II-M.29.6f (E/Z)—N-[1-[(6-chloro-3-pyridyl)methyl]-2-pyridylidene]-2,2-difluoro-acetamide;

II-M.29.6g (E/Z)-2-chloro-N-[1-[(6-chloro-3-pyridyl)methyl]-2-pyridylidene]-2,2-difluoro-acetamide;

II-M.29.6h (E/Z)—N-[1-[(2-chloropyrimidin-5-yl)methyl]-2-pyridylidene]-2,2,2-trifluoro-acetamide;

II-M.29.6i (E/Z)—N-[1-[(6-chloro-3-pyridyl)methyl]-2-pyridylidene]-2,2,3,3,3-pentafluoro-propanamide);

II-M.29.6j N-[1-[(6-chloro-3-pyridyl)methyl]-2-pyridylidene]-2,2,2-trifluoro-thioacetamide; and II-M.29.6k N-[1-[(6-chloro-3-pyridyl)methyl]-2-pyridylidene]-2,2,2-trifluoro-N'-isopropyl-acetamidine;

II-M.29.8: fluazaindolizine;

II-M.29.9.a 4-[5-(3,5-dichlorophenyl)-5-(trifluoromethyl)-4H-isoxazol-3-yl]-2-methyl-N-(1-oxothietan-3-yl)benzamide; and II-M.29.9.b fluxametamide;

II-M.29.10 5-[3-[2,6-dichloro-4-(3,3-dichloroallyloxy)phenoxy]propoxy]-1H-pyrazole;

II-M.29.11.b 3-(benzoylmethylamino)-N-[2-bromo-4-[1,2,2,3,3,3-hexafluoro-1-(trifluoromethyl)propyl]-6-(trifluoromethyl)phenyl]-2-fluoro-benzamide;

II-M.29.11.c 3-(benzoylmethylamino)-2-fluoro-N-[2-iodo-4-[1,2,2,2-tetrafluoro-1-(trifluoromethyl)ethyl]-6-(trifluoromethyl)phenyl]-benzamide;

II-M.29.11.d N-[3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide;

II-M.29.11.e N-[3-[[[2-bromo-4-[1,2,2,2-tetrafluoro-1-(trifluoromethyl)ethyl]-6-(trifluoromethyl)phenyl]amino]carbonyl]-2-fluorophenyl]-4-fluoro-N-methyl-benzamide;

II-M.29.11.f 4-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide;

II-M.29.11.g 3-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide;

II-M.29.11.h 2-chloro-N-[3-[[[2-iodo-4-[1,2,2,2-tetrafluoro-1-(trifluoromethyl)ethyl]-6-(trifluoromethyl)phenyl]amino]carbonyl]phenyl]-3-pyridinecarboxamide;

II-M.29.11.i 4-cyano-N-[2-cyano-5-[[2,6-dibromo-4-[1,2,2,3,3,3-hexafluoro-1-(trifluoromethyl)propyl]phenyl]carbamoyl]phenyl]-2-methyl-benzamide;

II-M.29.11.j 4-cyano-3-[(4-cyano-2-methyl-benzoyl)amino]-N-[2,6-dichloro-4-[1,2,2,3,3,3-hexafluoro-1-(trifluoromethyl)propyl]phenyl]-2-fluoro-benzamide;

II-M.29.11.k N-[5-[[2-chloro-6-cyano-4-[1,2,2,3,3,3-hexafluoro-1-(trifluoromethyl)propyl]-phenyl]carbamoyl]-2-cyano-phenyl]-4-cyano-2-methyl-benzamide;

II-M.29.11.l N-[5-[[2-bromo-6-chloro-4-[2,2,2-trifluoro-1-hydroxy-1-(trifluoromethyl)ethyl]-phenyl]carbamoyl]-2-cyano-phenyl]-4-cyano-2-methyl-benzamide;

II-M.29.11.m N-[5-[[2-bromo-6-chloro-4-[1,2,2,3,3,3-hexafluoro-1-(trifluoromethyl)-propyl]phenyl]carbamoyl]-2-cyano-phenyl]-4-cyano-2-methyl-benzamide;

II-M.29.11.n 4-cyano-N-[2-cyano-5-[[2,6-dichloro-4-[1,2,2,3,3,3-hexafluoro-1-(trifluoromethyl)propyl]phenyl]carbamoyl]phenyl]-2-methyl-benzamide;

II-M.29.11.o 4-cyano-N-[2-cyano-5-[[2,6-dichloro-4-[1,2,2,2-tetrafluoro-1-(trifluoromethyl)ethyl]phenyl]carbamoyl]phenyl]-2-methyl-benzamide;

II-M.29.11.p N-[5-[[2-bromo-6-chloro-4-[1,2,2,2-tetrafluoro-1-(trifluoromethyl)ethyl]phenyl]-carbamoyl]-2-cyano-phenyl]-4-cyano-2-methyl-benzamide;

II-M.29.12.a 2-(1,3-Dioxan-2-yl)-6-[2-(3-pyridinyl)-5-thiazolyl]-pyridine;

II-M.29.12.b 2-[6-[2-(5-Fluoro-3-pyridinyl)-5-thiazolyl]-2-pyridinyl]-pyrimidine;

II-M.29.12.c 2-[6-[2-(3-Pyridinyl)-5-thiazolyl]-2-pyridinyl]-pyrimidine;

II-M.29.12.d N-Methylsulfonyl-6-[2-(3-pyridyl)thiazol-5-yl]pyridine-2-carboxamide;

II-M.29.12.e N-Methylsulfonyl-6-[2-(3-pyridyl)thiazol-5-yl]pyridine-2-carboxamide;

II-M.29.12.f N-Ethyl-N-[4-methyl-2-(3-pyridyl)thiazol-5-yl]-3-methylthio-propanamide;

II-M.29.12.g N-Methyl-N-[4-methyl-2-(3-pyridyl)thiazol-5-yl]-3-methylthio-propanamide;

II-M.29.12.h N,2-Dimethyl-N-[4-methyl-2-(3-pyridyl)thiazol-5-yl]-3-methylthio-propanamide;

II-M.29.12.i N-Ethyl-2-methyl-N-[4-methyl-2-(3-pyridyl)thiazol-5-yl]-3-methylthio-propanamide;

II-M.29.12.j N-[4-Chloro-2-(3-pyridyl)thiazol-5-yl]-N-ethyl-2-methyl-3-methylthio-propanamide;

II-M.29.12.k N-[4-Chloro-2-(3-pyridyl)thiazol-5-yl]-N,2-dimethyl-3-methylthio-propanamide;

II-M.29.12.l N-[4-Chloro-2-(3-pyridyl)thiazol-5-yl]-N-methyl-3-methylthio-propanamide;

II-M.29.12.m N-[4-Chloro-2-(3-pyridyl)thiazol-5-yl]-N-ethyl-3-methylthio-propanamide; or the compounds II-M.29.14a 1-[(6-Chloro-3-pyridinyl)methyl]-1,2,3,5,6,7-hexahydro-5-methoxy-7-methyl-8-nitro-imidazo[1,2-a]pyridine;

II-M.29.14b 1-[(6-Chloropyridin-3-yl)methyl]-7-methyl-8-nitro-1,2,3,5,6,7-hexahydroimidazo[1,2-a]pyridin-5-ol;

II-M.29.16a 1-isopropyl-N,5-dimethyl-N-pyridazin-4-yl-pyrazole-4-carboxamide; or II-M.29.16b 1-(1,2-dimethylpropyl)-N-ethyl-5-methyl-N-pyridazin-4-yl-pyrazole-4-carboxamide;

II-M.29.16c N,5-dimethyl-N-pyridazin-4-yl-1-(2,2,2-trifluoro-1-methyl-ethyl)pyrazole-4-carboxamide;

II-M.29.16d 1-[1-(1-cyanocyclopropyl)ethyl]-N-ethyl-5-methyl-N-pyridazin-4-yl-pyrazole-4-carboxamide;

II-M.29.16e N-ethyl-1-(2-fluoro-1-methyl-propyl)-5-methyl-N-pyridazin-4-yl-pyrazole-4-carboxamide;

II-M.29.16f 1-(1,2-dimethylpropyl)-N,5-dimethyl-N-pyridazin-4-yl-pyrazole-4-carboxamide;

II-M.29.16g 1-[1-(1-cyanocyclopropyl)ethyl]-N,5-dimethyl-N-pyridazin-4-yl-pyrazole-4-carboxamide;

II-M.29.16h N-methyl-1-(2-fluoro-1-methyl-propyl]-5-methyl-N-pyridazin-4-yl-pyrazole-4-carboxamide;

II-M.29.16i 1-(4,4-difluorocyclohexyl)-N-ethyl-5-methyl-N-pyridazin-4-yl-pyrazole-4-carboxamide; and II-M.29.16j 1-(4,4-difluorocyclohexyl)-N,5-dimethyl-N-pyridazin-4-yl-pyrazole-4-carboxamide;

II-M.29.17a N-(1-methylethyl)-2-(3-pyridinyl)-2H-indazole-4-carboxamide;

II-M.29.17b N-cyclopropyl-2-(3-pyridinyl)-2H-indazole-4-carboxamide;

II-M.29.17c N-cyclohexyl-2-(3-pyridinyl)-2H-indazole-4-carboxamide;

II-M.29.17d 2-(3-pyridinyl)-N-(2,2,2-trifluoroethyl)-2H-indazole-4-carboxamide;

II-M.29.17e 2-(3-pyridinyl)-N-[(tetrahydro-2-furanyl)methyl]-2H-indazole-5-carboxamide;

II-M.29.17f methyl 2-[[2-(3-pyridinyl)-2H-indazol-5-yl]carbonyl]hydrazinecarboxylate;

II-M.29.17g N-[(2,2-difluorocyclopropyl)methyl]-2-(3-pyridinyl)-2H-indazole-5-carboxamide;

II-M.29.17h N-(2,2-difluoropropyl)-2-(3-pyridinyl)-2H-indazole-5-carboxamide;

II-M.29.17i 2-(3-pyridinyl)-N-(2-pyrimidinylmethyl)-2H-indazole-5-carboxamide; and II-M.29.17j N-[(5-methyl-2-pyrazinyl)methyl]-2-(3-pyridinyl)-2H-indazole-5-carboxamide;

II-M.29.18a N-[3-chloro-1-(3-pyridyl)pyrazol-4-yl]-N-ethyl-3-(3,3,3-trifluoropropylsulfanyl)-propanamide;

II-M.29.18b N-[3-chloro-1-(3-pyridyl)pyrazol-4-yl]-N-ethyl-3-(3,3,3-trifluoropropylsulfinyl)-propanamide;

II-M.29.18c N-[3-chloro-1-(3-pyridyl)pyrazol-4-yl]-3-[(2,2-difluorocyclopropyl)-methylsulfanyl]-N-ethyl-propanamide; and II-M.29.18d N-[3-chloro-1-(3-pyridyl)pyrazol-4-yl]-3-[(2,2-difluorocyclopropyl)-methylsulfinyl]-N-ethyl-propanamide;

II-M.29.19 sarolaner;

II-M.29.20 lotilaner;

II-L Biopesticides:

II-L.1 Microbial pesticides with fungicidal, bactericidal, viricidal and/or plant defense activator activity: *Ampelomyces quisqualis, Aspergillus flavus, Aureobasidium pullulans, Bacillus altitudinis, B. amyloliquefaciens, B. megaterium, B. mojavensis, B. mycoides, B. simplex, B. solisalsi, B. subtilis, B. subtilis* var. *amyloliquefaciens, Candida oleophila, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea* f. *catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus polymyxa, Pantoea vagans, Penicillium bilaiae, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. violaceusniger, Talaromyces flavus, T. asperellum, T. atroviride, T. fertile, T. gamsii, T. harmatum, T. harzianum, T. polysporum, T. stromaticum, T. virens, T. viride, Typhula phacorrhiza, Ulocladium oudemansii, Verticillium dahlia*, and zucchini yellow mosaic virus (avirulent strain);

II-L.2 Biochemical pesticides with fungicidal, bactericidal, viricidal and/or plant defense activator activity: harpin protein, and *Reynoutria sachalinensis* extract;

II-L.3 Microbial pesticides with insecticidal, acaricidal, molluscidal and/or nematicidal activity: *Agrobacterium radiobacter, Bacillus cereus, B. firmus, B. thuringiensis, B. thuringiensis* ssp. *aizawai*, B. t. ssp. *israelensis*, B. t. ssp. *galleriae*, B. t. ssp. *tenebrionis, Beauveria bassiana, B. brongniartii, Burkholderia* spp., *Chromobacterium subtsugae, Cydia pomonella* granulovirus (CpGV), *Cryptophlebia leucotreta* granulovirus (CrleGV), *Flavobacterium* spp., *Helicoverpa armigera* nucleopolyhedrovirus (HearNPV), *Helicoverpa zea* nucleopolyhedrovirus (HzNPV), *Helicoverpa zea* single capsid nucleopolyhedrovirus (HzSNPV), *Heterorhabditis bacteriophora, Isaria fumosorosea, Lecanicillium longisporum, L. muscarium, Metarhizium anisopliae, Metarhizium anisopliae* var. *anisopliae*, M. *anisopliae* var. *acridum, Nomuraea rileyi, Paecilomyces fumosoroseus, P. lilacinus, Paenibacillus popilliae, Pasteuria* spp., *P. nishizawae, P. penetrans, P. ramosa, P. thornea, P. usgae, Pseudomonas fluorescens, Spodoptera littoralis* nucleopolyhedrovirus (SpliNPV), *Steinernema carpocapsae, S. feltiae, S. kraussei, Streptomyces galbus*, and *S. microflavus*, II-L.4 Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, extract of *Chenopodium ambrosiodes*, Neem oil, and Quillay extract;

II-L.5 Microbial pesticides with plant stress reducing, plant growth regulator, plant growth promoting and/or yield enhancing activity: *A. lipoferum, A. irakense, A. halopraeferens, B. elkanii, B. Haoningense, B. lupini, Delftia acidovorans, Glomus intraradices, Mesorhizobium* spp., *Rhizobium leguminosarum* bv. *phaseoli*, R. l. bv. *trifolii*, R. l. bv. *viciae, R. tropici*, and *Sinorhizobium meliloti*;

and/or at least one fungicidally active compound III selected from

III-F.I Respiration inhibitors

III-F.I1 Inhibitors of complex III at $Q_o$ site: azoxystrobin, coumethoxystrobin, coumoxystrobin, dimoxystrobin, enestroburin, fenaminstrobin, fenoxy-strobin/flufenoxystrobin, fluoxastrobin, kresoxim-methyl, mandestrobin, meto-minostrobin, orysastrobin, picoxystrobin, pyraclostrobin, pyrametostrobin, pyraoxystrobin, trifloxystrobin, 2-(2-(3-(2,6-dichlorophenyl)-1-methyl-allylideneaminooxy-methyl)-phenyl)-2-methoxyimino-N-methyl-acetamide, pyribencarb, triclopy-ricarb/chlorodincarb, famoxadone, and fenamidone, methyl-N-[2-[(1,4-dimethyl-5-phenyl-pyrazol-3-yl)oxylmethyl]phenyl]-N-methoxy-carbamate, 1-[3-chloro-2-[[1-(4-chlorophenyl)-1H-pyrazol-3-yl]oxymethyl]phenyl]-4-methyl-tetrazol-5-one, 1-[3-bromo-2-[[1-(4-chlorophenyl)pyrazol-3-yl]oxymethyl]phenyl]-4-methyl-tetrazol-5-one, 1-[2-[[1-(4-chlorophenyl)pyrazol-3-yl]oxymethyl]-3-methyl-phenyl]-4-methyl-tetrazol-5-one, 1-[2-[[1-(4-chlorophenyl)pyrazol-3-yl]oxymethyl]-3-fluoro-phenyl]-4-methyl-tetrazol-5-one, 1-[2-[[1-(2,4-dichlorophenyl)pyrazol-3-yl]oxymethyl]-3-fluoro-phenyl]-4-methyl-tetrazol-5-one, 1-[2-[[4-(4-chlorophenyl)thiazol-2-yl]oxymethyl]-3-methyl-phenyl]-4-methyl-tetrazol-5-one, 1-[3-chloro-2-[[4-(p-tolyl)thiazol-2-yl]oxymethyl]phenyl]-4-methyl-tetrazol-5-one, 1-[3-cyclopropyl-2-[[2-methyl-4-(1-methylpyrazol-3-yl)phenoxy]methyl]phenyl]-4-methyl-tetrazol-5-one, 1-[3-(difluoromethoxy)-2-[[2-methyl-4-(1-methylpyrazol-3-yl)phenoxy]methyl]phenyl]-4-methyl-tetrazol-5-one, 1-methyl-4-[3-methyl-2-[[2-methyl-4-(1-methylpyrazol-3-yl)phenoxy]methyl]phenyl]tetrazol-5-one, 1-methyl-4-[3-methyl-2-[[1-[3-(trifluoromethyl)phenyl]-ethylideneamino]oxy-methyl]phenyl]tetrazol-5-one, (Z,2E)-5-[1-(2,4-dichlorophenyl)pyrazol-3-yl]-oxy-2-methoxyimino-N,3-dimethyl-pent-3-enamide, (Z,2E)-5-[1-(4-chlorophenyl)pyrazol-3-yl]oxy-2-methoxyimino-N,3-dimethyl-pent-3-enamide, and (Z2E)-5-[1-(4-chloro-2-fluoro-phenyl)pyrazol-3-yl]oxy-2-methoxyimino-N,3-dimethyl-pent-3-enamide;

III-F.I2 inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-meth-oxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate, and (3S,6S,7R,8R)-8-benzyl-3-[3-[(isobutyryloxy)methoxy]-4-methoxypicolinamido]-6-methyl-4,9-dioxo-1,5-dioxonan-7-yl isobutyrate;

III-F.I3 inhibitors of complex II: benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, N-(7-fluoro-1,1,3-trimethyl-indan-4-yl)-1,3-dimethyl-pyrazole-4-carboxamide, and N-[2-(2,4-dichlorophenyl)-2-methoxy-1-methyl-ethyl]-3-(difluoromethyl)-1-methyl-pyrazole-4-carboxamide;

III-F.I4 other respiration inhibitors: diflumetorim, (5,8-difluoroquinazolin-4-yl)-{2-[2-fluoro-4-(4-trifluoromethyl-pyridin-2-yloxy)-phenyl]-ethyl}-amine; nitrophenyl derivates: binapacryl, dinobuton, dinocap, fluazinam, ferimzone; organometal compounds: fentin-acetate, fentin chloride, and fentin hydroxide; ametoctradin; and silthiofam;

III-F.II Sterol biosynthesis inhibitors:

III-F.II1 C14 demethylase inhibitors: triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thiocyanato-1H-[1,2,4]triazolo, 2-[rel-(2S;3R)-3-(2-chlorophenyl)-2-(2,4-difluorophenyl)-oxiranylmethyl]-2H-[1,2,4]triazole-3-thiol, 2-[2-chloro-4-(4-chlorophenoxy)phenyl]-1-(1,2,4-triazol-1-yl)pentan-2-ol, 1-[4-(4-chlorophenoxy)-2-(trifluoromethyl)phenyl]-1-cyclopropyl-2-(1,2,4-triazol-1-yl)ethanol, 2-[4-(4-chlorophenoxy)-2-(trifluoromethyl)phenyl]-1-(1,2,4-triazol-1-yl)butan-2-ol, 2-[2-chloro-4-(4-chlorophenoxy)phenyl]-1-(1,2,4-triazol-1-yl)butan-2-ol, 2-[4-(4-chlorophenoxy)-2-(trifluoromethyl)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)propan-2-ol, 2-[2-chloro-4-(4-chlorophenoxy)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)pentan-2-ol, 2-[4-(4-fluorophenoxy)-2-(trifluoromethyl)phenyl]-1-(1,2,4-triazol-1-yl)propan-2-ol, 2-[2-chloro-4-(4-chlorophenoxy)phenyl]-1-(1,2,4-triazol-1-yl)pent-3-yn-2-ol; imidazoles: imazalil, pefurazoate, prochloraz, triflumizol; pyrimidines, pyridines and piperazines: fenarimol, nuarimol, pyrifenox, triforine, and [3-(4-chloro-2-fluoro-phenyl)-5-(2,4-difluorophenyl)isoxazol-4-yl]-(3-pyridyl)methanol;

III-F.II2 Delta14-reductase inhibitors: aldimorph, dodemorph, dodemorph-acetate, fenpropimorph, tridemorph, fenpropidin, piperalin, and spiroxamine;

III-F.II3 Inhibitors of 3-keto reductase: fenhexamid;

III-F.III Nucleic acid synthesis inhibitors

III-F.III1 phenylamides or acyl amino acid fungicides: benalaxyl, benalaxyl-M, kiralaxyl, metalaxyl, metalaxyl-M (mefenoxam), ofurace, and oxadixyl;

III-F.III2 others: hymexazole, octhilinone, oxolinic acid, bupirimate, 5-fluorocytosine, 5-fluoro-2-(p-tolylmethoxy)pyrimidin-4-amine, and 5-fluoro-2-(4-fluorophenyl-methoxy)pyrimidin-4-amine;

III-F.IV Inhibitors of cell division and cytoskeleton

III-F.IV1 tubulin inhibitors from the class of
  benzimidazoles, and thiophanates: benomyl, carbendazim, fuberidazole, thiabendazole, and thiophanatemethyl;
  triazolopyrimidines: 5-chloro-7-(4-methylpiperidin-1-yl)-6-(2,4,6-trifluorophenyl)-[1,2,4]triazolo[1,5-a]pyrimidine; and III-F.IV2 other cell division inhibitors: diethofencarb, ethaboxam, pencycuron, fluopicolide, zoxamide, metrafenone, pyriofenone;

III-F.V Inhibitors of amino acid and protein synthesis:

III-F.V1 methionine synthesis inhibitors from the class of anilino-pyrimidines: cyprodinil, mepanipyrim, and pyrimethanil; and III-F.V2 protein synthesis inhibitors: blasticidin-S, kasugamycin, kasugamycin hydrochloride-hydrate, mildiomycin, streptomycin, oxytetracyclin, polyoxine, and validamycin A;

III-F.VI Signal transduction inhibitors:
III-F.VI1 MAP/histidine kinase inhibitors: fluoroimid, iprodione, procymidone, vinclozolin, fenpiclonil, and fludioxonil; and
III-F.VI2 G protein inhibitors: quinoxyfen;
III-F.VII Lipid and membrane synthesis inhibitors:
III-F.VII1 Phospholipid biosynthesis inhibitors: edifenphos, iprobenfos, pyrazophos, isopro thiolane;
III-F.VII2 lipid peroxidation: dicloran, quintozene, tecnazene, tolclofos-methyl, biphenyl, chloroneb, and etridiazole;
III-F.VII3 phospholipid biosynthesis and cell wall deposition: dimethomorph, flumorph, mandipropamid, pyrimorph, benthiavalicarb, iprovalicarb, valifenalate, and N-(1-(1-(4-cyano-phenyl)ethanesulfonyl)-but-2-yl) carbamic acid-(4-fluorophenyl) ester;
III-F.VII4 compounds affecting cell membrane permeability and fatty acids: propamocarb; and
III-F.VII5 fatty acid amide hydrolase inhibitors: oxathiapiprolin, 2-{3-[2-(1-{[3,5-bis(difluoromethyl-1H-pyrazol-1-yl]acetyl}piperidin-4-yl)-1,3-thiazol-4-yl]-4,5-dihydro-1,2-oxazol-5-yl}phenyl methanesulfonate, 2-{3-[2-(1-{[3,5-bis(difluoromethyl)-1H-pyrazol-1-yl]acetyl}piperidin-4-yl), and 1,3-thiazol-4-yl]-4,5-dihydro-1,2-oxazol-5-yl}-3-chlorophenyl methanesulfonate;
III-F.VIII Inhibitors with Multi Site Action:
III-F.VIII1 inorganic active substances: Bordeaux mixture, copper acetate, copper hydroxide, copper oxychloride, basic copper sulfate, and sulfur;
III-F.VIII2 thio- and dithiocarbamates: ferbam, mancozeb, maneb, metam, metiram, propineb, thiram, zineb, and ziram;
III-F.VIII3 organochlorine compounds from the class of phthalimides, sulfamides, and chloronitriles: anilazine, chlorothalonil, captafol, captan, folpet, dichlofluanid, dichlorophen, hexachlorobenzene, pentachlorphenole and its salts, phthalide, tolylfluanid, and N-(4-chloro-2-nitrophenyl)-N-ethyl-4-methyl-benzenesulfonamide; and
III-F.VIII4 guanidines and others: guanidine, dodine, dodine free base, guazatine, guazatine-acetate, iminoctadine, iminoctadine-triacetate, iminoctadine-tris(albesilate), dithianon, and 2,6-dimethyl-1H,5H-[1,4]dithiino[2,3-c:5,6-c']dipyrrole-1,3,5,7(2H,6H)-tetraone;
III-F.IX Cell wall synthesis inhibitors:
III-F.IX1 inhibitors of glucan synthesis: validamycin, and polyoxin B;
III-F.IX2 melanin synthesis inhibitors: pyroquilon, tricyclazole, carpropamid, dicyclomet, and fenoxanil;
III-F.X Plant defence inducers
III-F.X1 acibenzolar-S-methyl, probenazole, isotianil, tiadinil, prohexadione-calcium;
III-F.X2 phosphonates: fosetyl, fosetyl-aluminum, phosphorous acid and its salts; potassium or sodium bicarbonate; and
III-F.XI Unknown mode of action: bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, tolprocarb, oxin-copper, proquinazid, tebufloquin, tecloftalam, triazoxide, 2-butoxy-6-iodo-3-propylchromen-4-one, 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, N-(cyclopropylmethoxyimino-(6-difluoro-methoxy-2,3-di-fluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoro-methyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, methoxy-acetic acid 6-tert-butyl-8-fluoro-2,3-dimethyl-quinolin-4-yl ester, 3-[5-(4-methylphenyl)-2,3-dimethyl-isoxazolidin-3-yl]-pyridine, 3-[5-(4-chloro-phenyl)-2,3-dimethyl-isoxazolidin-3-yl]-pyridine (pyrisoxazole), N-(6-methoxy-pyridin-3-yl) cyclopropanecarboxylic acid amide, 5-chloro-1-(4,6-di-methoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate, picarbutrazox, pentyl N-[6-[[(Z)-[(1-methyltetrazol-5-yl)-phenyl-methylene]amino]oxymethyl]-2-pyridyl]carbamate, 2-[2-[(7,8-difluoro-2-methyl-3-quinolyl)oxy]-6-fluoro-phenyl]propan-2-ol, 2-[2-fluoro-6-[(8-fluoro-2-methyl-3-quinolyl)oxy]phenyl]propan-2-ol, 3-(5-fluoro-3,3,4,4-tetramethyl-3,4-dihydroisoquinolin-1-yl)quinoline, 3-(4,4-difluoro-3,3-dimethyl-3,4-dihydroisoquinolin-1-yl)quinoline, 3-(4,4,5-trifluoro-3,3-dimethyl-3,4-dihydroisoquinolin-1-yl) quinoline, and 9-fluoro-2,2-dimethyl-5-(3-quinolyl)-3H-1,4-benzoxazepine;
in a synergistically effective amount.

Moreover, it has been found that simultaneous, that is joint or separate, application of the active compound I and one or more compound(s) II and/or III, or successive application (that is immediately one after another and thereby creating the mixture "in-situ" on the desired location, as e.g. the plant) of the active compound I and one or more active compound(s) II and/or III allows enhanced control of pests compared to the control rates that are possible with the individual compounds.

The invention also provides for the use of a mixture according to the invention as disclosed above for controlling the pests from the family of Pentatomidae, preferably *Acrosternum* spp., *Euschistus* spp., *Nezara* spp and/or *Piezodrus* spp., in particular *Acrosternum hilare, Euschistus heros, Nezara viriduia* and/or *Piezodrus guildini*. Further is provided the use of a mixture of the invention as disclosed above for controlling *Halyomorpha halys* and/or *Dichelops* spp., such as *Dichelops furcatus* and *Dichelops melacanthos*.

The mixtures of the invention are partly novel and partly known. Accordingly, the invention also provides for pesticidal mixtures comprising as active compounds
1) at least one compound I, which is a component of the ginkgo tree selected from the group consisting of bilobalide, ginkgolide A, ginkgolide B, ginkgolide C, ginkgolide J and ginkgolide M,
and
2) at least one pesticidally active compound II selected from groups M and/or L consisting of
II-M.1 Acetylcholine esterase inhibitors:
II-M.1A carbamates: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; and II-M.2. GABA-gated chloride channel antagonists:

II-M.2A cyclodiene organochlorine compounds: endosulfan or chlordane; and

II-M.2B fiproles: ethiprole, fipronil, flufiprole, pyrafluprole and pyriprole;

II-M.3 Sodium channel modulators:

II-M.3B sodium channel modulators: DDT, and methoxychlor;

II-M.4 Nicotinic acetylcholine receptor agonists:

II-M.4A neonicotinoids: acetamiprid, clothianidin, cycloxaprid, dinotefuran, imidacloprid, nitenpyram, thiacloprid, and thiamethoxam;

II-M.4A.2 (2E-)-1-[(6-Chloropyridin-3-yl)methyl]-N'-nitro-2-pentylidenehydrazinecarboximidamide;

II-M4.A.3 1-[(6-Chloropyridin-3-yl)methyl]-7-methyl-8-nitro-5-propoxy-1,2,3,5,6,7-hexahydroimidazo[1,2-a]pyridine; and II-M.4B nicotine;

II-M.5 Nicotinic acetylcholine receptor allosteric activators from the class of spinosyns: spinosad, and spinetoram;

II-M.6 Chloride channel activators from the class of avermectins and milbemycins: abamectin, emamectin benzoate, ivermectin, lepimectin, and milbemectin;

II-M.7 Juvenile hormone mimics:

II-M.7A juvenile hormone analogues: hydroprene, kinoprene, and methoprene; and

II-M.7B fenoxycarb, and pyriproxyfen;

II-M.8 miscellaneous non-specific inhibitors:

II-M.8A alkyl halides: methyl bromide, and other alkyl halides; and

II-M.8B chloropicrin, sulfuryl fluoride, borax, and tartar emetic;

II-M.9 Selective homopteran feeding blockers: pymetrozine, and flonicamid;

II-M.10 Mite growth inhibitors: clofentezine, hexythiazox, diflovidazin, and etoxazole;

II-M.11 Microbial disruptors of insect midgut membranes: bacillus thuringiensis, bacillus sphaericus, and the insecticidal proteins they produce: bacillus thuringiensis subsp. israelensis, bacillus sphaericus, bacillus thuringiensis subsp. aizawai and bacillus thuringiensis subsp. tenebrionis, or the Bt crop proteins: Cry1Ab, Cry1Ac, Cry1Fa, Cry2Ab, mCry3A, Cry3Ab, Cry3Bb and Cry34/35Ab1;

II-M.12 Inhibitors of mitochondrial ATP synthase:

II-M.12A diafenthiuron, and organotin miticides: azocyclotin, cyhexatin, and fenbutatin oxide; and II-M.12B propargite, and tetradifon;

II-M.13 Uncouplers of oxidative phosphorylation via disruption of the proton gradient: chlorfenapyr, DNOC, and sulfluramid;

II-M.14 Nicotinic acetylcholine receptor channel blockers: bensultap, cartap hydrochloride, thiocyclam, and thiosultap sodium;

II-M.15 Inhibitors of the chitin biosynthesis type 0: bistrifluron, chlorfluazuron, diflubenzuron, flucycloxuron, flufenoxuron, hexaflumuron, lufenuron, novaluron, noviflumuron, teflubenzuron, and triflumuron;

II-M.16 Inhibitors of the chitin biosynthesis type 1: buprofezin;

II-M.17 Moulting disruptors: cyromazine;

II-M.18 Ecdyson receptor agonists: methoxyfenozide, tebufenozide, halofenozide, fufenozide or chromafenozide;

II-M.19 Octopamin receptor agonists: amitraz;

II-M.20 Mitochondrial complex III electron transport inhibitors: hydramethylnon, acequinocyl, and fluacrypyrim;

II-M.21 Mitochondrial complex I electron transport inhibitors:

II-M.21A METI acaricides and insecticides: fenazaquin, fenpyroximate, pyrimidifen, pyridaben, tebufenpyrad, and tolfenpyrad; and II-M.21B rotenone;

II-M.22 Voltage-dependent sodium channel blockers:

II-M.22A indoxacarb;

II-M.22B metaflumizone;

II-M.22B.1 2-[2-(4-Cyanophenyl)-1-[3-(trifluoromethyl) phenyl]ethylidene]-N-[4-(difluoromethoxy)phenyl]-hydrazinecarboxamide; and II-M.22B.2 N-(3-Chloro-2-methylphenyl)-2-[(4-chlorophenyl)[4-[methyl(methylsulfonyl)amino]phenyl]methylene]-hydrazinecarboxamide;

II-M.23 Inhibitors of the of acetyl CoA carboxylase of the class of tetronic and tetramic acid derivatives: spirodiclofen, spiromesifen, and spirotetramat;

II-M.24 Mitochondrial complex IV electron transport inhibitors:

II-M.24A phosphorous compounds: aluminium phosphide, calcium phosphide, phosphine, and zinc phosphide; and II-M.24B cyanide;

II-M.25 Mitochondrial complex II electron transport inhibitors from the class of beta-ketonitrile derivatives: cyenopyrafen, and cyflumetofen;

II-M.28 Ryanodine receptor-modulators from the class of diamides: flubendiamide, chlorantraniliprole (Rynaxypyr®), cyantraniliprole (Cyazypyr®), tetraniliprole; and the phthalamide compounds II-M.28.1 (R)-3-Chlor-N1-{2-methyl-4-[1,2,2,2-tetrafluor-1-(trifluormethyl)ethyl]phenyl}-N2-(1-methyl-2-methylsulfonylethyl)phthalamid;

II-M.28.2 (S)-3-Chlor-N1-{2-methyl-4-[1,2,2,2-tetrafluor-1-(trifluormethyl)ethyl]phenyl}-N2-(1-methyl-2-methylsulfonylethyl)phthalamid;

II-M.28.3 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole);

II-M.28.4 methyl-2-[3,5-dibromo-2-({[3-bromo-1-(3-chlorpyridin-2-yl)-1H-pyrazol-5-yl]carbonyl}-amino)benzoyl]-1,2-dimethylhydrazinecarboxylate;

II-M.28.5a N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide;

IIM.28.5b N-[4-chloro-2-[(diethyl-lambda-4-sulfanylidene) carbamoyl]-6-methyl-phenyl]-2-(3-chloro-2-pyridyl)-5-(trifluoromethyl)pyrazole-3-carboxamide;

II-M.28.5c N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide;

II-M.28.5d N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide;

II-M.28.5h N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;

II-M.28.5i N-[2-(5-Amino-1,3,4-thiadiazol-2-yl)-4-chloro-6-methylphenyl]-3-bromo-1-(3-chloro-2-pyridinyl)-1H-pyrazole-5-carboxamide;

II-M.28.5j 3-Chloro-1-(3-chloro-2-pyridinyl)-N-[2,4-dichloro-6-[[(1-cyano-1-methylethyl)amino]carbonyl]phenyl]-1H-pyrazole-5-carboxamide;

II-M.28.5k 3-Bromo-N-[2,4-dichloro-6-(methylcarbamoyl) phenyl]-1-(3,5-dichloro-2-pyridyl)-1H-pyrazole-5-carboxamide;

II-M.28.5l N-[4-Chloro-2-[[(1,1-dimethylethyl)amino]carbonyl]-6-methylphenyl]-1-(3-chloro-2-pyridinyl)-3-(fluoromethoxy)-1H-pyrazole-5-carboxamide; and II-M.28.6: cyhalodiamide;

II-M.29. insecticidal active compounds of unknown or uncertain mode of action: afidopyropen, afoxolaner, azadirachtin, amidoflumet, benzoximate, bifenazate, broflanilide, bromopropylate, chinomethionat, cryolite, dicloromezotiaz, dicofol, flufenerim, flometoquin, fluensulfone, fluhexafon, fluopyram, flupyradifurone, fluralaner, metoxadiazone, piperonyl butoxide, pyflubumide, pyridalyl, pyrifluquinazon, sulfoxaflor, tioxazafen, and triflumezopyrim;

II-M.29.3: 11-(4-chloro-2,6-dimethylphenyl)-12-hydroxy-1, 4-dioxa-9-azadispiro[4.2.4.2]-tetradec-11-en-10-one;

II-M.29.4: 3-(4'-fluoro-2,4-dimethylbiphenyl-3-yl)-4-hydroxy-8-oxa-1-azaspiro[4.5]dec-3-en-2-one;

II-M.29.5: 1-[2-fluoro-4-methyl-5-[(2,2,2-trifluoroethyl) sulfinyl]phenyl]-3-(trifluoromethyl)-1H-1,2,4-triazole-5-amine, and actives on basis of *bacillus firmus* (Votivo, 1-1582); and II-M.29.6a (E/Z)—N-[1-[(6-chloro-3-pyridyl)methyl]-2-pyridylidene]-2,2,2-trifluoro-acetamide;

II-M.29.6b (E/Z)—N-[1-[(6-chloro-5-fluoro-3-pyridyl) methyl]-2-pyridylidene]-2,2,2-trifluoro-acetamide;

II-M.29.6c (E/Z)-2,2,2-trifluoro-N-[1-[(6-fluoro-3-pyridyl) methyl]-2-pyridylidene]acetamide;

II-M.29.6d (E/Z)—N-[1-[(6-bromo-3-pyridyl)methyl]-2-pyridylidene]-2,2,2-trifluoro-acetamide;

II-M.29.6e (E/Z)—N-[1-[1-(6-chloro-3-pyridyl)ethyl]-2-pyridylidene]-2,2,2-trifluoro-acetamide;

II-M.29.6f (E/Z)—N-[1-[(6-chloro-3-pyridyl)methyl]-2-pyridylidene]-2,2-difluoro-acetamide;

II-M.29.6g (E/Z)-2-chloro-N-[1-[(6-chloro-3-pyridyl) methyl]-2-pyridylidene]-2,2-difluoro-acetamide;

II-M.29.6h (E/Z)—N-[1-[(2-chloropyrimidin-5-yl)methyl]-2-pyridylidene]-2,2,2-trifluoro-acetamide;

II-M.29.6i (E/Z)—N-[1-[(6-chloro-3-pyridyl)methyl]-2-pyridylidene]-2,2,3,3,3-pentafluoro-propanamide);

II-M.29.6j N-[1-[(6-chloro-3-pyridyl)methyl]-2-pyridylidene]-2,2,2-trifluoro-thioacetamide; and II-M.29.6k N-[1-[(6-chloro-3-pyridyl)methyl]-2-pyridylidene]-2,2,2-trifluoro-N'-isopropyl-acetamidine;

II-M.29.8: fluazaindolizine;

II-M.29.9.a 4-[5-(3,5-dichlorophenyl)-5-(trifluoromethyl)-4H-isoxazol-3-yl]-2-methyl-N-(1-oxothietan-3-yl)benzamide; and II-M.29.9.b fluxametamide;

II-M.29.10 5-[3-[2,6-dichloro-4-(3,3-dichloroallyloxy)phenoxy]propoxy]-1H-pyrazole;

II-M.29.11.b 3-(benzoylmethylamino)-N-[2-bromo-4-[1,2, 2,3,3,3-hexafluoro-1-(trifluoromethyl)propyl]-6-(trifluoromethyl)phenyl]-2-fluoro-benzamide;

II-M.29.11.c 3-(benzoylmethylamino)-2-fluoro-N-[2-iodo-4-[1,2,2,2-tetrafluoro-1-(trifluoromethyl)ethyl]-6-(trifluoromethyl)phenyl]-benzamide;

II-M.29.11.d N-[3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide;

II-M.29.11.e N-[3-[[[2-bromo-4-[1,2,2,2-tetrafluoro-1-(trifluoromethyl)ethyl]-6-(trifluoromethyl)phenyl]amino]carbonyl]-2-fluorophenyl]-4-fluoro-N-methyl-benzamide;

II-M.29.11.f 4-fluoro-N-[2-fluoro-3-[[[2-iodo-4-[1,2,2,2-tetrafluoro-1-(trifluoromethyl)ethyl]-6-(trifluoromethyl) phenyl]amino]carbonyl]phenyl]-N-methyl-benzamide;

II-M.29.11.g 3-fluoro-N-[2-fluoro-3-[[[2-iodo-4-[1,2,2,2-tetrafluoro-1-(trifluoromethyl)ethyl]-6-(trifluoromethyl) phenyl]amino]carbonyl]phenyl]-N-methyl-benzamide;

II-M.29.11.h 2-chloro-N-[3-[[[2-iodo-4-[1,2,2,2-tetrafluoro-1-(trifluoromethyl)ethyl]-6-(trifluoromethyl)phenyl] amino]carbonyl]phenyl]-3-pyridinecarboxamide;

II-M.29.11.i 4-cyano-N-[2-cyano-5-[[2,6-dibromo-4-[1,2,2, 3,3,3-hexafluoro-1-(trifluoromethyl)propyl]phenyl]carbamoyl]phenyl]-2-methyl-benzamide;

II-M.29.11.j 4-cyano-3-[(4-cyano-2-methyl-benzoyl) amino]-N-[2,6-dichloro-4-[1,2,2,3,3,3-hexafluoro-1-(trifluoromethyl)propyl]phenyl]-2-fluoro-benzamide;

II-M.29.11.k N-[5-[[2-chloro-6-cyano-4-[1,2,2,3,3,3-hexafluoro-1-(trifluoromethyl)propyl]-phenyl]carbamoyl]-2-cyano-phenyl]-4-cyano-2-methyl-benzamide;

II-M.29.11.l N-[5-[[2-bromo-6-chloro-4-[2,2,2-trifluoro-1-hydroxy-1-(trifluoromethyl)ethyl]-phenyl]carbamoyl]-2-cyano-phenyl]-4-cyano-2-methyl-benzamide;

II-M.29.11.m N-[5-[[2-bromo-6-chloro-4-[1,2,2,3,3,3-hexafluoro-1-(trifluoromethyl)-propyl]phenyl]carbamoyl]-2-cyano-phenyl]-4-cyano-2-methyl-benzamide;

II-M.29.11.n 4-cyano-N-[2-cyano-5-[[2,6-dichloro-4-[1,2,2, 3,3,3-hexafluoro-1-(trifluoromethyl)propyl]phenyl]carbamoyl]phenyl]-2-methyl-benzamide;

II-M.29.11.o 4-cyano-N-[2-cyano-5-[[2,6-dichloro-4-[1,2,2, 2-tetrafluoro-1-(trifluoromethyl)ethyl]phenyl]carbamoyl] phenyl]-2-methyl-benzamide;

II-M.29.11.p N-[5-[[2-bromo-6-chloro-4-[1,2,2,2-tetrafluoro-1-(trifluoromethyl)ethyl]phenyl]-carbamoyl]-2-cyano-phenyl]-4-cyano-2-methyl-benzamide;

II-M.29.12.a 2-(1,3-Dioxan-2-yl)-6-[2-(3-pyridinyl)-5-thiazolyl]-pyridine;

II-M.29.12.b 2-[6-[2-(5-Fluoro-3-pyridinyl)-5-thiazolyl]-2-pyridinyl]-pyrimidine;

II-M.29.12.c 2-[6-[2-(3-Pyridinyl)-5-thiazolyl]-2-pyridinyl]-pyrimidine;

II-M.29.12.d N-Methylsulfonyl-6-[2-(3-pyridyl)thiazol-5-yl]pyridine-2-carboxamide;

II-M.29.12.e N-Methylsulfonyl-6-[2-(3-pyridyl)thiazol-5-yl]pyridine-2-carboxamide;

II-M.29.12.f N-Ethyl-N-[4-methyl-2-(3-pyridyl)thiazol-5-yl]-3-methylthio-propanamide;

II-M.29.12.g N-Methyl-N-[4-methyl-2-(3-pyridyl)thiazol-5-yl]-3-methylthio-propanamide;

II-M.29.12.h N,2-Dimethyl-N-[4-methyl-2-(3-pyridyl)thiazol-5-yl]-3-methylthio-propanamide;

II-M.29.12.i N-Ethyl-2-methyl-N-[4-methyl-2-(3-pyridyl) thiazol-5-yl]-3-methylthio-propanamide;

II-M.29.12.j N-[4-Chloro-2-(3-pyridyl)thiazol-5-yl]-N-ethyl-2-methyl-3-methylthio-propanamide;

II-M.29.12.k N-[4-Chloro-2-(3-pyridyl)thiazol-5-yl]-N,2-dimethyl-3-methylthio-propanamide;

II-M.29.12.l N-[4-Chloro-2-(3-pyridyl)thiazol-5-yl]-N-methyl-3-methylthio-propanamide;

II-M.29.12.m N-[4-Chloro-2-(3-pyridyl)thiazol-5-yl]-N-ethyl-3-methylthio-propanamide; or the compounds II-M.29.14a 1-[(6-Chloro-3-pyridinyl)methyl]-1,2,3,5,6,7-hexahydro-5-methoxy-7-methyl-8-nitro-imidazo[1,2-a] pyridine;

II-M.29.14b 1-[(6-Chloropyridin-3-yl)methyl]-7-methyl-8-nitro-1,2,3,5,6,7-hexahydroimidazo[1,2-a]pyridin-5-ol;

II-M.29.16a 1-isopropyl-N,5-dimethyl-N-pyridazin-4-yl-pyrazole-4-carboxamide; or II-M.29.16b 1-(1,2-dimethylpropyl)-N-ethyl-5-methyl-N-pyridazin-4-yl-pyrazole-4-carboxamide;
II-M.29.16c N,5-dimethyl-N-pyridazin-4-yl-1-(2,2,2-trifluoro-1-methyl-ethyl)pyrazole-4-carboxamide;
II-M.29.16d 1-[1-(1-cyanocyclopropyl)ethyl]-N-ethyl-5-methyl-N-pyridazin-4-yl-pyrazole-4-carboxamide;
II-M.29.16e N-ethyl-1-(2-fluoro-1-methyl-propyl)-5-methyl-N-pyridazin-4-yl-pyrazole-4-carboxamide;
II-M.29.16f 1-(1,2-dimethylpropyl)-N,5-dimethyl-N-pyridazin-4-yl-pyrazole-4-carboxamide;
II-M.29.16g 1-[1-(1-cyanocyclopropyl)ethyl]-N,5-dimethyl-N-pyridazin-4-yl-pyrazole-4-carboxamide;
II-M.29.16h N-methyl-1-(2-fluoro-1-methyl-propyl]-5-methyl-N-pyridazin-4-yl-pyrazole-4-carboxamide;
II-M.29.16i 1-(4,4-difluorocyclohexyl)-N-ethyl-5-methyl-N-pyridazin-4-yl-pyrazole-4-carboxamide; and
II-M.29.16j 1-(4,4-difluorocyclohexyl)-N,5-dimethyl-N-pyridazin-4-yl-pyrazole-4-carboxamide;
II-M.29.17a N-(1-methylethyl)-2-(3-pyridinyl)-2H-indazole-4-carboxamide;
II-M.29.17b N-cyclopropyl-2-(3-pyridinyl)-2H-indazole-4-carboxamide;
II-M.29.17c N-cyclohexyl-2-(3-pyridinyl)-2H-indazole-4-carboxamide;
II-M.29.17d 2-(3-pyridinyl)-N-(2,2,2-trifluoroethyl)-2H-indazole-4-carboxamide;
II-M.29.17e 2-(3-pyridinyl)-N-[(tetrahydro-2-furanyl)methyl]-2H-indazole-5-carboxamide;
II-M.29.17f methyl 2-[[2-(3-pyridinyl)-2H-indazol-5-yl]carbonyl]hydrazinecarboxylate;
II-M.29.17g N-[(2,2-difluorocyclopropyl)methyl]-2-(3-pyridinyl)-2H-indazole-5-carboxamide;
II-M.29.17h N-(2,2-difluoropropyl)-2-(3-pyridinyl)-2H-indazole-5-carboxamide;
II-M.29.17i 2-(3-pyridinyl)-N-(2-pyrimidinylmethyl)-2H-indazole-5-carboxamide; and
II-M.29.17j N-[(5-methyl-2-pyrazinyl)methyl]-2-(3-pyridinyl)-2H-indazole-5-carboxamide;
II-M.29.18a N-[3-chloro-1-(3-pyridyl)pyrazol-4-yl]-N-ethyl-3-(3,3,3-trifluoropropylsulfanyl)-propanamide;
II-M.29.18b N-[3-chloro-1-(3-pyridyl)pyrazol-4-yl]-N-ethyl-3-(3,3,3-trifluoropropylsulfinyl)-propanamide;
II-M.29.18c N-[3-chloro-1-(3-pyridyl)pyrazol-4-yl]-3-[(2,2-difluorocyclopropyl)-methylsulfanyl]-N-ethyl-propanamide; and
II-M.29.18d N-[3-chloro-1-(3-pyridyl)pyrazol-4-yl]-3-[(2,2-difluorocyclopropyl)-methylsulfinyl]-N-ethyl-propanamide;
II-M.29.19 sarolaner;
II-M.29.20 lotilaner;
II-L Biopesticides:
II-L.1 Microbial pesticides with fungicidal, bactericidal, viricidal and/or plant defense activator activity: *Ampelomyces quisqualis, Aspergillus flavus, Aureobasidium pullulans, Bacillus altitudinis, B. amyloliquefaciens, B. megaterium, B. mojavensis, B. mycoides, B. simplex, B. solisalsi, B. subtilis, B. subtilis* var. *amyloliquefaciens, Candida oleophila, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea* f. *catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus polymyxa, Pantoea vagans, Penicillium bilaiae, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. violaceusniger, Talaromyces flavus, T. asperellum, T. atroviride, T. fertile, T. gamsii, T. harmatum, T. harzianum, T. polysporum, T. stromaticum, T. virens, T. viride, Typhula phacorrhiza, Ulocladium oudemansii, Verticillium dahlia*, and zucchini yellow mosaic virus (avirulent strain);
II-L.2 Biochemical pesticides with fungicidal, bactericidal, viricidal and/or plant defense activator activity: harpin protein, and *Reynoutria sachalinensis* extract;
II-L.3 Microbial pesticides with insecticidal, acaricidal, molluscidal and/or nematicidal activity: *Agrobacterium radiobacter, Bacillus cereus, B. firmus, B. thuringiensis, B. thuringiensis* ssp. *aizawai*, B. t. ssp. *israelensis*, B. t. ssp. *galleriae*, B. t. ssp. *tenebrionis, Beauveria bassiana, B. brongniartii, Burkholderia* spp., *Chromobacterium subtsugae, Cydia pomonella* granulovirus (CpGV), *Cryptophlebia leucotreta* granulovirus (CrleGV), *Flavobacterium* spp., *Helicoverpa armigera* nucleopolyhedrovirus (HearNPV), *Helicoverpa zea* nucleopolyhedrovirus (HzNPV), *Helicoverpa zea* single capsid nucleopolyhedrovirus (HzSNPV), *Heterorhabditis bacteriophora, Isaria fumosorosea, Lecanicillium longisporum, L. muscarium, Metarhizium anisopliae, Metarhizium anisopliae* var. *anisopliae, M. anisopliae* var. *acridum, Nomuraea rileyi, Paecilomyces fumosoroseus, P. lilacinus, Paenibacillus popilliae, Pasteuria* spp., *P. nishizawae, P. penetrans, P. ramosa, P. thornea, P. usgae, Pseudomonas fluorescens, Spodoptera littoralis* nucleopolyhedrovirus (SpliNPV), *Steinernema carpocapsae, S. feltiae, S. kraussei, Streptomyces galbus*, and *S. microflavus,*
II-L.4 Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, extract of *Chenopodium ambrosiodes*, Neem oil, and Quillay extract;
II-L.5 Microbial pesticides with plant stress reducing, plant growth regulator, plant growth promoting and/or yield enhancing activity: *A. lipoferum, A. irakense, A. halopraeferens, B. elkanii, B. liaoningense, B. lupini, Delftia acidovorans, Glomus intraradices, Mesorhizobium* spp., *Rhizobium leguminosarum* bv. *phaseoli*, R. l. bv. *trifolii*, R. l. bv. *viciae, R. tropici*, and *Sinorhizobium meliloti;*
and/or at least one fungicidally active compound III selected from
III-F.I Respiration inhibitors
III-F.I1 Inhibitors of complex III at $Q_o$ site: azoxystrobin, coumethoxystrobin, coumoxystrobin, dimoxystrobin, enestroburin, fenaminstrobin, fenoxy-strobin/flufenoxystrobin, fluoxastrobin, kresoxim-methyl, mandestrobin, meto-minostrobin, orysastrobin, picoxystrobin, pyraclostrobin, pyrametostrobin, pyraoxystrobin, trifloxystrobin, 2-(2-(3-(2,6-dichlorophenyl)-1-methyl-allylideneaminooxy-methyl)-phenyl)-2-methoxyimino-N-methyl-acetamide, pyribencarb, triclopy-ricarb/chlorodincarb, famoxadone, and fenamidone, methyl-N-[2-[(1,4-dimethyl-5-phenyl-pyrazol-3-yl)oxylmethyl]

phenyl]-N-methoxy-carbamate, 1-[3-chloro-2-[[1-(4-chlorophenyl)-1H-pyrazol-3-yl]oxymethyl]phenyl]-4-methyl-tetrazol-5-one, 1-[3-bromo-2-[[1-(4-chlorophenyl)pyrazol-3-yl]oxymethyl]phenyl]-4-methyl-tetrazol-5-one, 1-[2-[[1-(4-chlorophenyl)pyrazol-3-yl]oxymethyl]-3-methyl-phenyl]-4-methyl-tetrazol-5-one, 1-[2-[[1-(4-chlorophenyl)pyrazol-3-yl]oxymethyl]-3-fluoro-phenyl]-4-methyl-tetrazol-5-one, 1-[2-[[1-(2,4-dichlorophenyl)pyrazol-3-yl]oxymethyl]-3-fluoro-phenyl]-4-methyl-tetrazol-5-one, 1-[2-[[4-(4-chlorophenyl)thiazol-2-yl]oxymethyl]-3-methyl-phenyl]-4-methyl-tetrazol-5-one, 1-[3-chloro-2-[[4-(p-tolyl)thiazol-2-yl]oxymethyl]phenyl]-4-methyl-tetrazol-5-one, 1-[3-cyclopropyl-2-[[2-methyl-4-(1-methylpyrazol-3-yl)phenoxy]methyl]phenyl]-4-methyl-tetrazol-5-one, 1-[3-(difluoromethoxy)-2-[[2-methyl-4-(1-methylpyrazol-3-yl)phenoxy]methyl]phenyl]-4-methyl-tetrazol-5-one, 1-methyl-4-[3-methyl-2-[[2-methyl-4-(1-methylpyrazol-3-yl)phenoxy]methyl]phenyl]tetrazol-5-one, 1-methyl-4-[3-methyl-2-[[1-[3-(trifluoromethyl)phenyl]-ethylideneamino]oxy-methyl]phenyl]tetrazol-5-one, (Z,2E)-5-[1-(2,4-dichlorophenyl)pyrazol-3-yl]-oxy-2-methoxyimino-N,3-dimethyl-pent-3-enamide, (Z,2E)-5-[1-(4-chlorophenyl)pyrazol-3-yl]oxy-2-methoxyimino-N,3-dimethyl-pent-3-enamide, and (Z2E)-5-[1-(4-chloro-2-fluoro-phenyl)pyrazol-3-yl]oxy-2-methoxyimino-N,3-dimethyl-pent-3-enamide;

III-F.I2 inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-meth-oxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate, and (3S,6S,7R,8R)-8-benzyl-3-[3-[(isobutyryloxy)methoxy]-4-methoxypicolinamido]-6-methyl-4,9-dioxo-1,5-dioxonan-7-yl isobutyrate;

III-F.I3 inhibitors of complex II: benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, N-(7-fluoro-1,1,3-trimethyl-indan-4-yl)-1,3-dimethyl-pyrazole-4-carboxamide, and N-[2-(2,4-dichlorophenyl)-2-methoxy-1-methyl-ethyl]-3-(difluoromethyl)-1-methyl-pyrazole-4-carboxamide;

III-F.I4 other respiration inhibitors: diflumetorim, (5,8-difluoroquinazolin-4-yl)-{2-[2-fluoro-4-(4-trifluoromethyl-pyridin-2-yloxy)-phenyl]-ethyl}-amine; nitrophenyl derivates: binapacryl, dinobuton, dinocap, fluazinam, ferimzone; organometal compounds: fentin-acetate, fentin chloride, and fentin hydroxide; ametoctradin; and silthiofam;

III-F.II Sterol biosynthesis inhibitors:

III-F.II1 C14 demethylase inhibitors:
triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thiocyanato-1H-[1,2,4]triazolo, 2-[rel-(2S;3R)-3-(2-chlorophenyl)-2-(2,4-difluorophenyl)-oxiranylmethyl]-2H-[1,2,4]triazole-3-thiol, 2-[2-chloro-4-(4-chlorophenoxy)phenyl]-1-(1,2,4-triazol-1-yl)pentan-2-ol, 1-[4-(4-chlorophenoxy)-2-(trifluoromethyl)phenyl]-1-cyclopropyl-2-(1,2,4-triazol-1-yl)ethanol, 2-[4-(4-chlorophenoxy)-2-(trifluoromethyl)phenyl]-1-(1,2,4-triazol-1-yl)butan-2-ol, 2-[2-chloro-4-(4-chlorophenoxy)phenyl]-1-(1,2,4-triazol-1-yl)butan-2-ol, 2-[4-(4-chlorophenoxy)-2-(trifluoromethyl)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)propan-2-ol, 2-[2-chloro-4-(4-chlorophenoxy)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)pentan-2-ol, 2-[4-(4-fluorophenoxy)-2-(trifluoromethyl)phenyl]-1-(1,2,4-triazol-1-yl)propan-2-ol, 2-[2-chloro-4-(4-chlorophenoxy)phenyl]-1-(1,2,4-triazol-1-yl)pent-3-yn-2-ol; imidazoles: imazalil, pefurazoate, prochloraz, triflumizol;

pyrimidines, pyridines and piperazines: fenarimol, nuarimol, pyrifenox, triforine, and [3-(4-chloro-2-fluorophenyl)-5-(2,4-difluorophenyl)isoxazol-4-yl]-(3-pyridyl)methanol;

III-F.II2 Delta14-reductase inhibitors: aldimorph, dodemorph, dodemorph-acetate, fenpropimorph, tridemorph, fenpropidin, piperalin, and spiroxamine;

III-F.II3 Inhibitors of 3-keto reductase: fenhexamid;

III-F.III Nucleic acid synthesis inhibitors

IIIF.III1 phenylamides or acyl amino acid fungicides: benalaxyl, benalaxyl-M, kiralaxyl, metalaxyl, metalaxyl-M (mefenoxam), ofurace, and oxadixyl;

III-F.III2 others: hymexazole, octhilinone, oxolinic acid, bupirimate, 5-fluorocytosine, 5-fluoro-2-(p-tolyl-methoxy)pyrimidin-4-amine, and 5-fluoro-2-(4-fluoro-phenyl-methoxy)pyrimidin-4-amine;

III-F.IV Inhibitors of cell division and cytoskeleton

III-F.IV1 tubulin inhibitors from the class of benzimidazoles, and thiophanates: benomyl, carbendazim, fuberidazole, thiabendazole, and thiophanatem-ethyl;

triazolopyrimidines: 5-chloro-7-(4-methylpiperidin-1-yl)-6-(2,4,6-trifluorophenyl)-[1,2,4]triazolo[1,5-a]pyrimidine; and III-F.IV2 other cell division inhibitors: diethofencarb, ethaboxam, pencycuron, fluopicolide, zoxamide, metrafenone, pyriofenone;

III-F.V Inhibitors of amino acid and protein synthesis:
III-F.V1 methionine synthesis inhibitors from the class of anilino-pyrimidines: cyprodinil, mepanipyrim, and pyrimethanil; and
III-F.V2 protein synthesis inhibitors: blasticidin-S, kasugamycin, kasugamycin hydrochloride-hydrate, mildiomycin, streptomycin, oxytetracyclin, polyoxine, and validamycin A;
III-F.VI Signal transduction inhibitors:
III-F.VI1 MAP/histidine kinase inhibitors: fluoroimid, iprodione, procymidone, vinclozolin, fenpiclonil, and fludioxonil; and
III-F.VI2 G protein inhibitors: quinoxyfen;
III-F.VII Lipid and membrane synthesis inhibitors:
F.VII1 Phospholipid biosynthesis inhibitors: edifenphos, iprobenfos, pyrazophos, isoprothiolane;
III-F.VII2 lipid peroxidation: dicloran, quintozene, tecnazene, tolclofos-methyl, biphenyl, chloroneb, and etridiazole;
III-F.VII3 phospholipid biosynthesis and cell wall deposition: dimethomorph, flumorph, mandipropamid, pyrimorph, benthiavalicarb, iprovalicarb, valifenalate, and N-(1-(1-(4-cyano-phenyl)ethanesulfonyl)-but-2-yl) carbamic acid-(4-fluorophenyl) ester;
III-F.VII4 compounds affecting cell membrane permeability and fatty acids: propamocarb; and
III-F.VII5 fatty acid amide hydrolase inhibitors: oxathiapiprolin, 2-{3-[2-(1-{[3,5-bis(difluoromethyl-1H-pyrazol-1-yl]acetyl}piperidin-4-yl)-1,3-thiazol-4-yl]-4,5-dihydro-1,2-oxazol-5-yl}phenyl methanesulfonate, 2-{3-[2-(1-{[3,5-bis(difluoromethyl)-1H-pyrazol-1-yl] acetyl}piperidin-4-yl), and 1,3-thiazol-4-yl]-4,5-dihydro-1,2-oxazol-5-yl}-3-chlorophenyl methanesulfonate;
III-F.VIII Inhibitors with Multi Site Action:
III-F.VIII1 inorganic active substances: Bordeaux mixture, copper acetate, copper hydroxide, copper oxychloride, basic copper sulfate, and sulfur;
III-F.VIII2 thio- and dithiocarbamates: ferbam, mancozeb, maneb, metam, metiram, propineb, thiram, zineb, and ziram;
III-F.VIII3 organochlorine compounds from the class of phthalimides, sulfamides, and chloronitriles: anilazine, chlorothalonil, captafol, captan, folpet, dichlofluanid, dichlorophen, hexachlorobenzene, pentachlorphenole and its salts, phthalide, tolylfluanid, and N-(4-chloro-2-nitro-phenyl)-N-ethyl-4-methyl-benzenesulfonamide; and
III-F.VIII4 guanidines and others: guanidine, dodine, dodine free base, guazatine, guazatine-acetate, iminoctadine, iminoctadine-triacetate, iminoctadine-tris(albesilate), dithianon, and 2,6-dimethyl-1H,5H-[1,4]dithiino[2,3-c:5,6-c'] dipyrrole-1,3,5,7(2H,6H)-tetraone;
III-F.IX Cell wall synthesis inhibitors:
III-F.IX1 inhibitors of glucan synthesis: validamycin, and polyoxin B;
III-F.IX2 melanin synthesis inhibitors: pyroquilon, tricyclazole, carpropamid, dicyclomet, and fenoxanil;
III-F.X Plant defence inducers
III-F.X1 acibenzolar-S-methyl, probenazole, isotianil, tiadinil, prohexadione-calcium;
III-F.X2 phosphonates: fosetyl, fosetyl-aluminum, phosphorous acid and its salts; potassium or sodium bicarbonate; and
III-F.XI Unknown mode of action:
bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, tolprocarb, oxin-copper, proquinazid, tebufloquin, tecloftalam, triazoxide, 2-butoxy-6-iodo-3-propylchromen-4-one, 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-chloro-6-(prop-2-yn-1-yloxy) phenyl]-4,5-dihydro-1,2-oxazol-3-yl}-1,3-thiazol-2-yl) piperidin-1-yl]ethanone, N-(cyclopropylmethoxyimino-(6-difluoro-methoxy-2,3-di-fluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoro-methyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, methoxy-acetic acid 6-tert-butyl-8-fluoro-2,3-dimethyl-quinolin-4-yl ester, 3-[5-(4-methylphenyl)-2,3-dimethyl-isoxazolidin-3-yl]-pyridine, 3-[5-(4-chlorophenyl)-2,3-dimethyl-isoxazolidin-3-yl]-pyridine (pyrisoxazole), N-(6-methoxy-pyridin-3-yl) cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate, picarbutrazox, pentyl N-[6-[[(Z)-[(1-methyltetrazol-5-yl)-phenyl-methylene]amino]oxymethyl]-2-pyridyl] carbamate, 2-[2-[(7,8-difluoro-2-methyl-3-quinolyl) oxy]-6-fluoro-phenyl]propan-2-ol, 2-[2-fluoro-6-[(8-fluoro-2-methyl-3-quinolyl)oxy]phen-yl]propan-2-ol, 3-(5-fluoro-3,3,4,4-tetramethyl-3,4-dihydroisoquinolin-1-yl)quinoline, 3-(4,4-difluoro-3,3-dimethyl-3,4-dihydroisoquinolin-1-yl)quinoline, 3-(4,4,5-trifluoro-3,3-dimethyl-3,4-dihydroisoquinolin-1-yl)quinoline, and 9-fluoro-2,2-dimethyl-5-(3-quinolyl)-3H-1,4-benzoxazepine;
in a synergistically effective amount.

In a further embodiment of the invention there is provided seed, comprising the mixture of the invention in an amount of from 0.1 g to 100 kg per 100 kg of seeds.

The invention provides for a pesticidal composition, comprising a liquid or solid carrier and a novel mixture according to the invention.

The simultaneous (that is joint or separate application of one or more active compound(s) I and one or more compound(s) II and/or III), or successive application (that is immediately one after another and thereby creating the mixture "in-situ" on the desired location, as e.g. the plant, of one or more active compound(s) I and one or more active compound(s) II and/or III) allows enhanced control of pests, in particular Pentatomidae pests, and fungi compared to the control rates that are possible with the individual compounds.

The prior art does not disclose pesticidal mixtures for the control of Pentatomidae pests, particularly stink bugs, comprising such compounds I in combination with the other pesticidically and/or fungicidally active compounds.

The compound I of formula (I) includes its tautomers, racemic mixtures, individual pure enanti-omers and diastereomers and the optically active mixtures.

Preferred as compound I are bilobalide, ginkgolide A and a mixture of bilobalide and ginkgolide A. Further preferred are mixtures comprising bilobalide and/or ginkgolide A and at least one further compound I which is different from bilobalide and ginkgolide A.

In one preferred embodiment compound (I) is bilobalide.

In another preferred embodiment compound (I) is ginkgolide A.

In another preferred embodiment compound (I) is ginkgolide B.

In another preferred embodiment compound (I) is ginkgolide C.

In another preferred embodiment compound (I) is ginkgolide I.

In another preferred embodiment compound (I) is ginkgolide M.

In another preferred embodiment compound (I) is a mixture of bilobalide and ginkgolide A.

In one preferred embodiment compound (I), preferably, bilobalide and/or ginkgolide A, is mixed with one or more pesticidally compounds (II), in particular preferred embodiments thereof, in particular the compounds listed in Table A and the working examples.

In another preferred embodiment compound (I), preferably bilobalide and/or ginkgolide A, is mixed with one or more fungicidally active compounds (III), in particular preferred embodiments thereof, in particular the compounds listed in Table A and the working examples.

In another preferred embodiment compound (I), preferably bilobalide and/or ginkgolide A, is mixed with one or more pesticidally compounds (II), in particular preferred embodiments thereof, in particular the compounds in Table 1 and the working examples, and with one or more fungicidally active compounds (III), in particular preferred embodiments thereof, in particular the compounds listed in Table 1 and the working examples.

Bilobalide and the ginkgolides are known components of the ginkgo tree having the following structures:

a) Bilobalide:

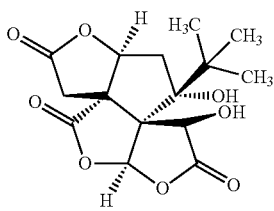

Bilobalide is the common name for (3aS,5aR,8aS,9R,10aR)-9-tert-butyl-8,9-dihydroxydihydro-9H-furo[2,3-b]furo[3',2';2,3]cyclopenta[1,2-c]furan-2,4,7(3H,8H)-trione (CAS 33570-04-6).

b) Ginkgolides:

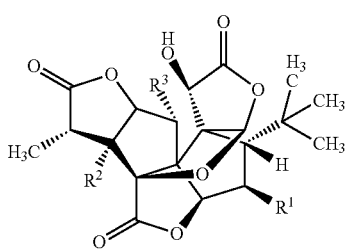

| Ginkgolide | $R^1$ | $R^2$ | $R^3$ | CAS |
|---|---|---|---|---|
| Ginkgolide A | —H | —OH | —H | 15291-75-5 |
| Ginkgolide B | —H | —OH | —OH | 15291-77-7 |
| Ginkgolide C | —OH | —OH | —OH | 15291-76-6 |
| Ginkgolide J | —OH | —OH | —H | 15291-79-9 |
| Ginkgolide M | —OH | —H | —OH | 15291-78-8 |

The above compounds can be used in pure form, as mixtures or in the form of extracts of ginkgo leaves, which may be enriched with the above compounds to a certain degree.

The compounds are commercially available, or can be obtained, preferably from ginkgo leaves by methods known in the art and described e.g. in U.S. Pat. No. 5,700,468, EP-A 360 556, EP-A 0 431 535 and JP-A 09-110713.

Further, the compounds Bilobalide (in enantiopure form), Ginkgolide A (in its racemic form) and Ginkgolide B (in its racemic form) can be obtained by chemical synthesis, as disclosed e.g. in Tetrahedron Letters (1988), 29(28), 3423-6, Tetrahedron Letters (1988), 29(26), 3205-6 and Journal of the American Chemical Society (2000), 122(35), 8453-8463, respectively.

Pesticidal Compounds II

The commercially available compounds of the group M listed above may be found in The Pesticide Manual, 16th Edition, C. MacBean, British Crop Protection Council (2013) among other publications. The online Pesticide Manual is updated regularly and is accessible through http://bcpcdata.com/pesticide-manual.html.

Another online data base for pesticides providing the ISO common names is http://www.alanwood.net/pesticides.

The M.4 neonicotinoid cycloxaprid is known from WO2010/069266 and WO2011/069456, the neonicotinoid M.4A.2, sometimes also to be named as guadipyr, is known from WO2013/003977, and the neonicotinoid M.4A.3 (approved as paichongding in China) is known from WO2007/101369. The metaflumizone analogue M.22B.1 is described in CN10171577 and the analogue M.22B.2 in CN102126994. The phthalamides M.28.1 and M.28.2 are both known from WO2007/101540. The anthranilamide M.28.3 is described in WO2005/077934. The hydra-zide compound M.28.4 is described in WO2007/043677. The anthranilamides M.28.5a) to M.28.5d) and M.28.5h) are described in WO 2007/006670, WO2013/024009 and WO2013/024010, the anthranilamide M.28.5i) is described in WO2011/085575, M.28.5j) in WO2008/134969, M.28.5k) in US2011/046186 and M.28.5l) in WO2012/034403. The diamide compound M.28.6 can be found in WO2012/034472. The spiroketal-substituted cyclic ketoenol derivative M.29.3 is known from WO2006/089633 and the biphenyl-substituted spirocyclic ketoenol derivative M.29.4 from WO2008/067911. The triazoylphenylsulfide M.29.5 is described in WO2006/043635, and biological control agents on the basis of *bacillus* firmus are described in WO2009/124707. The compounds M.29.6a) to M.29.6i) listed under M.29.6 are described in WO2012/029672, and M.29.6j) and M.29.6k) in WO2013/129688. The nematicide M.29.8 is known from WO2013/055584. The isoxazoline M.29.9.a) is described in WO2013/050317. The isoxazoline M.29.9.b) is described in WO2014/126208. The pyridalyl-type analogue M.29.10 is known from WO2010/060379. The carboxamides broflanilide and M.29.11.b) to M.29.11.h) are described in WO2010/018714, and the carboxamides M.29.11 i) to M.29.11.p) in WO2010/127926. The pyridylthiazoles M.29.12.a) to M.29.12.c) are known from WO2010/006713, M.29.12.d) and M.29.12.e) are known from WO2012/000896, and M.29.12.f) to M.29.12.m) from WO2010/129497. The compounds M.29.14a) and M.29.14b) are known from WO2007/101369. The pyrazoles M.29.16.a) to M.29.16h) are described in WO2010/034737, WO2012/084670, and WO2012/143317, respectively, and the pyrazoles M.29.16i) and M.29.16j) are described in U.S. 61/891,437. The pyridinylindazoles M.29.17a) to M.29.17.j) are described in WO2015/038503. The pyridylpyrazoles M.29.18a) to M.29.18d) are described in US2014/0213448. The isoxazoline M.29.19 is described in WO2014/036056. The isoxazoline M.29.20 is known from WO2014/090918.

The biopesticides of group II-L are disclosed further below in the paragraphs about biopesticides II-L).

Fungicidal Compounds III

The fungicides described by common names, their preparation and their activity e.g. against harmful fungi is known (cf.: http://www.alanwood.net/pesticides/); these substances are commercially available.

The fungicides described by IUPAC nomenclature, their preparation and their pesticidal activity is also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303, WO 09/90181, WO 13/007767, WO 13/010862, WO 13/127704, WO 13/024009, WO 13/024010 and WO 13/047441, WO 13/162072, WO 13/092224, WO 11/135833).

Biopesticides

The biopesticides from their preparation and their pesticidal activity e.g. against harmful fungi or insects are known (e-Pesticide Manual V 5.2 (ISBN 978 1 901396 85 0) (2008-2011); http://www.epa.gov/opp00001/biopesticides/, see product lists therein; http://www.omri.org/omri-lists, see lists therein; Bio-Pesticides Database BPDB http://sitem.herts.ac.uk/aeru/bpdb/, see A to Z link therein).

The biopesticides may also have insecticidal, fungicidal, acaricidal, molluscidal, viricidal, bactericidal, pheromone, nematicidal, plant defense activator, plant stress reducing, plant growth regulator, plant growth promoting, plant growth regulator and/or yield enhancing activity.

Many of these biopesticides are registered and/or are commercially available. E.g. *Beauveria bassiana* ATCC 74040 (e.g. in Naturalis® from CBC (Europe) S.r.l., Italy), *B. bassiana* DSM 12256 (US 200020031495; e.g. BioExpert® SC from Live Sytems Technology S.A., Colombia), *B. bassiana* GHA (BotaniGard® 22WGP from Laverlam Int. Corp., USA), and *B. bassiana* PPRI 5339 (ARSEF number 5339 in the USDA ARS collection of entomopathogenic fungal cultures; NRRL 50757) (e.g. BroadBand® from Becker Underwood, South Africa).

PREFERRED EMBODIMENTS

In one preferred embodiment of the method of the invention the at least one pesticidally active compound II is selected from group M consisting of II-M.1 Acetylcholine esterase (AChE) inhibitors from the class of II-M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, di-chlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimi-phosmethyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

II-M.2 GABA-gated chloride channel antagonists such as:

II-M.2A cyclodiene organochlorine compounds, as for example endosulfan or chlordane; or II-M.2B fiproles (phenylpyrazoles), as for example ethiprole, fipronil, flufiprole, pyrafluprole and pyriprole;

M.3 Sodium channel modulators from the class of

M.3A pyrethroids, for example acrinathrin, allethrin, d-cis-trans allethrin, d-trans allethrin, bifenthrin, bioallethrin, bioallethrin S-cylclopentenyl, bioresmethrin, cyprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, heptafluthrin, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

II-M.4 Nicotinic acetylcholine receptor agonists (nAChR) from the class of

II-M.4A neonicotinoids, for example acetamiprid, chlothianidin, cycloxaprid, dinotefuran, imidacloprid, nitenpyram, thiacloprid and thiamethoxam; or the compounds II-M.4A.2: (2E-)-1-[(6-Chloropyridin-3-yl)methyl]-N'-nitro-2-pentylidenehydrazinecarboximidamide; or II-M4A.3: 1-[(6-Chloropyridin-3-yl)methyl]-7-methyl-8-nitro-5-propoxy-1,2,3,5,6,7-hexahydroimidazo[1,2-a]pyridine; or from the class II-M.4B nicotine;

II-M.5 Nicotinic acetylcholine receptor allosteric activators from the class of spinosyns, for example spinosad or spinetoram;

II-M.6 Chloride channel activators from the class of avermectins and milbemycins, for example abamectin, emamectin benzoate, ivermectin, lepimectin or milbemectin;

II-M.7 Juvenile hormone mimics, such as

II-M.7A juvenile hormone analogues as hydroprene, kinoprene and methoprene; or others as II-M.7B fenoxycarb, or II-M.7C pyriproxyfen;

II-M.8 miscellaneous non-specific (multi-site) inhibitors, for example

II-M.8A alkyl halides as methyl bromide and other alkyl halides, or

II-M.8B chloropicrin, or

II-M.8C sulfuryl fluoride, or

II-M.8D borax, or

II-M.8E tartar emetic;

II-M.9 Selective homopteran feeding blockers, for example

II-M.9B pymetrozine, or

II-M.9C flonicamid;

II-M.10 Mite growth inhibitors, including

II-M.10A clofentezine, hexythiazox and diflovidazin, or

II-M.10B etoxazole;

II-M.11 Microbial disruptors of insect midgut membranes, for example *bacillus thuringiensis* or *bacillus sphaericus* and the insecticdal proteins they produce such as *bacillus thuringiensis* subsp. *israelensis, bacillus sphaericus, bacillus thuringiensis* subsp. *aizawai* and *bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

II-M.12 Inhibitors of mitochondrial ATP synthase, for example

II-M.12A diafenthiuron, or

II-M.12B organotin miticides such as azocyclotin, cyhexatin or fenbutatin oxide, or II-M.12C propargite, or II-M.12D tetradifon;

II-M.13 Uncouplers of oxidative phosphorylation via disruption of the proton gradient, for example chlorfenapyr, DNOC or sulfluramid;

II-M.14 Nicotinic acetylcholine receptor (nAChR) channel blockers, for example nereistoxin analogues as bensultap, cartap hydrochloride, thiocyclam orthiosultap sodium;

II-M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

II-M.16 Inhibitors of the chitin biosynthesis type 1, as for example buprofezin;

II-M.17 Moulting disruptors, Dipteran, as for example cyromazine;

II-M.18 Ecdyson receptor agonists such as diacylhydrazines, for example methoxyfenozide, tebufenozide, halofenozide, fufenozide or chromafenozide;

II-M.19 Octopamin receptor agonists, as for example amitraz;

II-M.20 Mitochondrial complex III electron transport inhibitors, for example

II-M.20A hydramethylnon, or

II-M.20B acequinocyl, or

II-M.20C fluacrypyrim;

II-M.21 Mitochondrial complex I electron transport inhibitors, for example

II-M.21A METI acaricides and insecticides such as fenazaquin, fenpyroximate, pyrimidifen, pyridaben, tebufenpyrad or tolfenpyrad, or II-M.21B rotenone;

II-M.22 Voltage-dependent sodium channel blockers, for example

II-M.22A indoxacarb, or

II-M.22B metaflumizone, or

II-M.22B.1: 2-[2-(4-Cyanophenyl)-1-[3-(trifluoromethyl)phenyl]ethylidene]-N-[4-(difluoromethoxy)phenyl]-hydrazinecarboxamide or II-M.22B 0.2: N-(3-Chloro-2-methylphenyl)-2-[(4-chlorophenyl)[4-[methyl(methylsulfonyl)amino]phenyl]methylene]-hydrazinecarboxamide;

II-M.23 Inhibitors of the of acetyl CoA carboxylase, such as tetronic and tetramic acid derivatives, for example spirodiclofen, spiromesifen or spirotetramat;

II-M.24 Mitochondrial complex IV electron transport inhibitors, for example

II-M.24A phosphine such as aluminium phosphide, calcium phosphide, phosphine or zinc phosphide, or II-M.24B cyanide;

II-M.25 Mitochondrial complex II electron transport inhibitors, such as beta-ketonitrile derivatives, for example cyenopyrafen or cyflumetofen;

II-M.28 Ryanodine receptor-modulators from the class of diamides, as for example flubendiamide, chlorantraniliprole (Rynaxypyr®), cyantraniliprole (Cyazypyr®), or the phthalamide compounds II-M.28.1: (R)-3-Chlor-N1-{2-methyl-4-[1,2,2,2-tetrafluor-1-(triflourmethyl)ethyl]phenyl}-N2-(1-methyl-2-methylsulfonylethyl)phthalamid and II-M.28.2: (S)-3-Chlor-N1-{2-methyl-4-[1,2,2,2-tetrafluor-1-(triflourmethyl)ethyl]phenyl}-N2-(1-methyl-2-methylsulfonylethyl)phthalamid, or the compound II-M.28.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound II-M.28.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate;

or a compound selected from M.28.5a) to M.28.5l):

II-M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide;

II-M.28.5b) N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide;

II-M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide;

II-M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide;

II-M.28.5e) N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide;

II-M.28.5f) N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide;

II-M.28.5g) N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide;

II-M.28.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;

II-M.28.5i) N-[2-(5-Amino-1,3,4-thiadiazol-2-yl)-4-chloro-6-methylphenyl]-3-bromo-1-(3-chloro-2-pyridinyl)-1H-pyrazole-5-carboxamide;

II-M.28.5j) 3-Chloro-1-(3-chloro-2-pyridinyl)-N-[2,4-dichloro-6-[[[(1-cyano-1-methylethyl)amino]carbonyl]phenyl]-1H-pyrazole-5-carboxamide;

II-M.28.5k) 3-Bromo-N-[2,4-dichloro-6-(methylcarbamoyl)phenyl]-1-(3,5-dichloro-2-pyridyl)-1H-pyrazole-5-carboxamide;

II-M.28.5l) N-[4-Chloro-2-[[(1,1-dimethylethyl)amino]carbonyl]-6-methylphenyl]-1-(3-chloro-2-pyridinyl)-3-(fluoromethoxy)-1H-pyrazole-5-carboxamide;
or a compound selected from II-M.28.6: N-(2-cyanopropan-2-yl)-N-(2,4-dimethylphenyl)-3-iodobenzene-1,2-dicarboxamide; or II-M.28.7: 3-Chloro-N-(2-cyanopropan-2-yl)-N-(2,4-dimethylphenyl)-benzene-1,2-dicarboxamide;

II-M.28.8a) 1-(3-Chloro-2-pyridinyl)-N-[4-cyano-2-methyl-6-[(methylamino)carbonyl]phenyl]-3-[[5-(trifluoromethyl)-2H-tetrazol-2-yl]methyl]-1H-pyrazole-5-carboxamide (proposed ISO name: tetraniliprole); or II-M.28.8b) 1-(3-Chloro-2-pyridinyl)-N-[4-cyano-2-methyl-6-[(methylamino)carbonyl]phenyl]-3-[[5-(trifluoromethyl)-1H-tetrazol-1-yl]methyl]-1H-pyrazole-5-carboxamide;

II-M.UN Insecticidally active compounds of unknown or uncertain mode of action, as for example afidopyropen, afoxolaner, azadirachtin, amidoflumet, benzoximate, bifenazate, bromopropylate, chinomethionat, cryolite, dicofol, flufenerim, flometoquin, fluensulfone, fluopyram, flupyradifurone, fluralaner, metoxadiazone, piperonyl butoxide, pyflubumide, pyridalyl, pyrifluquinazon, sulfoxaflor, tioxazafen, triflumezopyrim, or the compounds II-M.UN.3: 11-(4-chloro-2,6-dimethylphenyl)-12-hydroxy-1,4-dioxa-9-azadispiro[4.2.4.2]-tetradec-11-en-10-one, or the compound II-M.UN.4: 3-(4'-fluoro-2,4-dimethylbiphenyl-3-yl)-4-hydroxy-8-oxa-1-azaspiro[4.5]dec-3-en-2-one, or the compound II-M.UN.5: 1-[2-fluoro-4-methyl-5-[(2,2,2-trifluoroethyl)sulfinyl]phenyl]-3-(trifluoromethyl)-1H-1,2,4-triazole-5-amine; or a compound selected from the group of M.UN.6, wherein the compound is selected from M.UN.6a) to M.UN.6k):

II-M.UN.6a) (E/Z)—N-[1-[(6-chloro-3-pyridyl)methyl]-2-pyridylidene]-2,2,2-trifluoro-acetamide;

II-M.UN.6b) (E/Z)—N-[1-[(6-chloro-5-fluoro-3-pyridyl)methyl]-2-pyridylidene]-2,2,2-trifluoro-acetamide;

II-M.UN.6c) (E/Z)-2,2,2-trifluoro-N-[1-[(6-fluoro-3-pyridyl)methyl]-2-pyridylidene]acetamide;

II-M.UN.6d) (E/Z)—N-[1-[(6-bromo-3-pyridyl)methyl]-2-pyridylidene]-2,2,2-trifluoro-acetamide;

II-M.UN.6e) (E/Z)—N-[1-[1-(6-chloro-3-pyridyl)ethyl]-2-pyridylidene]-2,2,2-trifluoro-acetamide;

II-M.UN.6f) (E/Z)—N-[1-[(6-chloro-3-pyridyl)methyl]-2-pyridylidene]-2,2-difluoro-acetamide;

II-M.UN.6g) (E/Z)-2-chloro-N-[1-[(6-chloro-3-pyridyl)methyl]-2-pyridylidene]-2,2-difluoro-acetamide;

II-M.UN.6h) (E/Z)—N-[1-[(2-chloropyrimidin-5-yl)methyl]-2-pyridylidene]-2,2,2-trifluoro-acetamide;

II-M.UN.6i) (E/Z)—N-[1-[(6-chloro-3-pyridyl)methyl]-2-pyridylidene]-2,2,3,3,3-pentafluoro-propanamide);

II-M.UN.6j) N-[1-[(6-chloro-3-pyridyl)methyl]-2-pyridylidene]-2,2,2-trifluoro-thioacetamide or of the compound II-M.UN.6k) N-[1-[(6-chloro-3-pyridyl)methyl]-2-pyridylidene]-2,2,2-trifluoro-N'-isopropyl-acetamidine or the compounds II-M.UN.8: 8-chloro-N-[2-chloro-5-methoxyphenyl)sulfonyl]-6-trifluoromethyl)-imidazo[1,2-a]pyridine-2-carboxamide; or II-M.UN.9: 4-[5-(3,5-dichlorophenyl)-5-(trifluoromethyl)-4H-isoxazol-3-yl]-2-methyl-N-(1-oxothietan-3-yl)benzamide; or II-M.UN.10: 5-[3-[2,6-dichloro-4-(3,3-dichloroallyloxy)phenoxy]propoxy]-1H-pyrazole; or a compound selected from the group of M.UN. 12, wherein the compound is selected from M.UN.12a) to M.UN.12m):

II-M.UN.12.a) 2-(1,3-Dioxan-2-yl)-6-[2-(3-pyridinyl)-5-thiazolyl]-pyridine;

II-M.UN.12.b) 2-[6-[2-(5-Fluoro-3-pyridinyl)-5-thiazolyl]-2-pyridinyl]-pyrimidine;

II-M.UN.12.c) 2-[6-[2-(3-Pyridinyl)-5-thiazolyl]-2-pyridinyl]-pyrimidine;

II-M.UN.12.d) N-Methylsulfonyl-6-[2-(3-pyridyl)thiazol-5-yl]pyridine-2-carboxamide II-M.UN.12.e) N-Methylsulfonyl-6-[2-(3-pyridyl)thiazol-5-yl]pyridine-2-carboxamide II-M.UN.12.f) N-Ethyl-N-[4-methyl-2-(3-pyridyl)thiazol-5-yl]-3-methylthio-propanamide II-M.UN.12.g) N-Methyl-N-[4-methyl-2-(3-pyridyl)thiazol-5-yl]-3-methylthio-propanamide II-M.UN.12.h) N,2-Dimethyl-N-[4-methyl-2-(3-pyridyl)thiazol-5-yl]-3-methylthio-propanamide II-M.UN.12.i) N-Ethyl-2-methyl-N-[4-methyl-2-(3-pyridyl)thiazol-5-yl]-3-methylthio-propanamide II-M.UN.12.j) N-[4-Chloro-2-(3-pyridyl)thiazol-5-yl]-N-ethyl-2-methyl-3-methylthio-propanamide II-M.UN.12.k) N-[4-Chloro-2-(3-pyridyl)thiazol-5-yl]-N,2-dimethyl-3-methylthio-propanamide II-M.UN. 12.1) N-[4-Chloro-2-(3-pyridyl)thiazol-5-yl]-N-methyl-3-methylthio-propanamide II-M.UN.12.m) N-[4-Chloro-2-(3-pyridyl)thiazol-5-yl]-N-ethyl-3-methylthio-propanamide; or the compound II-M.UN.13: 2-(4-methoxyiminocyclohexyl)-2-(3,3,3-trifluoropropylsulfonyl)acetonitrile; or the compounds II-M.UN.14a) 1-[(6-Chloro-3-pyridinyl)methyl]-1,2,3,5,6,7-hexahydro-5-methoxy-7-methyl-8-nitro-imidazo[1,2-a]pyridine; or II-M.UN.14b) 1-[(6-Chloropyridin-3-yl)methyl]-7-methyl-8-nitro-1,2,3,5,6,7-hexahydroimidazo[1,2-a]pyridin-5-ol; or the compound II-M.UN.15: 1-[(2-Chloro-1,3-thiazol-5-yl)methyl]-3-(3,5-dichlorophenyl)-9-methyl-4-oxo-4H-pyrido[1,2-a]pyrimidin-1-ium-2-olate; or II-M.BP Biopesticides, being pesticidal compounds of biological origin with insecticidal, acaricidal, molluscidal and/or nematicidal activity, including II-M.BP-1: Microbial pesticides: *Bacillus firmus, B. thuringiensis* ssp. *israelensis*, B. t. ssp. *galleriae*, B. t. ssp. *kurstaki, Beauveria bassiana, Burkholderia* sp., *Chromobacterium subtsugae, Cydia pomonella granulosis virus, Isaria fumosorosea, Lecanicillium longisporum, L. muscarium* (formerly *Verticillium lecanii*), *Metarhizium anisopliae, M. anisopliae* var. *acridum, Paecilomyces fumosoroseus, P. lilacinus, Paenibacillus poppiliae, Pasteuria* spp., *P. nishizawae, P. reneformis, P. usagae, Pseudomonas fluorescens, Steinernema feltiae, Streptomces galbus*; or II-M.BP-2: Biochemical pesticides: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, Acacia negra extract, extract of grapefruit seeds and pulp, extract of Chenopodium ambrosiodae, Catnip oil, Neem oil, Quillay extract, Tagetes oil, and/or the at least one fungicidally active compound III is selected from group F consisting of:

F.I) Respiration inhibitors

F.I 1) Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, mandestrobine, meto-minostrobin, orysastrobin, picoxystrobin, pyraclostrobin, pyrametostrobin, pyraoxystrobin, trifloxystrobin and 2-(2-(3-(2,6-dichlorophenyl)-1-methyl-allylidene-aminooxymethyl)-phenyl)-2-methoxyimino-N-methyl-acetamide, pyribencarb, triclopyricarb/chlorodincarb, famoxadone, fenamidone;

F.I 2) inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-meth-oxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;

F.I 3) inhibitors of complex II (e. g. carboxamides): benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, N-(7-fluoro-1,1,3-trimethyl-indan-4-yl)-1,3-dimethyl-pyrazole-4-carboxamide, N-[2-(2,4-dichlorophenyl)-2-methoxy-1-methyl-ethyl]-3-(difluoromethyl)-1-methyl-pyrazole-4-carboxamide, N-[2-(2,4-difluorophenyl)phenyl]-3-(trifluoromethyl)pyrazine-2-carboxamide;

F.I 4) other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

F.II) Sterol biosynthesis inhibitors (SBI fungicides)

F.II 1) C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thiocyanato-1H-[1,2,4]triazole, 2-[rel-(2S;3R)-3-(2-chlorophenyl)-2-(2,4-difluorophenyl)-oxiranylmethyl]-2H-[1,2,4]triazole-3-thiol, 2-[2-chloro-4-(4-chlorophenoxy)phenyl]-1-(1,2,4-triazol-1-yl)pentan-2-ol, 1-[4-(4-chlorophenoxy)-2-(trifluoromethyl)phenyl]-1-cyclopropyl-2-(1,2,4-triazol-1-yl)ethanol, 2-[4-(4-chlorophenoxy)-2-(trifluorometh-yl)phenyl]-1-(1,2,4-triazol-1-yl)butan-2-ol, 2-[2-chloro-4-(4-chlorophenoxy)phenyl]-1-(1,2,4-triazol-1-yl)butan-2-ol, 2-[4-(4-chlorophenoxy)-2-(trifluoromethyl)phenyl]-3-methyl-1-(1,2,4-triazol-1-yl)butan-2-ol, 2-[4-(4-chlorophenoxy)-2-(trifluoromethyl)-phenyl]-1-(1,2,4-triazol-1-yl)propan-2-ol, 2-[2-chloro-4-(4-chlorophenoxy)phenyl]-3-methyl-1-(1,2,4-triazol-1-yl)butan-2-ol, 2-[4-(4-chlorophenoxy)-2-(trifluoromethyl)-phenyl]-1-(1,2,4-triazol-1-yl)pentan-2-ol, 2-[4-(4-fluorophenoxy)-2-(trifluoromethyl)-phenyl]-1-(1,2,4-triazol-1-yl)propan-2-ol; imidazoles: imazalil, pefurazoate, prochloraz, triflumizol; pyrimidines, pyridines and piperazines: fenarimol, nuarimol, pyrifenox, triforine, [3-(4-chloro-2-fluoro-phenyl)-5-(2,4-difluorophenyl)isoxazol-4-yl]-(3-pyridyl)methanol;

F.II 2) Delta14-reductase inhibitors: aldimorph, dodemorph, dodemorph-acetate, fenpropimorph, tridemorph, fenpropidin, piperalin, spiroxamine;

F.II 3) Inhibitors of 3-keto reductase: fenhexamid;

F.III) Nucleic acid synthesis inhibitors

F.III 1) phenylamides oracyl amino acid fungicides: benalaxyl, benalaxyl-M, kiralaxyl, metalaxyl, metalaxyl-M (mefenoxam), ofurace, oxadixyl;

F.III 2) others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy)pyrimidin-4-amine;

F.IV) Inhibitors of cell division and cytoskeleton

F.IV 1) tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine;

F.IV 2) other cell division inhibitors: diethofencarb, ethaboxam, pencycuron, fluopicolide, zoxamide, metrafenone, pyriofenone;

F.V) Inhibitors of amino acid and protein synthesis

F.V 1) methionine synthesis inhibitors (anilino-pyrimidines): cyprodinil, mepanipyrim, pyrimethanil;

F.V 2) protein synthesis inhibitors: blasticidin-S, kasugamycin, kasugamycin hydrochloride-hydrate, mildiomycin, streptomycin, oxytetracyclin, polyoxine, validamycin A;

F.VI) Signal transduction inhibitors

F.VI 1) MAP/histidine kinase inhibitors: fluoroimid, iprodione, procymidone, vinclozolin, fenpiclonil, fludioxonil;

F.VI 2) G protein inhibitors: quinoxyfen;

F.VII) Lipid and membrane synthesis inhibitors

F.VII 1) Phospholipid biosynthesis inhibitors: edifenphos, iprobenfos, pyrazophos, isoprothiolane;

F.VII 2) lipid peroxidation: dicloran, quintozene, tecnazene, tolclofos-methyl, biphenyl, chloroneb, etridiazole;

F.VII 3) phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl) carbamic acid-(4-fluorophenyl) ester;

F.VII 4) compounds affecting cell membrane permeability and fatty acids: propamocarb, propamocarb-hydrochlorid;

F.VII 5) fatty acid amide hydrolase inhibitors: oxathiapiprolin;

F.VIII) Inhibitors with Multi Site Action

F.VIII 1) inorganic active substances: Bordeaux mixture, copper acetate, copper hydroxide, copper oxychloride, basic copper sulfate, sulfur;

F.VIII 2) thio- and dithiocarbamates: ferbam, mancozeb, maneb, metam, metiram, propineb, thiram, zineb, ziram;

F.VIII 3) organochlorine compounds (e.g. phthalimides, sulfamides, chloronitriles): anilazine, chlorothalonil, captafol, captan, folpet, dichlofluanid, dichlorophen, hexachlorobenzene, pentachlorphenole and its salts, phthalide, tolylfluanid, N-(4-chloro-2-nitro-phenyl)-N-ethyl-4-methyl-benzenesulfonamide;

F.VIII 4) guanidines and others: guanidine, dodine, dodine free base, guazatine, guazatine-acetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)-tetraone;

F.IX) Cell wall synthesis inhibitors

F.IX 1) inhibitors of glucan synthesis: validamycin, polyoxin B;

F.IX 2) melanin synthesis inhibitors: pyroquilon, tricyclazole, carpropamid, dicyclomet, fenoxanil;

F.X) Plant defence inducers

F.X 1) acibenzolar-S-methyl, probenazole, isotianil, tiadinil, prohexadione-calcium;

F.X 2) phosphonates: fosetyl, fosetyl-aluminum, phosphorous acid and its salts, 4-cyclopropyl-N-(2,4-dimethoxy-phenyl)thiadiazole-5-carboxamide;

F.XI) Unknown mode of action bronopol, chinomethionat, cyflufenamid, cymoxanil, dazomet, debacarb, diclomezine, difenoquat, difenoquat-methylsulfate, diphenylamin, fenpyrazamine, flumetover, flusulfamide, flutianil, methasulfocarb, nitrapyrin, nitrothal-isopropyl, oxathiapiprolin, picarbutrazox, tolprocarb, 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, methoxy-acetic acid 6-tert-butyl-8-fluoro-2,3-dimethyl-quinolin-4-yl ester, 3-[5-(4-methylphenyl)-2,3-dimethyl-isoxazolidin-3-yl]-pyridine, 3-[5-(4-chlorophenyl)-2,3-dimethyl-isoxazolidin-3-yl]-pyridine (pyrisoxazole), N-(6-methoxy-pyridin-3-yl) cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate, pentyl N-[6-[[(Z)-[(1-methyltetrazol-5-yl)-phenyl-methylene]amino]oxymethyl]-2-pyridyl]carbamate, 2-[2-[(7,8-difluoro-2-methyl-3-quinolyl)oxy]-6-fluoro-phenyl]propan-2-ol, 2-[2-fluoro-6-[(8-fluoro-2-methyl-3-quinolyl)oxy]phenyl]propan-2-ol, 3-(5-fluoro-3,3,4,4-tetramethyl-3,4-dihydroisoquinolin-1-yl)quinoline, 3-(4,4-difluoro-3,3-dimethyl-3,4-dihydroisoquinolin-1-yl)quinoline, 3-(4,4,5-trifluoro-3,3-dimethyl-3,4-dihydroisoquinolin-1-yl)quinoline;

F.XII) Biopesticides

F.XII 1) Microbial pesticides with fungicidal, bactericidal, viricidal and/or plant defense activator activity: *Ampelomyces quisqualis, Aspergillus flavus, Aureobasidium pullulans, Bacillus amyloliquefaciens, B. mojavensis, B. simplex, B. solisalsi, B. subtilis, B. subtilis* var. *amyloliquefaciens, Candida oleophila, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea* f. *catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus polymyxa, Pantoea vagans, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. violaceusniger, Talaromyces flavus, Trichoderma atroviride, T. fertile, T. gamsii, T. harmatum, T. harzianum*; mixture of *T. harzianum* and *T. viride*; mixture of *T. polysporum* and *T. harzianum; T. stromaticum, T. virens* (also named *Gliocladium virens*), *T. viride, Typhula phacorrhiza, Uloccladium oudemansii, Verticillium dahlia*, zucchini yellow mosaic virus (avirulent strain);

F.XII 2) Biochemical pesticides with fungicidal, bactericidal, viricidal and/or plant defense activator activity: chitosan (hydrolysate), harpin protein, laminarin, Menhaden fish oil, natamycin, Plum pox virus coat protein, potassium or sodium bicarbonate, *Reynoutria sachlinensis* extract, salicylic acid, tea tree oil In one preferred embodiment of the mixtures of the invention compounds II and/or III are selected from:

II-M.1 Acetylcholine esterase (AChE) inhibitors from the class of

II-M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of II-M.2 GABA-gated chloride channel antagonists such as:

II-M.2A cyclodiene organochlorine compounds, as for example endosulfan or chlordane; or II-M.2B fiproles (phenylpyrazoles), as for example ethiprole, fipronil, flufiprole, pyrafluprole and pyriprole;

II-M.3 Sodium channel modulators selected from sodium channel modulators such as DDT or methoxychlor;
II-M.4 Nicotinic acetylcholine receptor agonists (nAChR) from the class of
II-M.4A neonicotinoids, for example acetamiprid, chlothianidin, cycloxaprid, dinotefuran, imidacloprid, nitenpyram, thiacloprid and thiamethoxam; or the compounds
II-M.4A.2: (2E-)-1-[(6-Chloropyridin-3-yl)methyl]-N'-nitro-2-pentylidenehydrazinecarboximidamide; or
II-M4A.3: 1-[(6-Chloropyridin-3-yl)methyl]-7-methyl-8-nitro-5-propoxy-1,2,3,5,6,7-hexahydroimidazo[1,2-a]pyridine; or from the class
II-M.4B nicotine;
II-M.5 Nicotinic acetylcholine receptor allosteric activators from the class of spinosyns, for example spinosad or spinetoram;
II-M.6 Chloride channel activators from the class of avermectins and milbemycins, for example abamectin, emamectin benzoate, ivermectin, lepimectin or milbemectin;
II-M.7 Juvenile hormone mimics, such as
II-M.7A juvenile hormone analogues as hydroprene, kinoprene and methoprene; or others as
II-M.7B fenoxycarb, or
II-M.7C pyriproxyfen;
II-M.8 miscellaneous non-specific (multi-site) inhibitors, for example
II-M.8A alkyl halides as methyl bromide and other alkyl halides, or
II-M.8B chloropicrin, or
II-M.8C sulfuryl fluoride, or
II-M.8D borax, or
II-M.8E tartar emetic;
II-M.9 Selective homopteran feeding blockers, for example
II-M.9B pymetrozine, or
II-M.9C flonicamid;
II-M.10 Mite growth inhibitors, including
II-M.10A clofentezine, hexythiazox and diflovidazin, or
II-M.10B etoxazole;
II-M.11 Microbial disruptors of insect midgut membranes, for example *bacillus thuringiensis* or *bacillus sphaericus* and the insecticdal proteins they produce such as *bacillus thuringiensis* subsp. *israelensis, bacillus sphaericus, bacillus thuringiensis* subsp. *aizawai, bacillus thuringiensis* subsp. *kurstaki* and *bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;
II-M.12 Inhibitors of mitochondrial ATP synthase, for example
II-M.12A diafenthiuron, or
II-M.12B organotin miticides such as azocyclotin, cyhexatin or fenbutatin oxide, or
II-M.12C propargite, or
II-M.12D tetradifon;
II-M.13 Uncouplers of oxidative phosphorylation via disruption of the proton gradient, for example chlorfenapyr, DNOC or sulfluramid;
II-M.14 Nicotinic acetylcholine receptor (nAChR) channel blockers, for example nereistoxin analogues as bensultap, cartap hydrochloride, thiocyclam orthiosultap sodium;
II-M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;
II-M.16 Inhibitors of the chitin biosynthesis type 1, as for example buprofezin;
II-M.17 Moulting disruptors, Dipteran, as for example cyromazine;
II-M.18 Ecdyson receptor agonists such as diacylhydrazines, for example methoxyfenozide, tebufenozide, halofenozide, fufenozide or chromafenozide;
II-M.19 Octopamin receptor agonists, as for example amitraz;
II-M.20 Mitochondrial complex III electron transport inhibitors, for example
II-M.20A hydramethylnon, or
II-M.20B acequinocyl, or
II-M.20C fluacrypyrim;
II-M.21 Mitochondrial complex I electron transport inhibitors, for example
II-M.21A METI acaricides and insecticides such as fenazaquin, fenpyroximate, pyrimidifen, pyridaben, tebufenpyrad or tolfenpyrad, or
II-M.21B rotenone;
II-M.22 Voltage-dependent sodium channel blockers, for example
II-M.22A indoxacarb, or
II-M.22B metaflumizone, or
II-M.22B.1: 2-[2-(4-Cyanophenyl)-1-[3-(trifluoromethyl)phenyl]ethylidene]-N-[4-(difluoromethoxy)phenyl]-hydrazinecarboxamide or
II-M.22B 0.2: N-(3-Chloro-2-methylphenyl)-2-[(4-chlorophenyl)[4-[methyl(methylsulfonyl)amino]phenyl]methylene]-hydrazinecarboxamide;
II-M.23 Inhibitors of the of acetyl CoA carboxylase, such as tetronic and tetramic acid derivatives, for example spirodiclofen, spiromesifen or spirotetramat;
II-M.24 Mitochondrial complex IV electron transport inhibitors, for example
II-M.24A phosphine such as aluminium phosphide, calcium phosphide, phosphine or zinc phosphide, or
II-M.24B cyanide;
II-M.25 Mitochondrial complex II electron transport inhibitors, such as beta-ketonitrile derivatives, for example cyenopyrafen or cyflumetofen;
II-M.28 Ryanodine receptor-modulators from the class of diamides, as for example flubendiamide, chlorantraniliprole (Rynaxypyr®), cyantraniliprole (Cyazypyr®), or the phthalamide compounds
II-M.28.1: (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and
II-M.28.2: (S)-3-Chlor-N1-{2-methyl-4-[1,2,2,2-tetrafluor-1-(trifluormethyl)ethyl]phenyl}-N2-(1-methyl-2-methylsulfonylethyl)phthalamid, or the compound
II-M.28.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound
II-M.28.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate; or a compound selected from M.28.5a) to M.28.5l):
II-M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide;
II-M.28.5b) N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide;
II-M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide;

II-M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide;

II-M.28.5e) N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide;

II-M.28.5f) N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide;

II-M.28.5g) N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide;

II-M.28.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;

II-M.28.5i) N-[2-(5-Amino-1,3,4-thiadiazol-2-yl)-4-chloro-6-methylphenyl]-3-bromo-1-(3-chloro-2-pyridinyl)-1H-pyrazole-5-carboxamide;

II-M.28.5j) 3-Chloro-1-(3-chloro-2-pyridinyl)-N-[2,4-dichloro-6-[[(1-cyano-1-methylethyl)amino]carbonyl]phenyl]-1H-pyrazole-5-carboxamide;

II-M.28.5k) 3-Bromo-N-[2,4-dichloro-6-(methylcarbamoyl)phenyl]-1-(3,5-dichloro-2-pyridyl)-1H-pyrazole-5-carboxamide;

II-M.28.5l) N-[4-Chloro-2-[[(1,1-dimethylethyl)amino]carbonyl]-6-methylphenyl]-1-(3-chloro-2-pyridinyl)-3-(fluoromethoxy)-1H-pyrazole-5-carboxamide; or a compound selected from II-M.28.6: N-(2-cyanopropan-2-yl)-N-(2,4-dimethylphenyl)-3-iodobenzene-1,2-dicarboxamide; or II-M.28.7: 3-Chloro-N-(2-cyanopropan-2-yl)-N-(2,4-dimethylphenyl)-benzene-1,2-dicarboxamide;

II-M.28.8a) 1-(3-Chloro-2-pyridinyl)-N-[4-cyano-2-methyl-6-[(methylamino)carbonyl]phenyl]-3-[[5-(trifluoromethyl)-2H-tetrazol-2-yl]methyl]-1H-pyrazole-5-carboxamide; or II-M.28.8b) 1-(3-Chloro-2-pyridinyl)-N-[4-cyano-2-methyl-6-[(methylamino)carbonyl]phenyl]-3-[[5-(trifluoromethyl)-1H-tetrazol-1-yl]methyl]-1H-pyrazole-5-carboxamide;

II-M.UN Insecticidally active compounds of unknown or uncertain mode of action, as for example afidopyropen, afoxolaner, azadirachtin, amidoflumet, benzoximate, bifenazate, bromopropylate, chinomethionat, cryolite, dicofol, flufenerim, flometoquin, fluensulfone, fluopyram, flupyradifurone, fluralaner, metoxadiazone, piperonyl butoxide, pyflubumide, pyridalyl, pyrifluquinazon, sulfoxaflor, tioxazafen, triflumezopyrim, or the compounds II-M.UN.3: 11-(4-chloro-2,6-dimethylphenyl)-12-hydroxy-1,4-dioxa-9-azadispiro[4.2.4.2]-tetradec-11-en-10-one, or the compound II-M.UN.4: 3-(4'-fluoro-2,4-dimethylbiphenyl-3-yl)-4-hydroxy-8-oxa-1-azaspiro[4.5]dec-3-en-2-one, or the compound II-M.UN.5: 1-[2-fluoro-4-methyl-5-[(2,2,2-trifluoroethyl)sulfinyl]phenyl]-3-(trifluoromethyl)-1H-1,2,4-triazole-5-amine; or a compound selected from the group of M.UN.6, wherein the compound is selected from II-II-M.UN.6a) to M.UN.6k):

II-M.UN.6a) (E/Z)—N-[1-[(6-chloro-3-pyridyl)methyl]-2-pyridylidene]-2,2,2-trifluoro-acetamide;

II-M.UN.6b) (E/Z)—N-[1-[(6-chloro-5-fluoro-3-pyridyl)methyl]-2-pyridylidene]-2,2,2-trifluoro-acetamide;

II-M.UN.6c) (E/Z)-2,2,2-trifluoro-N-[1-[(6-fluoro-3-pyridyl)methyl]-2-pyridylidene]acetamide;

II-M.UN.6d) (E/Z)—N-[1-[(6-bromo-3-pyridyl)methyl]-2-pyridylidene]-2,2,2-trifluoro-acetamide;

II-M.UN.6e) (E/Z)—N-[1-[1-(6-chloro-3-pyridyl)ethyl]-2-pyridylidene]-2,2,2-trifluoro-acetamide;

II-M.UN.6f) (E/Z)—N-[1-[(6-chloro-3-pyridyl)methyl]-2-pyridylidene]-2,2-difluoro-acetamide;

II-M.UN.6g) (E/Z)-2-chloro-N-[1-[(6-chloro-3-pyridyl)methyl]-2-pyridylidene]-2,2-difluoro-acetamide;

II-M.UN.6h) (E/Z)—N-[1-[(2-chloropyrimidin-5-yl)methyl]-2-pyridylidene]-2,2,2-trifluoro-acetamide;

II-M.UN.6i) (E/Z)—N-[1-[(6-chloro-3-pyridyl)methyl]-2-pyridylidene]-2,2,3,3,3-pentafluoro-propanamide);

II-M.UN.6j) N-[1-[(6-chloro-3-pyridyl)methyl]-2-pyridylidene]-2,2,2-trifluoro-thioacetamide or of the compound II-M.UN.6k) N-[1-[(6-chloro-3-pyridyl)methyl]-2-pyridylidene]-2,2,2-trifluoro-N'-isopropyl-acetamidine or the compounds II-M.UN.8: 8-chloro-N-[2-chloro-5-methoxyphenyl)sulfonyl]-6-trifluoromethyl)-imidazo[1,2-a]pyridine-2-carboxamide; or II-M.UN.9: 4-[5-(3,5-dichlorophenyl)-5-(trifluoromethyl)-4H-isoxazol-3-yl]-2-methyl-N-(1-oxothietan-3-yl)benzamide; or II-M.UN.10: 5-[3-[2,6-dichloro-4-(3,3-dichloroallyloxy)phenoxy]propoxy]-1H-pyrazole; or a compound selected from the group of M.UN. 12, wherein the compound is selected from M.UN.12a) to M.UN.12m):

II-M.UN.12.a) 2-(1,3-Dioxan-2-yl)-6-[2-(3-pyridinyl)-5-thiazolyl]-pyridine;

II-M.UN.12.b) 2-[6-[2-(5-Fluoro-3-pyridinyl)-5-thiazolyl]-2-pyridinyl]-pyrimidine;

II-M.UN.12.c) 2-[6-[2-(3-Pyridinyl)-5-thiazolyl]-2-pyridinyl]-pyrimidine;

II-M.UN.12.d) N-Methylsulfonyl-6-[2-(3-pyridyl)thiazol-5-yl]pyridine-2-carboxamide II-M.UN.12.e) N-Methylsulfonyl-6-[2-(3-pyridyl)thiazol-5-yl]pyridine-2-carboxamide II-M.UN.12.f) N-Ethyl-N-[4-methyl-2-(3-pyridyl)thiazol-5-yl]-3-methylthio-propanamide II-M.UN.12.g) N-Methyl-N-[4-methyl-2-(3-pyridyl)thiazol-5-yl]-3-methylthio-propanamide II-M.UN.12.h) N,2-Dimethyl-N-[4-methyl-2-(3-pyridyl)thiazol-5-yl]-3-methylthio-propanamide II-M.UN.12.i) N-Ethyl-2-methyl-N-[4-methyl-2-(3-pyridyl)thiazol-5-yl]-3-methylthio-propanamide II-M.UN 0.12.j) N-[4-Chloro-2-(3-pyridyl)thiazol-5-yl]-N-ethyl-2-methyl-3-methylthio-propanamide II-M.UN.12.k) N-[4-Chloro-2-(3-pyridyl)thiazol-5-yl]-N,2-dimethyl-3-methylthio-propanamide II-M.UN.12.l) N-[4-Chloro-2-(3-pyridyl)thiazol-5-yl]-N-methyl-3-methylthio-propanamide II-M.UN.12.m) N-[4-Chloro-2-(3-pyridyl)thiazol-5-yl]-N-ethyl-3-methylthio-propanamide; or the compound II-M.UN.13: 2-(4-methoxyiminocyclohexyl)-2-(3,3,3-trifluoropropylsulfonyl)acetonitrile; or the compounds II-M.UN.14a) 1-[(6-Chloro-3-pyridinyl)methyl]-1,2,3,5,6,7-hexahydro-5-methoxy-7-methyl-8-nitro-imidazo[1,2-a]pyridine; or II-M.UN.14b) 1-[(6-Chloropyridin-3-yl)methyl]-7-methyl-8-nitro-1,2,3,5,6,7-hexahydroimidazo[1,2-a]pyridin-5-ol; or the compound II-M.UN.15:1-[(2-Chloro-1,3-thiazol-5-yl)methyl]-3-(3,5-dichlorophenyl)-9-methyl-4-oxo-4H-pyrido[1,2-a]pyrimidin-1-ium-2-olate; or II-M.BP Biopesticides, being pesticidal compounds of biological origin with insecticidal, acaricidal, molluscidal and/or nematicidal activity, including II-M.BP-1: Microbial pesticides: *Bacillus firmus, B. thuringiensis* ssp. *israelensis*, B. t. ssp. *galleriae*, B. t. ssp. *kurstaki, Beauveria bassiana, Burkholderia* sp., *Chromobacterium subtsugae, Cydia pomonella* granulosis virus, *Isaria fumosorosea*, Lecanicillium *longisporum*, *L. muscarium* (formerly *Verticillium* lecanii), *Metarhizium anisopliae, M. anisopliae* var. *acridum, Paecilomyces* fumosoroseus, *P. lilacinus, Paenibacillus* poppiliae, *Pasteuria* spp., *P. nishizawae, P. reneformis, P. usagae, Pseudomonas fluorescens, Steinernema feltiae*, Streptomces *galbus*; or II-M.BP-2: Biochemical pesticides: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, Acacia negra extract, extract of grapefruit seeds and pulp, extract of *Chenopodium* ambrosiodae, Catnip oil, Neem oil, Quillay extract, *Tagetes* oil, and/or F.I) Respiration inhibitors F.I 1) Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, mandestrobine, meto-minostrobin, orysastrobin, picoxystrobin, pyraclostrobin, pyrametostrobin, pyraoxystrobin, trifloxystrobin and 2-(2-(3-(2,6-dichlorophenyl)-1-methyl-allylidene-aminooxymethyl)-phenyl)-2-methoxyimino-N-methyl-acetamide, pyribencarb, triclopyricarb/chlorodincarb, famoxadone, fenamidone;

F.I 2) inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-meth-oxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;

F.I 3) inhibitors of complex II (e. g. carboxamides): benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl) pyrazole-4-carboxamide, 1,3,5-trimethyl-N-(1,1,3-trimethylindan-4-yl)pyrazole-4-carboxamide, N-(7-fluoro-1,1,3-trimethyl-indan-4-yl)-1,3-dimethyl-pyrazole-4-carboxamide, N-[2-(2,4-dichlorophenyl)-2-methoxy-1-methyl-ethyl]-3-(difluoromethyl)-1-methyl-pyrazole-4-carboxamide, N-[2-(2,4-difluorophenyl) phenyl]-3-(trifluoromethyl)pyrazine-2-carboxamide;

F.I 4) other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

F.II) Sterol biosynthesis inhibitors (SBI fungicides)

F.II 1) C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thiocyanato-1H-[1,2,4]triazole, 2-[rel-(2S;3R)-3-(2-chlorophenyl)-2-(2,4-difluorophenyl)-oxiranylmethyl]-2H-[1,2,4]triazole-3-thiol, 2-[2-chloro-4-(4-chlorophenoxy)phenyl]-1-(1,2,4-triazol-1-yl) pentan-2-ol, 1-[4-(4-chlorophenoxy)-2-(trifluoromethyl) phenyl]-1-cyclopropyl-2-(1,2,4-triazol-1-yl)ethanol, 2-[4-(4-chlorophenoxy)-2-(trifluorometh-yl)phenyl]-1-(1,2,4-triazol-1-yl)butan-2-ol, 2-[2-chloro-4-(4-chlorophenoxy)phenyl]-1-(1,2,4-triazol-1-yl)butan-2-ol, 2-[4-(4-chlorophenoxy)-2-(trifluoromethyl)phenyl]-3-methyl-1-(1,2,4-triazol-1-yl)butan-2-ol, 2-[4-(4-chlorophenoxy)-2-(trifluoromethyl)-phenyl]-1-(1,2,4-triazol-1-yl)propan-2-ol, 2-[2-chloro-4-(4-chlorophenoxy)phenyl]-3-methyl-1-(1,2,4-triazol-1-yl)butan-2-ol, 2-[4-(4-chlorophenoxy)-2-(trifluoromethyl)-phenyl]-1-(1,2,4-triazol-1-yl)pentan-2-ol, 2-[4-(4-fluorophenoxy)-2-(trifluoromethyl)-phenyl]-1-(1,2,4-triazol-1-yl)propan-2-ol; imidazoles: imazalil, pefurazoate, prochloraz, triflumizol; pyrimidines, pyridines and piperazines: fenarimol, nuarimol, pyrifenox, triforine, [3-(4-chloro-2-fluoro-phenyl)-5-(2,4-difluorophenyl)isoxazol-4-yl]-(3-pyridyl)methanol;

F.II 2) Delta14-reductase inhibitors: aldimorph, dodemorph, dodemorph-acetate, fenpropimorph, tridemorph, fenpropidin, piperalin, spiroxamine;

F.II 3) Inhibitors of 3-keto reductase: fenhexamid;

F.III) Nucleic acid synthesis inhibitors

F.III 1) phenylamides oracyl amino acid fungicides: benalaxyl, benalaxyl-M, kiralaxyl, metalaxyl, metalaxyl-M (mefenoxam), ofurace, oxadixyl;

F.III 2) others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy)pyrimidin-4-amine;

F.IV) Inhibitors of cell division and cytoskeleton

F.IV 1) tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine;

F.IV 2) other cell division inhibitors: diethofencarb, ethaboxam, pencycuron, fluopicolide, zoxamide, metrafenone, pyriofenone;

F.V) Inhibitors of amino acid and protein synthesis

F.V 1) methionine synthesis inhibitors (anilino-pyrimidines): cyprodinil, mepanipyrim, pyrimethanil;

F.V 2) protein synthesis inhibitors: blasticidin-S, kasugamycin, kasugamycin hydrochloride-hydrate, mildiomycin, streptomycin, oxytetracyclin, polyoxine, validamycin A;

F.VI) Signal transduction inhibitors

F.VI 1) MAP/histidine kinase inhibitors: fluoroimid, iprodione, procymidone, vinclozolin, fenpiclonil, fludioxonil;

F.VI 2) G protein inhibitors: quinoxyfen;

F.VII) Lipid and membrane synthesis inhibitors

F.VII 1) Phospholipid biosynthesis inhibitors: edifenphos, iprobenfos, pyrazophos, isoprothiolane;

F.VII 2) lipid peroxidation: dicloran, quintozene, tecnazene, tolclofos-methyl, biphenyl, chloroneb, etridiazole;

F.VII 3) phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl) carbamic acid-(4-fluorophenyl) ester;

F.VII 4) compounds affecting cell membrane permeability and fatty acids: propamocarb, propamocarb-hydrochlorid;

F.VII 5) fatty acid amide hydrolase inhibitors: oxathiapiprolin;

F.VIII) Inhibitors with Multi Site Action

F.VIII 1) inorganic active substances: Bordeaux mixture, copper acetate, copper hydroxide, copper oxychloride, basic copper sulfate, sulfur;

F.VIII 2) thio- and dithiocarbamates: ferbam, mancozeb, maneb, metam, metiram, propineb, thiram, zineb, ziram;

F.VIII 3) organochlorine compounds (e.g. phthalimides, sulfamides, chloronitriles): anilazine, chlorothalonil, captafol, captan, folpet, dichlofluanid, dichlorophen, hexachlorbenzene, pentachlorphenole and its salts, phthalide, tolylfluanid, N-(4-chloro-2-nitro-phenyl)-N-ethyl-4-methyl-benzenesulfonamide;

F.VIII 4) guanidines and others: guanidine, dodine, dodine free base, guazatine, guazatine-acetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)-tetraone;

F.IX) Cell wall synthesis inhibitors

F.IX 1) inhibitors of glucan synthesis: validamycin, polyoxin B;

F.IX 2) melanin synthesis inhibitors: pyroquilon, tricyclazole, carpropamid, dicyclomet, fenoxanil;

F.X) Plant defence inducers

F.X 1) acibenzolar-S-methyl, probenazole, isotianil, tiadinil, prohexadione-calcium;

F.X 2) phosphonates: fosetyl, fosetyl-aluminum, phosphorous acid and its salts, 4-cyclopropyl-N-(2,4-dimethoxyphenyl)thiadiazole-5-carboxamide;

F.XI) Unknown mode of action
bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, picarbutrazox, tolprocarb, 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, methoxy-acetic acid 6-tert-butyl-8-fluoro-2,3-dimethyl-quinolin-4-yl ester, 3-[5-(4-methylphenyl)-2,3-dimethyl-isoxazolidin-3-yl]-pyridine, 3-[5-(4-chloro-phenyl)-2,3-dimethyl-isoxazolidin-3-yl]-pyridine (pyrisoxazole), N-(6-methoxy-pyridin-3-yl) cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate, pentyl N-[6-[[(Z)-[(1-methyltetrazol-5-yl)-phenyl-methylene]amino]oxymethyl]-2-pyridyl]carbamate, 2-[2-[(7,8-difluoro-2-methyl-3-quinolyl)oxy]-6-fluoro-phenyl]propan-2-ol, 2-[2-fluoro-6-[(8-fluoro-2-methyl-3-quinolyl)oxy]phenyl]propan-2-ol, 3-(5-fluoro-3,3,4,4-tetramethyl-3,4-dihydroisoquinolin-1-yl)quinoline, 3-(4,4-difluoro-3,3-dimethyl-3,4-dihydroisoquinolin-1-yl)quinoline, 3-(4,4,5-trifluoro-3,3-dimethyl-3,4-dihydroisoquinolin-1-yl)quinoline;

F.XII) Biopesticides

F.XII 1) Microbial pesticides with fungicidal, bactericidal, viricidal and/or plant defense activator activity: *Ampelomyces quisqualis, Aspergillus flavus, Aureobasidium pullulans, Bacillus amyloliquefaciens, B. mojavensis, B. pumilus, B. simplex, B. solisalsi, B. subtilis, B. subtilis* var. *amyloliquefaciens, Candida oleophila, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea* f. *catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus polymyxa, Pantoea vagans, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. violaceusniger, Talaromyces flavus, Trichoderma atroviride, T. fertile, T. gamsii, T. harmatum, T. harzianum*; mixture of *T. harzianum* and *T. viride*; mixture of *T. polysporum* and *T. harzianum*; *T. stromaticum, T. virens* (also named *Gliocladium virens*), *T. viride, Typhula phacorrhiza, Ulocladium oudemansii, Verticillium dahlia*, zucchini yellow mosaic virus (avirulent strain);

F.XII 2) Biochemical pesticides with fungicidal, bactericidal, viricidal and/or plant defense activator activity: chitosan (hydrolysate), harpin protein, laminarin, Menhaden fish oil, natamycin, Plum pox virus coat protein, potassium or sodium bicarbonate, *Reynoutria sachlinensis* extract, salicylic acid, tea tree oil.

Preferred compounds I are stated above.

The methods and mixtures of the invention preferably include one or more pesticidal compounds II. More preferred the active compounds II and III employed in the methods and mixtures of the inventions consist of one or more compounds II, or of one or more compounds II and/or one or more compounds III. If more than one compound of formula II and/or III is employed it is preferably 2 or 3 compounds that are used.

Preferred active compounds II selected from groups M and L:

For each of the following the preferred combination partner I is bilobalide, ginkgolide A or a mixture of bilobalide and ginkgolide A.

With respect to their use in the methods and pesticidal mixtures of the present invention preference is given to compounds II selected from the groups II-M.2B, II-M.3A, II-M.4A, II-M.5, II-M.6, II-M.10, II-M.13, II-M.21A, II-M.25, II-M.22, II-M23, II-M.28, II-M.UN and II-L.3. Particular preference is given to the groups II-M and L wherein the at least one active compound II is selected from
II-M.2B within the class of fiproles from fipronil or ethiprole;
II-M.3A within the class of pyrethroids from alpha-cypermethrin and pyrethrum;
II-M.4A within the class of neonicotinoids from acetamiprid, chlothianidin, dinotefuran, imidacloprid, nitenpyram, thiacloprid or thiamethoxam;
II-M.5 within the class of spinosyns from spinosad or spinetoram;
II-M.6 within the class of mectins from abamectin or emamectin;
II-M.10 within the mite growth inhibitors from etoxazole;
II-M.13 within the uncouplers of oxidative phosphorylation from chlorfenapyr;
II-M.21A within the class of mitochondrial complex I electron transport inhibitors from pyridaben, tebufenpyrad, tolfenpyrad or flufenerim;
II-M.25 within the class of mitochondrial complex II electron transport inhibitors from cyenopyrafen and cyflumetofen;
II-M.22 within the voltage-dependent sodium channel blockers from indoxacarb or metaflumizone;
II-M.23 within the inhibitors of the lipid synthesis from spirodiclofen, spiromesifen or spirotetramat;
II-M.28 within the class of diamides from flubendiamide, chlorantraniliprole, cyantraniliprole, cyclaniliprole or tetraniliprole;
II-M.UN within the compounds of unknown or uncertain mode of action from afidopyropene, afoxolaner, bifenazate, flupyradifurone, fluralaner, piperonyl butoxide, pyridalyl, pyrifluquinazon, sulfoxaflor or triflumezopyrim;
II-M.BP-1 within the class of microbial pesticides from *Bacillus firmus, B. thuringiensis* ssp. *israelensis*, B. t. ssp. *galleriae*, B. t. ssp. *kurstaki, Beauveria bassiana, Burkholderia* sp. or *Paenibacillus* poppiliae.

With regard to the use in a method and pesticidal mixture of the present invention, the compound II is preferably selected from group M-II.2.B as defined above and is preferably fipronil or ethiprole, more preferably fipronil.

With regard to the use in a method of the present invention, the compound II is preferably selected from group M-II.3A defined above and is preferably alpha-cypermethrin, acrinathrin, bifenthrin, cyfluthrin, lambda-cyhalothrin, cypermethrin, beta-cypermethrin, zeta-cypermethrin, deltamethrin, esfenvalerate, etofenprox, fenpropathrin, flucythrinate, tau-fluvalinate, silafluofen or tralomethrin. Further preferred is pyrethrum.

More preferably the compound II is alpha-cypermethrin, lambda-cyhalothrin, bifenthrin, pyrethrum or deltamethrin, most preferably it is alpha-cypermethrin or pyrethrum.

With regard to the use in a method and pesticidal mixture of the present invention, the compound II is preferably selected from group M-II.4A as defined above and is preferably acetamiprid, chlothianidin, dinotefuran, imidacloprid, nitenpyram, thiacloprid or thiamethoxam.

More preferably the compound II is acetamiprid.
More preferably the compound II is clothianidin.
More preferably the compound II is imidacloprid.
More preferably the compound II is thiamethoxam.
More preferably the compound II is dinotefuran.

With regard to the use in a method and pesticidal mixture of the present invention, the compound II is preferably selected from group M-II.5 as defined above and is preferably spinosad.

With regard to the use in a method and pesticidal mixture of the present invention, the compound II is preferably selected from group M-II.6 as defined above and is preferably abamectin, emamectin benzoate, lepimectin or milbemectin.

More preferably the compound II is abamectin.
More preferably the compound II is emamectin.
Most preferably the compound II is abamectin.

With regard to the use in a pesticidal mixture of the present invention, the compound II is preferably selected from group M-II.X (compounds of unknown or uncertain mode of action) as defined above and is preferably flupyradifurone or sulfoxaflor.

With regard to the use in a method and pesticidal mixture of the present invention, the compound II is preferably selected from group II-L.3 (biopesticides).

More preferably the compound II is a microbial pesticide, most preferably *Beauveria bassiana*.

In a further embodiment compound (I) is not *Beauveria bassiana*.

Especially preferred are methods employing pesticidal mixtures containing alpha-cypermethrin as compound II.

Especially preferred are methods employing pesticidal mixtures containing pyrethrum as compound II.

Especially preferred are pesticidal mixtures containing fipronil or ethiprole as compound II.

Especially preferred are pesticidal mixtures containing imidacloprid as compound II.

Especially preferred are pesticidal mixtures containing acetamiprid as compound II.

Especially preferred are pesticidal mixtures containing chlothianidine as compound II.

Especially preferred are pesticidal mixtures containing dinotefuran as compound II.

Especially preferred are pesticidal mixtures containing nitenpyram as compound II.

Especially preferred are pesticidal mixtures containing thiacloprid as compound II.

Especially preferred are pesticidal mixtures containing spinosad as compound II.

Especially preferred are pesticidal mixtures containing abamectin as compound II.

Especially preferred are pesticidal mixtures containing sulfoxaflor as compound II.

Especially preferred are pesticidal mixtures containing flupyradifurone as compound II.

Especially preferred are pesticidal mixtures containing the compound *Beauveria bassiana* as compound II.

Preferred fungicidal active compounds III selected from group F

With respect to their use in the pesticidal mixtures of the present invention, particular preference is given to certain fungicidal active compounds III listed in the paragraphs below.

In a further preferred embodiment compound III is preferably selected from group F.Ia).

More preferably the compound III is azoxystrobin, fluoxastrobin, picoxystrobin, pyraclostrobin or trifloxystrobin.

Most preferably the compound III is pyraclostrobin.

In a further preferred embodiment compound III is preferably selected from group F.Ic).

More preferably the compound III is bixafen, boscalid, fluopyram, fluxapyroxad, isopyrazam, penflufen, penthiopyrad or sedaxane.

More preferably the compound III is fluxapyroxad.

More preferably the compound III is boscalid.

Most preferably the compound III is fluxapyroxad.

In a further preferred embodiment compound (III) is a thio or dithiocarbamate (F.VIII2), in particular mancozeb.

In a further preferred embodiment compound (III) is a respiratory inhibitor (F.I4), preferably a nitrophenyl derivative, in particular amectotradin.

In a further preferred embodiment compound (III) is a tubulin inhibitor (F.IV2), in particular carbendazim.

In a further preferred embodiment compound (III) is a signal transduction inhibitor (F.VI), preferably a MAP/histidine kinase inhibitor, in particular iprodione.

In a further preferred embodiment compound (III) is a C14 demethylase inhibitor (F.II), preferably a triazole, in particular epoxiconazole or difenoconazole, or a imidazole, in particular prochloraz.

In a further preferred embodiment compound (III) is a organochlorine compound (F.VIII3), in particular chlorothalonit.

In a further preferred embodiment compound (III) is a inhibitor of 3-keto reductage (F.II3), in particular fenhexamid.

In a further preferred embodiment compound (III) is a methionine synthesis inhibitor (F.V1), in particular pyrimethanil.

Preferred for application in the method of the invention or as mixture of the invention are the mixtures shown in Table A.

TABLE A

| Preferred mixtures of the invention | | | |
|---|---|---|---|
| No | Compound I | Compound II | Compound III |
| 1. | bilobalide | alpha-cypermethrin | |
| 2. | bilobalide | fipronil | |
| 3. | bilobalide | ethiprole | |
| 4. | bilobalide | acetamiprid | |
| 5. | bilobalide | chlothianidin | |
| 6. | bilobalide | dinotefuran | |
| 7. | bilobalide | imidaclorid | |
| 8. | bilobalide | nitenpyram | |
| 9. | bilobalide | thiacloprid | |
| 10. | bilobalide | thiamethoxam | |
| 11. | bilobalide | spinosad | |
| 12. | bilobalide | abamectin | |
| 13. | bilobalide | flupyradifurone | |
| 14. | bilobalide | sulfoxaflor | |
| 15. | bilobalide | *Beauveria bassiana* | |
| 16. | bilobalide | | pyraclostrobin |
| 17. | bilobalide | | fluxapyroxad |
| 18. | ginkgolide A | alpha-cypermethrin | |
| 19. | ginkgolide A | fipronil | |
| 20. | ginkgolide A | ethiprole | |
| 21. | ginkgolide A | acetamiprid | |
| 22. | ginkgolide A | chlothianidin | |
| 23. | ginkgolide A | dinotefuran | |
| 24. | ginkgolide A | imidaclorid | |
| 25. | ginkgolide A | nitenpyram | |
| 26. | ginkgolide A | thiacloprid | |
| 27. | ginkgolide A | thiamethoxam | |
| 28. | ginkgolide A | spinosad | |
| 29. | ginkgolide A | abamectin | |
| 30. | ginkgolide A | flupyradifurone | |
| 31. | ginkgolide A | sulfoxaflor | |
| 32. | ginkgolide A | *Beauveria bassiana* | |
| 33. | ginkgolide A | | pyraclostrobin |
| 34. | ginkgolide A | | fluxapyroxad |
| 35. | bilobalide and ginkgolide A | alpha-cypermethrin | |
| 36. | bilobalide and ginkgolide A | fipronil | |
| 37. | bilobalide and ginkgolide A | ethiprole | |
| 38. | bilobalide and ginkgolide A | acetamiprid | |
| 39. | bilobalide and ginkgolide A | chlothianidin | |
| 40. | bilobalide and ginkgolide A | dinotefuran | |
| 41. | bilobalide and ginkgolide A | imidaclorid | |
| 42. | bilobalide and ginkgolide A | nitenpyram | |
| 43. | bilobalide and ginkgolide A | thiacloprid | |
| 44. | bilobalide and ginkgolide A | thiamethoxam | |
| 45. | bilobalide and ginkgolide A | spinosad | |
| 46. | bilobalide and ginkgolide A | abamectin | |
| 47. | bilobalide and ginkgolide A | flupyradifurone | |
| 48. | bilobalide and ginkgolide A | sulfoxaflor | |
| 49. | bilobalide and ginkgolide A | *Beauveria bassiana* | |
| 50. | bilobalide and ginkgolide A | | pyraclostrobin |
| 51. | bilobalide and ginkgolide A | | fluxapyroxad |
| 52. | ginkgolide B | alpha-cypermethrin | |
| 53. | ginkgolide B | fipronil | |
| 54. | ginkgolide B | ethiprole | |
| 55. | ginkgolide B | acetamiprid | |
| 56. | ginkgolide B | chlothianidin | |
| 57. | ginkgolide B | dinotefuran | |
| 58. | ginkgolide B | imidaclorid | |
| 59. | ginkgolide B | nitenpyram | |
| 60. | ginkgolide B | thiacloprid | |
| 61. | ginkgolide B | thiamethoxam | |
| 62. | ginkgolide B | spinosad | |
| 63. | ginkgolide B | abamectin | |
| 64. | ginkgolide B | flupyradifurone | |
| 65. | ginkgolide B | sulfoxaflor | |
| 66. | ginkgolide B | *Beauveria bassiana* | |
| 67. | ginkgolide B | | pyraclostrobin |
| 68. | ginkgolide B | | fluxapyroxad |
| 69. | ginkgolide C | alpha-cypermethrin | |
| 70. | ginkgolide C | fipronil | |
| 71. | ginkgolide C | ethiprole | |
| 72. | ginkgolide C | acetamiprid | |
| 73. | ginkgolide C | chlothianidin | |
| 74. | ginkgolide C | dinotefuran | |
| 75. | ginkgolide C | imidaclorid | |
| 76. | ginkgolide C | nitenpyram | |
| 77. | ginkgolide C | thiacloprid | |
| 78. | ginkgolide C | thiamethoxam | |
| 79. | ginkgolide C | spinosad | |
| 80. | ginkgolide C | abamectin | |
| 81. | ginkgolide C | flupyradifurone | |
| 82. | ginkgolide C | sulfoxaflor | |
| 83. | ginkgolide C | *Beauveria bassiana* | |
| 84. | ginkgolide C | | pyraclostrobin |
| 85. | ginkgolide C | | fluxapyroxad |
| 86. | ginkgolide J | alpha-cypermethrin | |
| 87. | ginkgolide J | fipronil | |
| 88. | ginkgolide J | ethiprole | |
| 89. | ginkgolide J | acetamiprid | |

TABLE A-continued

Preferred mixtures of the invention

| No | Compound I | Compound II | Compound III |
|---|---|---|---|
| 90. | ginkgolide J | chlothianidin | |
| 91. | ginkgolide J | dinotefuran | |
| 92. | ginkgolide J | imidaclorid | |
| 93. | ginkgolide J | nitenpyram | |
| 94. | ginkgolide J | thiacloprid | |
| 95. | ginkgolide J | thiamethoxam | |
| 96. | ginkgolide J | spinosad | |
| 97. | ginkgolide J | abamectin | |
| 98. | ginkgolide J | flupyradifurone | |
| 99. | ginkgolide J | sulfoxaflor | |
| 100. | ginkgolide J | *Beauveria bassiana* | |
| 101. | ginkgolide J | | pyraclostrobin |
| 102. | ginkgolide J | | fluxapyroxad |
| 103. | ginkgolide M | alpha-cypermethrin | |
| 104. | ginkgolide M | fipronil | |
| 105. | ginkgolide M | ethiprole | |
| 106. | ginkgolide M | acetamiprid | |
| 107. | ginkgolide M | chlothianidin | |
| 108. | ginkgolide M | dinotefuran | |
| 109. | ginkgolide M | imidaclorid | |
| 110. | ginkgolide M | nitenpyram | |
| 111. | ginkgolide M | thiacloprid | |
| 112. | ginkgolide M | thiamethoxam | |
| 113. | ginkgolide M | spinosad | |
| 114. | ginkgolide M | abamectin | |
| 115. | ginkgolide M | flupyradifurone | |
| 116. | ginkgolide M | sulfoxaflor | |
| 117. | ginkgolide M | *Beauveria bassiana* | |
| 118. | ginkgolide M | | pyraclostrobin |
| 119. | ginkgolide M | | fluxapyroxad |
| 120. | bilobalide | alpha-cypermethrin | pyraclostrobin |
| 121. | bilobalide | alpha-cypermethrin | fluxapyroxad |
| 122. | bilobalide | fipronil | pyraclostrobin |
| 123. | bilobalide | fipronil | fluxapyroxad |
| 124. | bilobalide | ethiprole | pyraclostrobin |
| 125. | bilobalide | ethiprole | fluxapyroxad |
| 126. | bilobalide | acetamiprid | pyraclostrobin |
| 127. | bilobalide | acetamiprid | fluxapyroxad |
| 128. | bilobalide | chlothianidin | pyraclostrobin |
| 129. | bilobalide | chlothianidin | fluxapyroxad |
| 130. | bilobalide | dinotefuran | pyraclostrobin |
| 131. | bilobalide | dinotefuran | fluxapyroxad |
| 132. | bilobalide | imidaclorid | pyraclostrobin |
| 133. | bilobalide | imidaclorid | fluxapyroxad |
| 134. | bilobalide | nitenpyram | pyraclostrobin |
| 135. | bilobalide | nitenpyram | fluxapyroxad |
| 136. | bilobalide | thiacloprid | pyraclostrobin |
| 137. | bilobalide | thiacloprid | fluxapyroxad |
| 138. | bilobalide | thiamethoxam | pyraclostrobin |
| 139. | bilobalide | thiamethoxam | fluxapyroxad |
| 140. | bilobalide | spinosad | pyraclostrobin |
| 141. | bilobalide | spinosad | fluxapyroxad |
| 142. | bilobalide | abamectin | pyraclostrobin |
| 143. | bilobalide | abamectin | fluxapyroxad |
| 144. | bilobalide | flupyradifurone | pyraclostrobin |
| 145. | bilobalide | flupyradifurone | fluxapyroxad |
| 146. | bilobalide | sulfoxaflor | pyraclostrobin |
| 147. | bilobalide | sulfoxaflor | fluxapyroxad |
| 148. | bilobalide | *Beauveria bassiana* | pyraclostrobin |
| 149. | bilobalide | *Beauveria bassiana* | fluxapyroxad |
| 150. | ginkgolide A | alpha-cypermethrin | pyraclostrobin |
| 151. | ginkgolide A | alpha-cypermethrin | fluxapyroxad |
| 152. | ginkgolide A | fipronil | pyraclostrobin |
| 153. | ginkgolide A | fipronil | fluxapyroxad |
| 154. | ginkgolide A | ethiprole | pyraclostrobin |
| 155. | ginkgolide A | ethiprole | fluxapyroxad |
| 156. | ginkgolide A | acetamiprid | pyraclostrobin |
| 157. | ginkgolide A | acetamiprid | fluxapyroxad |
| 158. | ginkgolide A | chlothianidin | pyraclostrobin |
| 159. | ginkgolide A | chlothianidin | fluxapyroxad |
| 160. | ginkgolide A | dinotefuran | pyraclostrobin |
| 161. | ginkgolide A | dinotefuran | fluxapyroxad |
| 162. | ginkgolide A | imidaclorid | pyraclostrobin |
| 163. | ginkgolide A | imidaclorid | fluxapyroxad |
| 164. | ginkgolide A | nitenpyram | pyraclostrobin |
| 165. | ginkgolide A | nitenpyram | fluxapyroxad |
| 166. | ginkgolide A | thiacloprid | pyraclostrobin |
| 167. | ginkgolide A | thiacloprid | fluxapyroxad |
| 168. | ginkgolide A | thiamethoxam | pyraclostrobin |
| 169. | ginkgolide A | thiamethoxam | fluxapyroxad |
| 170. | ginkgolide A | spinosad | pyraclostrobin |
| 171. | ginkgolide A | spinosad | fluxapyroxad |
| 172. | ginkgolide A | abamectin | pyraclostrobin |
| 173. | ginkgolide A | abamectin | fluxapyroxad |
| 174. | ginkgolide A | flupyradifurone | pyraclostrobin |
| 175. | ginkgolide A | flupyradifurone | fluxapyroxad |
| 176. | ginkgolide A | sulfoxaflor | pyraclostrobin |
| 177. | ginkgolide A | sulfoxaflor | fluxapyroxad |
| 178. | ginkgolide A | *Beauveria bassiana* | pyraclostrobin |
| 179. | ginkgolide A | *Beauveria bassiana* | fluxapyroxad |
| 180. | bilobalide | pyrethrum | |
| 181. | ginkgolide A | pyrethrum | |
| 182. | bilobalide + ginkgolide A | pyrethrum | |
| 183. | bilobalide | | pyraclostrobin |
| 184. | ginkgolide A | | pyraclostrobin |
| 185. | bilobalide + ginkgolide A | | pyraclostrobin |
| 186. | bilobalide | | fluxapyroxad |
| 187. | ginkgolide A | | fluxapyroxad |
| 188. | bilobalide + ginkgolide A | | fluxapyroxad |
| 189. | bilobalide | | mancozeb |
| 190. | ginkgolide A | | mancozeb |
| 191. | bilobalide + ginkgolide A | | mancozeb |
| 192. | bilobalide | | ametoctradin |
| 193. | ginkgolide A | | ametoctradin |
| 194. | bilobalide + ginkgolide A | | ametoctradin |
| 195. | bilobalide | | carbendazim |
| 196. | ginkgolide A | | carbendazim |
| 197. | bilobalide + ginkgolide A | | carbendazim |
| 198. | bilobalide | | iprodion |
| 199. | ginkgolide A | | iprodion |
| 200. | bilobalide + ginkgolide A | | iprodion |
| 201. | bilobalide | | prochloraz |
| 202. | ginkgolide A | | prochloraz |
| 203. | bilobalide + ginkgolide A | | prochloraz |
| 204. | bilobalide | | chlorothalonil |
| 205. | ginkgolide A | | chlorothalonil |
| 206. | bilobalide + ginkgolide A | | chlorothalonil |
| 207. | bilobalide | | azoxystrobin |
| 208. | ginkgolide A | | azoxystrobin |
| 209. | bilobalide + ginkgolide A | | azoxystrobin |
| 210. | bilobalide | | trifloxystrobin |
| 211. | ginkgolide A | | trifloxystrobin |
| 212. | bilobalide + ginkgolide A | | trifloxystrobin |
| 213. | bilobalide | | fenhexamid |
| 214. | ginkgolide A | | fenhexamid |
| 215. | bilobalide + ginkgolide A | | fenhexamid |
| 216. | bilobalide | | pyrimethanil |
| 217. | ginkgolide A | | pyrimethanil |
| 218. | bilobalide + ginkgolide A | | pyrimethanil |
| 219. | bilobalide | | epoxiconazol |
| 220. | ginkgolide A | | epoxiconazol |
| 221. | bilobalide + ginkgolide A | | epoxiconazol |
| 222. | bilobalide | | picoxystrobin |
| 223. | ginkgolide A | | picoxystrobin |
| 224. | bilobalide + ginkgolide A | | picoxystrobin |
| 225. | bilobalide | | difenoconazol |
| 226. | ginkgolide A | | difenoconazol |
| 227. | bilobalide + ginkgolide A | | difenoconazol |

Pests

The compounds applied in the methods of the invention are used, preferably on soybean and/or maize (*Zea mays*), to control pests from the family of Pentatomidae, particularly stinkbugs, e.g. *Nezara* spp. (e.g. *Nezara viridula, Nezara antennata, Nezara hilaris*), *Piezodorus* spp. (e.g. *Piezodorus guildinii*), *Acrosternum* spp. (e.g. *Acrosternum hilare*), *Euchistus* spp. (e.g. *Euchistus heros, Euschistus servus*), *Halyomorpha halys, Megacopta cribaria, Plautia crossota, Riptortus clavatus, Rhopalus msculatus, Antestiopsis orbitalus, Dectes texanus, Dichelops* spp. (e.g. *Dichelops furcatus,*

*Dichelops melacanthus*), *Eurygaster* spp. (e.g. *Eurygaster intergriceps, Eurygaster maurd*), *Oebalus* spp. (e.g. *Oebalus mexicana, Oebalus poecilus, Oebalus pugnase, Scotinophara* spp. (e.g. *Scotinophara lurida, Scotinophara coarctatd*). Preferred targets include *Acrosternum hilare, Antestiopsis orbitalus, Dichelops furcatus, Dichelops melacanthus, Euchistus heros, Euschistus servus, Megacopta cribaria, Nezara viridula, Nezara hilare, Piezodorus guildinii, Halyomorpha halys*. In one embodiment the stinkbug target is *Nezara viridula, Piezodorus* spp., *Acrosternum* spp, *Euchistus heros. Euschistus* and in particular *Euchistus heros* are preferred targets.

Further pests in particular of soybeans and/or maize that can be controlled with the mixtures of the invention include *Elasmopalpus lignosellus, Diloboderus abderus, Diabrotica speciosa, Sternechus subsignatus, Formicidae, Agrotis ypsilon, Julus* ssp., *Anticarsia gemmatalis, Megacopta* spp., *Megascelis* ssp., *Procornitermes* ssp., Gryllotalpidae, *Nezara viridula, Neomegalotomus* spp., *Cerotoma trifurcata, Popillia japonica, Edessa* spp., *Liogenys fuscus*, stem borer, *Dectes* spp, stalk borer, *Scaptocoris castanea, phyllophaga* spp., *Pseudoplusia includens, Spodoptera* spp., *Bemisia tabaci, Agriotes* spp., Thripidae, preferably *Diloboderus abderus, Diabrotica speciosa, Piezodorus* spp., *Cerotoma trifurcata, Popillia japonica, Phyllophaga* spp. *Agriotes* spp.

Depending on the spectrum of activity of the compounds II, mixtures of the invention can be used for the control of: insects from the order of the lepidopterans (Lepidoptera), such as *Heliothis* spp., e.g. *Heliothis virescens*,
beetles (Coleoptera), such as *Anthonomus* spp., e.g. *Anthonomus grandis*,
flies, mosquitoes (Diptera), such as *Ceratitis* spp., e.g. *Ceratitis capitata, Aedes* spp., e.g. *Aedes aegypti*,
termites (Isoptera),
cockroaches (Blattaria—Blattodea),
bugs, aphids, leafhoppers, whiteflies, scale insects, cicadas (Hemiptera),
ants, bees, wasps, sawflies (Hymenoptera),
crickets, grasshoppers, locusts (Orthoptera),
arachnids (Arachnida),
fleas (Siphonaptera),
silverfish, firebrat (Thysanura),
centipedes (Chilopoda),
millipedes (Diplopoda),
earwigs (Dermaptera),
lice (Phthiraptera),
springtails (Collembola),
and
plant parasitic nematodes.

Depending on the spectrum of activity of the compounds III, mixtures of the invention can be used for the control of phytopathogenic fungi and fungus-like eukaryotic microorganisms from Ascomycetes, Basidiomycetes, Deuteromycetes and Peremosporomycetes (syn. Domycetes).

*Phytophtora* such as Examples of pathogens are *Phytophtora infestans, Botrytis*, such as *Botrytis cinerea, Pyricularia* such as *Pyricularia oryzae, Septoria* such as *Septoria tritici, Alternaria* such as *Alternaria solani* and *Leptosphaeria*, such as *Leptosphaeria nodorum*.

Some of them are systemically effective and can be employed in crop protection as foliar fungicides, as fungicides for seed dressing and as soil fungicides. They can also be used for treating seed.

They are particularly important in the control of a multitude of fungi on various cultivated plants, such as maize, wheat, rye, barley, oats, rice, corn, lawns, bananas, cotton, soybean, lima bean, coffee, sugar cane, grapevines, fruits and ornamental plants and vegetables such as cucumbers, beans, tomatoes, potatoes and curcurbits, and on the seeds of these plants.

Formulations

The mixtures according to the invention and applied in the methods of the invention can be converted into the customary formulations, for example solutions, emulsions, suspensions, dusts, powders, pastes and granules. The use form depends on the particular intended purpose; in each case, it should ensure a fine and even distribution of the compounds according to the invention.

Therefore the invention also relates to agrochemical compositions comprising an auxiliary and a mixture of at least one compound I of formula I and of at least one compound II and/or one compound III according to the present invention.

An agrochemical composition comprises a pesticidally effective amount of a compound I. The term "effective amount" denotes an amount of the composition or of the compounds I, which is sufficient for controlling harmful pests on cultivated plants or in the protection of materials and which does not result in a substantial damage to the treated plants. Such an amount can vary in a broad range and is dependent on various factors, such as the fungal species and/or the pest species to be controlled, the treated cultivated plant or material, the climatic conditions and the specific compound I used.

The active compounds I and II and/or III, their N-oxides and salts can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Mon-ograph No. 2, 6th Ed. May 2008, CropLife International.

The compositions are prepared in a known manner, such as described by Mollet and Grube-mann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl-sulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanofer-rate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required. In some cases the amount for seed treatment may be up to 100 kilogram per 100 kilogram of seeds, or may even excess the seed weight.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e. g. components comprising active compound I and active compounds II (and optionally active compounds III), may be mixed by the user in a spray tank and further auxiliaries and additives may be added, if appropriate.

In a further embodiment, either individual components of the composition according to the invention or partially premixed components, e. g. components comprising active compound I and active compounds II and/or III, can be applied jointly (e.g. after tank mix) or consecutively.

Applications

The compound I and the one or more compound(s) II and/or III can be applied simultaneously, that is jointly or separately, or in succession, that is immediately one after another and thereby creating the mixture "in-situ" on the desired location, as e.g. the plant, the sequence, in the case of separate application, generally not having any effect on the result of the control measures.

The mixtures of the invention are employed as such or in form of compositions by treating the insects or the plants, plant propagation materials, such as seeds, soil, surfaces, materials or rooms to be protected from insecticidal attack with an insecticidally effective amount of the active compounds. The application can be carried out both before and after the infection of the plants, plant propagation materials, such as seeds, soil, surfaces, materials or rooms by the insects.

In the mixtures and compositions according to the invention, the weight ratio of the compound I and compound II or III generally depends from the properties of the compounds II or III used, usually it is in the range of from 10 000:1 to 1:10, regularly in the range of from 7500:1 to 1:5, preferably in the range of from 5000:1 to 1:5, more preferably in the range of from 1000:1 to 1:2, even more preferably in the range of from 500:1 to 5:1 and in particular in the range of from 300:1 to 5:1.

According to further embodiments of the mixtures according to the invention, the weight ratio of compound I to compound II usually is in the range of from 10 000:1 to 1:10, regularly in the range of from 5000:1 to 1:5, preferably in the range of from 3000:1 to 1:2, more preferably in the range of from 1000:1 to 1:1, even more preferably in the range of from 500:1 to 1:1 and in particular in the range of from 250:1 to 5:1.

According to further embodiments of the mixtures according to the invention, the weight ratio of compound I to compound III usually is in the range of from 5000:1 to 1:5, regularly in the range of from 2000:1 to 1:1, preferably in the range of from 1500:1 to 1:1, more preferably in the range of from 1000:1 to 2:1, even more preferably in the range of from 500:1 to 5:1 and in particular in the range of from 300:1 to 1:10.

In the ternary mixtures, i.e. compositions according to the invention comprising compound I (component 1) and a compound II (component 2) and a compound III (component 3), the weight ratio of component 1) and component 2) depends from the properties of the active substances used. In one embodiment the amounts of compounds I, II and III are derived from the above values for the weight ratios of compounds I and compounds II and III respectively.

Typical values for certain classes of compounds (with compound (I) being preferably bilobalide or ginkgolide A) are: Neonicotinoids, such as dinotefuran, midacloprid and thiamethoxam (weight ratio compound (I) to compound (III) 10 000:1 to 1: 1, preferably 7500:1 to 50 to 1, more preferred 5000:1 to 100 to 1, in particular 4500 to 1 to 150 to 1.

For synthetic pyrethroids, such as α-cypermethrin the ratios for neonicotinoids are applicable.

The same applies for chloride channel activators, preferably avermectins such as abamectin.

For pyrethrum and nicotinic acetylcholine receptor allosteric activators, preferably spinosyns, such as spinosad, a typical ratio is (I:II):100:1 to 1 to 100, preferably 10:1 to 1:50, more preferably 5:1 to 1:10, in particular 1:2 to 1:5, specifically 1:1 to 1:3.

Strobilurines, such as pyraclostrobin, azoxystrobin, trifluxystrobin and picoxystrobin (I:III) 5000:1 to 1:1, preferably 2000:1 to 10:1, more preferably 1000:1 to 1:50.

For other fungicides such as fluxapyroxad, mancozeb, ametoctradin, carbendazim, iprodion, prochloraz, chlorothalonil, fenhexamid, pyrimethanil, epoxiconazol and difenoconazol, as well as for the classes of fungicides they represent typical weight ratios (I:III) are 250:1 to 1:5, preferably 200:1 to 1:1, more preferred 150:1 to 1:2, in particular 100:1 to 1:2, especially 80:1 to 1:5.

In a further embodiment, the weight ratio of the compound I and compound II or III is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1.

According to further embodiments of the mixtures according to the invention, the weight ratio of compound I to compound II or III usually is in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to further embodiments of the mixtures according to the invention, the weight ratio of compound I to compound II or III usually is in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

In one embodiment compound 1 is used in excess as compared to compound II or III, i.e. the weight ratio of compound I to compound II or III usually is in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1, e.g. of from 3:1 to 1:1, and in particular in the range of from 2:1 to 1:1.

In a further embodiment of ternary mixtures, i.e. compositions according to the invention comprising compound I (component 1) and a compound II (component 2) and a compound III (component 3), the weight ratio of component 1) and component 2) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to compound I.

In further embodiments of the invention the compound I and the one or more compound(s) II and/or III are applied in a weight ratio of from 500:1 to 1:100, preferably from 20:1 to 1:50, in particular from 5:1 to 1:20.

For microbial pesticides in one embodiment the ratio of microbial pesticide to compound (I) is from $1\times10E\ 4$ CFU/ml to $1\times10E\ 8$ CFU/ml per ppm, preferably from $1\times10E\ 4$ CFU/ml to $1\times10E\ 7$ CFU/ml per ppm, more preferably from $5\times10E\ 4$ CFU/ml to $5\times10E\ 6$ CFU/ml per ppm, in particular $7.5\times10E\ 4$ CFU/ml to $7.5\times10E\ 5$ CFU/ml per ppm.

This may apply e.g. if compound (II) is *Beauveria basiana*.

In a further embodiment, the ratio of microbial pesticide to compound (I) is from $1\times10E\ 4$ CFU/ml to $1\times10E\ 8$ CFU/ml per ppm, preferably from $1\times10E\ \%$ CFU/ml to $1\times10E\ 7$ CFU/ml per ppm, more preferably from $5\times10E\ \%$ CFU/ml to $5\times10E\ 6$ CFU/ml per ppm (CFU-colony forming unit)

Depending on the desired effect, the application rates of the mixtures according to the invention are from 5 g/ha to 2000 g/ha, preferably from 50 to 1500 g/ha, in particular from 50 to 750 g/ha.

The mixtures according to the invention are effective through both contact and ingestion.

According to a preferred embodiment of the invention, the mixtures according to the present invention are employed via soil application. Soil application is especially favorable for use against ants, termites, crickets, or cockroaches.

According to another preferred embodiment of the invention, for use against non-crop pests such as ants, termites, wasps, flies, mosquitoes, crickets, locusts, or cockroaches the mixtures according to the present invention are prepared into a bait preparation.

The bait can be a liquid, a solid or a semisolid preparation (e.g. a gel).

Another aspect of the present invention is when preparing the mixtures, it is preferred to employ the pure active compounds I and II, to which further active compounds, e.g. against harmful fungi or having herbicidal activity, or growth-regulating agents or fertilizers can be added.

Compositions of this invention may further contain other active ingredients than those listed above. For example fungicides, herbicides, fertilizers such as ammonium nitrate, urea, potash, and superphosphate, phytotoxicants and plant growth regulators and safeners. These additional ingredients may be used sequentially or in combination with the above-described compositions, if appropriate also added only immediately prior to use (tank mix). For example, the plant(s) may be sprayed with a composition of this invention either before or after being treated with other active ingredients.

The mixtures according to the invention can be applied to any and all developmental stages, such as egg, larva, pupa, and adult. The pests may be controlled by contacting the target pest, its food supply, habitat, breeding ground or its locus with a pesticidally effective amount of the inventive mixtures or of compositions comprising the mixtures.

"Locus" means a plant, seed, soil, area, material or environment in which a pest is growing or may grow.

In general, "pesticidally effective amount" means the amount of the inventive mixtures or of compositions comprising the mixtures needed to achieve an observable effect on growth, including the effects of necrosis, death, retardation, prevention, and removal, destruction, or otherwise diminishing the occurrence and activity of the target organism. The pesticidally effective amount can vary for the various mixtures and/or compositions used in the invention. A pesticidally effective amount of the mixtures and/or compositions will also vary according to the pre-vailing conditions such as desired pesticidal effect and duration, weather, target species, locus, mode of application, and the like.

The inventive mixtures or compositions of these mixtures can also be employed for protecting plants from attack or infestation by insects, acarids or nematodes comprising contacting a plant, or soil or water in which the plant is growing.

The inventive mixtures are effective through both contact (via soil, glass, wall, bed net, carpet, plant parts or animal parts), and ingestion (bait, or plant part) and through trophallaxis and transfer.

Preferred application methods are into water bodies, via soil, cracks and crevices, pastures, manure piles, sewers, into water, on floor, wall, or by perimeter spray application and bait.

According to another preferred embodiment of the invention, for use against non-crop pests such as ants, termites, wasps, flies, mosquitoes, crickets, locusts, or cockroaches the inventive mixtures are prepared into a bait preparation.

The bait can be a liquid, a solid or a semisolid preparation (e.g. a gel). The bait employed in the composition is a product which is sufficiently attractive to incite insects such as ants, termites, wasps, flies, mosquitoes, crickets etc. or cockroaches to eat it. This attractant may be chosen from feeding stimulants or para and/or sex pheromones readily known in the art.

Methods to control infectious diseases transmitted by insects (e.g. malaria, dengue and yellow fever, lymphatic filariasis, and leishmaniasis) with the inventive mixtures and their respective compositions also comprise treating surfaces of huts and houses, air spraying and impregnation of curtains, tents, clothing items, bed nets, tsetse-flytrap or the like. Insecticidal compositions for application to fibers, fabric, knit goods, non-wovens, netting material or foils and tarpaulins preferably comprise a composition including the inventive mixtures, optionally a repellent and at least one binder.

The inventive mixtures and the compositions comprising them can be used for protecting wood-en materials such as trees, board fences, sleepers, etc. and buildings such as houses, out-houses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities).

In the case of soil treatment or of application to the pests dwelling place or nest, the quantity of active ingredient(s) ranges from 0.0001 to 500 g per 100 m², preferably from 0.001 to 20 g per 100 m².

Customary application rates in the protection of materials are, for example, from 0.01 g to 1000 g of active compound(s) per m² treated material, desirably from 0.1 g to 50 g per m².

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in bait compositions, the typical content of active ingredient(s) is from 0.0001 weight % to 15 weight %, desirably from 0.001 weight % to 5 weight % of active compound. The composition used may also comprise other additives such as a solvent of the active material, a flavoring agent, a preserving agent, a dye or a bitter agent. Its attractiveness may also be enhanced by a special color, shape or texture.

For use in spray compositions, the content of the mixture of the active ingredients is from 0.001 to 80 weight %, preferably from 0.01 to 50 weight % and most preferably from 0.01 to 15 weight %.

For use in treating crop plants, the rate of application of the mixture of the active ingredients of this invention may be in the range of 0.1 g to 4000 g per hectare, desirably from 25 g to 600 g per hectare, more desirably from 50 g to 500 g per hectare.

In the context of the present invention, the term plant refers to an entire plant, a part of the plant or the plant propagation material.

The mixtures of the present invention and the compositions comprising them are particularly important in the control of a multitude of insects on various cultivated plants.

Plants which can be treated with the inventive mixtures include all genetically modified plants or transgenic plants, e.g. crops which tolerate the action of herbicides or fungicides or insecticides owing to breeding, including genetic engineering methods, or plants which have modified characteristics in comparison with existing plants, which can be generated for example by traditional breeding methods and/or the generation of mutants, or by recombinant procedures.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be mentioned. These young plants may also be protected before transplantation by a total or partial treatment by immersion or pouring.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot be obtained by cross breeding, mutations or natural recombination. Typically, one or more genes have been integrated into the genetic material of a genetically modified plant in order to improve certain properties of the plant.

The term "cultivated plants" is to be understood also including plants that have been rendered tolerant to applications of specific classes of herbicides, such as hydroxyphenylpyruvate dioxygenase (HPPD) inhibitors; acetolactate synthase (ALS) inhibitors, such as sulfonyl ureas (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e. g. WO 92/00377); glutamine synthetase (GS) inhibitors, such as glufosinate (see e. g. EP-A-0242236, EP-A-242246) oroxynil herbicides (see e. g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e. g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus Bacillus, particularly from Bacillus thuringiensis, such as ä-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, for example Photorhabdus spp. or Xenorhabdus spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine pro-tease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are disclosed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins tolerance to harmful pests from all taxonomic groups of insects, especially to beetles (Coeloptera), two-winged insects (Diptera), and butter-flies (Lepidoptera).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for example oil crops that produce health-promoting long-chain omega-3 fatty acids or unsaturated omega-9 fatty acids (e. g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e. g. Amflora® potato).

Some of the mixtures of the invention have systemic action and can therefore be used for the protection of the plant shoot against foliar pests as well as for the treatment of the seed and roots against soil pests.

Seed Treatment

Mixtures according to the present invention with systematic action are suitable for the treatment of seeds in order to protect the seed from insect pest, in particular from soil-living insect pests and the resulting plant's roots and shoots against soil pests and foliar insects.

The protection of the resulting plant's roots and shoots is preferred.

More preferred is the protection of resulting plant's shoots from piercing and sucking insects.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with mixtures according to the present invention. Particularly preferred is a method, wherein the plant's roots and shoots are protected, more preferably a method, wherein the plants shoots are protected from piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound(s). The term "coated with and/or containing" generally signifies that the active ingredient(s) are for the most part on the surface of the propagation product at the time of application, although a greater or lesser part of the ingredient may penetrate into the propagation product, depending on the method of application. When the said propagation product is (re)planted, it may absorb the active ingredient.

Suitable seeds are seeds of cereals, root crops, oil crops, vegetables, spices, ornamentals, for example seed of durum and other wheat, barley, oats, rye, maize (fodder maize and sugar maize/sweet and field corn), soybeans, lima beans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

These crops are also particularly suitable for application of the mixtures of the invention to growing plants.

In addition, the mixtures according to the invention may also be used for the treatment seeds from plants, which tolerate the action of herbicides or fungicides or insecticides owing to breeding, including genetic engineering methods.

For example, the active mixtures can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259).

Furthermore, the mixtures according to the present invention can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the mixtures is carried out by spraying or by dusting the seeds before sowing of the plants and before emergence of the plants.

In the treatment of seeds the corresponding formulations are applied by treating the seeds with an effective amount of the mixture according to the present invention. Herein, the application rates of the active compound(s) are generally from 0.1 g to 10 kg per 100 kg of seed, preferably from 1 g to 5 kg per 100 kg of seed, in particular from 1 g to 2.5 kg per 100 kg of seed. For specific crops such as lettuce the rate can be higher.

Compositions, which are especially useful for seed treatment, are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1-800 g/l of active ingredient(s), 1-200 g/l Surfactant, 0 to 200 g/l antifreezing agent, 0 to 400 g/l of binder, 0 to 200 g/l of a pigment and up to 1 liter of a solvent, preferably water.

Preferred FS formulations of compounds of formula I for seed treatment usually comprise from 0.1 to 80% by weight (1 to 800 g/l) of the active ingredient(s), from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed treatment formulations may additionally also comprise binders and optionally colorants.

Binders can be added to improve the adhesion of the active materials on the seeds after treatment. Suitable binders are block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

The invention also relates to seed comprising mixtures according to the present invention. The amount of the compound I or the agriculturally useful salt thereof will in general vary from 0.1 g to 100 kg per 100 kg of seed, preferably from 1 g to 5 kg per 100 kg of seed, in particular from 1 g to 1000 g per 100 kg of seed. For specific crops, e.g. such as lettuce, the rate can be higher. Also in some other cases the amount for seed treatment may be up to 100 kilogram of the active compound(s) per 100 kilogram of seeds, or may even excess the seed weight.

EXAMPLES

A. Compounds

Bilobalide, ginkgolide A, ginkgolide B, ginkgolide C and ginkgolide J are commercially available (e.g. from Interchim).

B. Biology

Synergism can be described as an interaction where the combined effect of two or more compounds is greater than the sum of the individual effects of each of the compounds. The presence of a synergistic effect in terms of percent control, between two mixing partners (X and Y) can be calculated using the Colby equation (Colby, S. R., 1967, Calculating Synergistic and Antagonistic Responses in Herbicide Combinations, *Weeds*, 15, 20-22):

$$E = X + Y - \frac{XY}{100}$$

When the observed combined control effect is greater than the expected combined control effect (E), then the combined effect is synergistic.

The following tests demonstrate the control efficacy of compounds, mixtures or compositions of this invention on specific pests. However, the pest control protection afforded by the compounds, mixtures or compositions is not limited to these species. In certain instances, combinations of a compound of this invention with other invertebrate pest control compounds or agents are found to exhibit synergistic effects against certain important invertebrate pests. The analysis of synergism or antagonism between the mixtures or compositions was determined using Colby's equation.

The following abbreviations were used:
MTP: microtiter plate
Test 1

For evaluating control of boll weevil (*Anthonomus grandis*) the test unit consisted of microtiter plates (MTPs) containing an insect diet and 20-30 *A. grandis* eggs.

The compounds or mixtures were formulated using a solution containing 75% water and 25% DMSO. Different concentrations of formulated compounds or mixtures were sprayed onto the insect diet at 20 µl, using a custom built micro atomizer, at two replications.

For experimental mixtures in these tests identical volumes of both mixing partners at the desired concentrations respectively, were mixed together.

After application, MTPs were incubated at 23±1° C., 50±5% room humidity for 5 days. Egg and larval mortality was then visually assessed. For the mixture tested the results are listed in Table 1.

TABLE 1

| Active compound/ active mixture | Concentration (ppm) | Ratio | Observed efficacy (%) | Calculated efficacy according to Colby (%) |
|---|---|---|---|---|
| Dinotefuran | 0.08 | — | 0 | — |
| Bilobalide | 160 | — | 0 | — |

TABLE 1-continued

| Active compound/ active mixture | Concentration (ppm) | Ratio | Observed efficacy (%) | Calculated efficacy according to Colby (%) |
|---|---|---|---|---|
| Dinotefuran + Bilobalide | 0.08 160 | 1:2000 | 100 | 0 |
| Imidacloprid + Bilobalide | 0.8 160 | — | 25 0 | — — |
| Imidacloprid + Bilobalide | 0.8 160 | 1:2000 | 100 | 25 |
| Abamectin Bilobalide | 0.003 64 | — | 0 25 | — — |
| Abamectin + Bilobalide | 0.003 64 | 1:21333 | 75 | 25 |
| Imicacloprid Ginkgolide A | 0.8 20 | — | 0 0 | — — |
| Imidacloprid + Ginkgloide A | 0.8 20 | 1:25 | 50 | 0 |

Test 2

For evaluating control of Mediterranean fruitfly (*Ceratitis capitata*) the test unit consisted MTPs containing an insect diet and 50-80 *C. capitata* eggs. The compounds or mixtures were formulated using a solution containing 75% water and 25% DMSO. Different concentrations of formulated compounds or mixtures were sprayed onto the insect diet at 5 μl, using a custom built micro atomizer, at two replications. For experimental mixtures in these tests identical volumes of both mixing partners at the desired concentrations respectively, were mixed together. After application, MTPs were incubated at 28±1° C., 80±5% room humidity for 5 days. Egg and larval mortality was then visually assessed. For the mixture tested the results are listed in Table 2.

TABLE 2

| Active compound/ active mixture | Concentration (ppm) | Ratio | Observed efficacy (%) | Calculated efficacy according to Colby (%) |
|---|---|---|---|---|
| Thiamethoxam Bilobalide | 0.08 160 | — | 0 0 | — — |
| Thiamethoxam + Bilobalide | 0.08 160 | 1:2000 | 75 | 0 |
| Alphacypermethrin Bilobalide | 0.4 160 | — | 0 0 | — — |
| Alphacypermethrin + Bilobalide | 0.4 160 | 1:400 | 50 | 0 |

Test 3

For evaluating control of tobacco budworm (*Heliothis virescens*) the test unit consisted of MTPs containing an insect diet and 15-25 *H. virescens* eggs. The compounds or mixtures were formulated using a solution containing 75% water and 25% DMSO. Different concentrations of formulated compounds or mixtures were sprayed onto the insect diet at 10 μl, using a custom built micro atomizer, at two replications. For experimental mixtures in these tests identical volumes of both mixing partners at the desired concentrations respectively, were mixed together. After application, MTPs were incubated at 28±1° C., 80±5% room humidity for 5 days. Egg and larval mortality was then visually assessed. The results were listed in Table 3.

TABLE 3

| Active compound/ active mixture | Concentration (ppm) | Ratio | Observed efficacy (%) | Calculated efficacy according to Colby (%) |
|---|---|---|---|---|
| Dinotefuran Bilobalide | 0.08 400 | — | 0 0 | — — |
| Dinotefuran + Bilobalide | 0.08 400 | 1:5000 | 50 | 0 |
| Alphacypermethrin Bilobalide | 0.08 400 | — | 0 0 | — — |
| Alphacypermethrin + Bilobalide | 0.08 400 | 1:5000 | 50 | 0 |

Test 4

For evaluating control of yellow fever mosquito (*Aedes aegypti*) the test unit consisted of MTPs containing 200 μl water per well and 5-15 freshly hatched *A. aegypti* larvae. The compounds or mixtures were formulated using a solution containing 75% water and 25% DMSO. Different concentrations of formulated compounds or mixtures were sprayed onto the insect diet at 2.5 μl, using a custom built micro atomizer, at two replications. For experimental mixtures in these tests identical volumes of both mixing partners at the desired concentrations respectively, were mixed together. After application, MTPs were incubated at 28±1° C., 80±5% room humidity for 2 days. Larval mortality was then visually assessed. The results were listed in Table 4.

TABLE 4

| Active compound/ active mixture | Concentration (ppm) | Ratio | Observed efficacy (%) | Calculated efficacy according to Colby (%) |
|---|---|---|---|---|
| Thiamethoxam Bilobalide | 0.8 160 | — | 50 0 | — — |
| Thiamethoxam + Bilobalide | 0.08 400 | 1:200 | 100 | 50 |

Test 5

For evaluating control of southern green stink bug (*Nezara viridula*) the compounds or mixtures were formulated using a solution containing acetone and water (50:50) and 0.01% kinetic. Whole Green Beans are rinsed in a 1% bleach solution, triple rinsed with deionised water, and allowed to air dry at least 30 minutes in the fume hood. Beans were dipped in treatment solutions for 5 seconds and allowed to air dry for 30 minutes in the fume hood. For maximum exposure, southern green stink bug (4$^{th}$ instar) were dipped in treatment solution for 3 seconds and allowed to air dry in a cup lined with filter paper and closed with a vented lid for 10 minutes in the fume hood. Three beans were placed in 500 ml deli cups with a 70 mm dry filter paper in the bottom and a 29.5 ml portion cup with a cotton wick for water, and infested with 4 southern green stink bug per cup. Each treatment was replicated 3-fold. Assay arenas were held at 27° C. and 45% room humidity. Data were recorded after 5 days as number of insects alive, with dead recorded as such and all others recorded as alive. The results were listed in Table 5.

TABLE 5

| Active compound/ active mixture | Concentration (ppm) | Ratio | Observed efficacy (%) | Calculated efficacy according to Colby (%) |
|---|---|---|---|---|
| Spinosad | 10 | — | 17 | — |
| Ginkgolide A | 5 | — | 58 | — |
| Spinosad + | 10 | 2:1 | 92 | 65 |
| Ginkgolide A | 5 | | | |
| Pyrethrum | 10 | — | 25 | — |
| Ginkgolide A | 5 | — | 58 | — |
| Pyrethrum + | 10 | 2:1 | 92 | 68.5 |
| Ginkgolide A | 5 | | | |
| Pyraclostrobin | 10 | — | 0 | — |
| Ginkgolide A | 5 | — | 58 | — |
| Pyraclostrobin + | 10 | 2:1 | 67 | 58 |
| Bilobalide | 5 | | | |
| Fluxapyroxad | 10 | — | 0 | — |
| Ginkgolide A | 5 | — | 58 | — |
| Fluxapyroxad + | 10 | 2:1 | 67 | 58 |
| Ginkgloide A | 5 | | | |

Test 6

For evaluating control of different pathogens in a microtest the active compounds were formulated separately as a stock solution having a concentration of 10000 ppm in dimethyl sulfoxide. The percentages were converted into efficacies. An efficacy of 0 means that the growth level of the pathogens corresponds to that of the untreated control; an efficacy of 100 means that the pathogens were not growing.

The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

Test 6-1. Activity Against the Late Blight Pathogen *Phytophthora infestans*

The stock solutions were mixed according to the ratios in Table 6, pipetted onto a MTP and diluted with water to the concentrations in Table 6. A spore suspension of *Phytophthora infestans* containing a pea juice-based aqueous nutrient medium or DDC medium was then added. The plates were placed in a water vapor-saturated chamber at a temperature of 18° C. Using an absorption photometer, the MTPs were measured at 405 nm 7 days after the inoculation. The results were listed in Table 6.

TABLE 6

| Active compound/ active mixture | Concentration (ppm) | Ratio | Observed efficacy (%) | Calculated efficacy according to Colby (%) |
|---|---|---|---|---|
| Mancozeb | 0.063 | — | 39 | — |
| Bilobalide | 1 | — | 24 | — |
| Mancozeb + | 0.063 | 1:16 | 80 | 53 |
| Bilobalide | 1 | | | |
| Mancozeb | 0.016 | — | 15 | — |
| Bilobalide | 0.25 | — | 4 | — |
| Mancozeb + | 0.016 | 1:16 | 54 | 18 |
| Bilobalide | 0.25 | | | |
| Mancozeb | 0.004 | — | 0 | — |
| Bilobalide | 0.063 | — | 0 | — |
| Mancozeb + | 0.016 | 1:16 | 28 | 0 |
| Bilobalide | 0.25 | | | |
| Mancozeb | 0.016 | — | 15 | — |
| Bilobalide | 1 | — | 24 | — |
| Mancozeb + | 0.016 | 1:63 | 62 | 35 |
| Bilobalide | 1 | | | |
| Mancozeb | 0.004 | — | 0 | — |
| Bilobalide | 0.25 | — | 4 | — |
| Mancozeb + | 0.004 | 1:63 | 23 | 4 |
| Bilobalide | 0.25 | | | |
| Ametoctradin | 0.004 | — | 0 | — |
| Bilobalide | 0.25 | — | 4 | — |
| Ametoctradin + | 0.004 | 1:63 | 26 | 4 |
| Bilobalide | 0.25 | | | |
| Carbendazim | 0.004 | — | 0 | — |
| Bilobalide | 0.25 | — | 4 | — |
| Carbendazim + | 0.004 | 1:63 | 29 | 4 |
| Bilobalide | 0.25 | | | |
| Iprodion | 0.004 | — | 0 | — |
| Bilobalide | 0.25 | — | 4 | — |
| Iprodion + | 0.004 | 1:63 | 26 | 4 |
| Bilobalide | 0.25 | | | |
| Prochloraz | 0.016 | — | 3 | — |
| Bilobalide | 0.25 | — | 4 | — |
| Prochloraz + | 0.016 | 1:16 | 26 | 6 |
| Bilobalide | 0.25 | | | |
| Mancozeb | 1 | — | 20 | — |
| Ginkgolide A | 63 | — | 38 | — |
| Mancozeb + | 1 | 1:63 | 97 | 51 |
| Ginkgolide A | 63 | | | |

Test 6-2. Activity Against the Grey Mold *Botrytis cinerea*

The stock solutions were mixed according to the ratios in Table 7, pipetted onto a MTP and diluted with water to the concentrations in Table 7. A spore suspension of *Botrcicinerea* in an aqueous biomalt or yeast-bactopeptone-sodiumacetate solution was then added. The plates were placed in a water vapor-saturated chamber at a temperature of 18° C. Using an absorption photometer, the MTPs were measured at 405 nm 7 days after the inoculation. The results were listed in Table 7.

TABLE 7

| Active compound/ active mixture | Concentration | Ratio | Observed efficacy (%) | Calculated efficacy according to Colby (%) |
|---|---|---|---|---|
| Chlorothalonil | 4 | — | 53 | — |
| Bilobalide | 63 | — | 1 | — |
| Chlorothalonil + | 4 | 1:16 | 95 | 56 |
| Bilobalide | 63 | | | |
| Prochloraz | 4 | — | 39 | — |
| Ginkgolide A | 63 | — | 4 | — |
| Prochloraz + | 4 | 1:16 | 80 | 41 |
| Ginkgolide A | 63 | | | |

Test 6-3. Activity Against Rice Blast *Pyricularia oryzae*

The stock solutions were mixed according to the ratios in Table 8, pipetted onto a MTP and diluted with water to the concentrations in Table 8. A spore suspension of *Pyricularia oryzae* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation. The results were listed in Table 8.

TABLE 8

| Active compound/ active mixture | Concentration | Ratio | Observed efficacy (%) | Calculated efficacy according to Colby (%) |
|---|---|---|---|---|
| Pyraclostrobin | 0.016 | — | 46 | — |
| Bilobalide | 16 | — | 1 | — |
| Pyraclostrobin + Bilobalide | 0.016 16 | 1:1000 | 80 | 46 |
| Pyraclostrobin | 0.016 | — | 46 | — |
| Bilobalide | 4 | — | 3 | — |
| Pyraclostrobin + Bilobalide | 0.016 4 | 1:250 | 73 | 47 |
| Azoxystrobin | 0.25 | — | 45 | — |
| Bilobalide | 63 | — | 5 | — |
| Azoxystrobin + Bilobalide | 0.25 63 | 1:252 | 82 | 48 |
| Azoxystrobin | 0.25 | — | 45 | — |
| Bilobalide | 16 | — | 1 | — |
| Azoxystrobin + Bilobalide | 0.25 16 | 1:64 | 69 | 45 |
| Chlorothalonil | 0.25 | — | 13 | — |
| Bilobalide | 16 | — | 1 | — |
| Chlorothalonil + Bilobalide | 0.25 16 | 1:64 | 99 | 14 |
| Chlorothalonil | 0.25 | — | 13 | — |
| Bilobalide | 4 | — | 3 | — |
| Chlorothalonil + Bilobalide | 0.25 4 | 1:16 | 52 | 16 |
| Trifloxystrobin | 0.063 | — | 24 | — |
| Bilobalide | 63 | — | 5 | — |
| Trifloxystrobin + Bilobalide | 0.063 63 | 1:1000 | 65 | 28 |
| Mancozeb | 1 | — | 11 | — |
| Bilobalide | 63 | — | 5 | — |
| Mancozeb + Bilobalide | 1 63 | 1:63 | 98 | 16 |
| Chlorothalonil | 0.25 | — | 15 | — |
| Ginkgolide A | 4 | — | 0 | — |
| Chlorothalonil + Ginkgolide A | 0.25 4 | 1:16 | 100 | 15 |
| Chlorothalonil | 0.25 | — | 15 | — |
| Ginkgolide A | 16 | — | 0 | — |
| Chlorothalonil + Ginkgolide A | 0.25 16 | 1:64 | 100 | 15 |
| Trifloxystrobin | 0.063 | — | 24 | — |
| Ginkgolide A | 16 | — | 0 | — |
| Chlorothalonil + Ginkgolide A | 0.063 16 | 1:1000 | 55 | 26 |
| Fenhexannid | 1 | — | 40 | — |
| Ginkgolide A | 16 | — | 0 | — |
| Fenhexamid + Ginkgolide A | 1 16 | 1:16 | 64 | 40 |
| Pyrimethalin | 4 | — | 27 | — |
| Ginkgolide A | 63 | — | 3 | — |
| Pyrimethalin + Ginkgolide A | 4 63 | 1:16 | 60 | 29 |

Test 6-4. Activity Against Leaf Blotch on Wheat Caused by *Septoria tritici*

The stock solutions were mixed according to the ratios in Table 9, pipetted onto a MTP and diluted with water to the concentrations in Table 9. A spore suspension of *Septoria tritici* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation. The results were listed in Table 9.

TABLE 9

| Active compound/ active mixture | Concentration | Ratio | Observed efficacy (%) | Calculated efficacy according to Colby (%) |
|---|---|---|---|---|
| Trifloxystrobin | 0.016 | — | 67 | — |
| Bilobalide | 4 | — | 8 | — |
| Trifloxystrobin + Bilobalide | 0.016 4 | 1:250 | 99 | 70 |
| Trifloxystrobin | 0.004 | — | 7 | — |
| Bilobalide | 1 | — | 6 | — |
| Trifloxystrobin + Bilobalide | 0.004 1 | 1:250 | 70 | 13 |
| Pyraclostrobin | 0.004 | — | 59 | — |
| Bilobalide | 1 | — | 6 | — |
| Pyraclostrobin + Bilobalide | 0.004 1 | 1:250 | 90 | 61 |
| Epoxiconazol | 0.25 | — | 35 | — |
| Bilobalide | 16 | — | 9 | — |
| Epoxiconazol + Bilobalide | 0.25 16 | 1:64 | 70 | 40 |
| Prochloraz | 4 | — | 49 | — |
| Ginkgolide A | 63 | — | 16 | — |
| Prochloraz + Ginkgolide A | 4 63 | 1:16 | 83 | 57 |

Test 6-5. Activity Against Early Blight Caused by *Alternaria solani*

The stock solutions were mixed according to the ratios in Table 10, pipetted onto a MTP and diluted with water to the concentrations in Table 10. A spore suspension of *Alternaria solani* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation. The results were listed in Table 10.

TABLE 10

| Active compound/ active mixture | Concentration | Ratio | Observed efficacy (%) | Calculated efficacy according to Colby (%) |
|---|---|---|---|---|
| Fenhexamid | 4 | — | 46 | — |
| Bilobalide | 16 | — | 0 | — |
| Fenhexamide + Bilobalide | 4 16 | 1:4 | 77 | 48 |
| Difenoconazol | 1 | — | 0 | — |
| Bilobalide | 63 | — | 0 | — |
| Difenoconazol + Bilobalide | 1 63 | 1:63 | 34 | 0 |
| Fluoxastrobin | 0.25 | — | 11 | — |
| Ginkgolide A | 63 | — | 0 | — |
| Fluoxastrobin + Ginkgolide A | 0.25 63 | 1:252 | 81 | 11 |
| Epoxiconazol | 0.25 | — | 36 | — |
| Ginkgolide A | 16 | — | 0 | — |
| Epoxiconazol + Ginkgolide A | 0.25 16 | 1:63 | 66 | 36 |
| Picoxystrobin | 0.25 | — | 39 | — |
| Ginkgolide A | 63 | — | 0 | — |
| Picoxystrobin + Ginkgolide A | 0.25 63 | 1:252 | 61 | 39 |

Test 6-6. Activity Against Wheat Leaf Spots Caused by *Leptosphaeria nodorum*

The stock solutions were mixed according to the ratios in Table 11, pipetted onto a MTP and diluted with water to the concentrations in Table 11. A spore suspension of *Leptosphaeria nodorum* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation. The results were listed in Table 11.

TABLE 11

| Active compound/ active mixture | Concentration | Ratio | Observed efficacy (%) | Calculated efficacy according to Colby (%) |
|---|---|---|---|---|
| Chlorothalonil | 1 | — | 39 | — |
| Ginkgolide A | 63 | — | 18 | — |
| Chlorothalonil + Ginkgolide A | 1 63 | 1:63 | 70 | 50 |
| Difenoconazol | 1 | — | 21 | — |
| Bilobalide | 63 | — | 24 | — |
| Difenoconazol + Bilobalide | 1 63 | 1:63 | 76 | 40 |

Test 7

Compatibility of bilobalide with *Beauveria bassiana* strain PPRI 5339 was analyzed. Aqueous mixtures containing 100 ppm of bilobalide, and 4×10E 7 CFU/ml of *Beauveria bassiana* strain PPRI 5339 were filled in bottles. Bottles were shaken to ascertain complete dilution and incubated at room temperature (26° C.). The aqueous mixtures were maintained for 1 hour, or 24 hours. Ten-fold serial dilutions were made for both incubation times from 1:10E 0 to 1:10E 10. A fixed volume (100 µl) of each dilution was distributed aseptically onto petri dishes containing Dichloran-Rose-Bengal-Chlortetracycline agar for culture. Petri dishes were incubated in a dark chamber at 28° C. for five days and submitted to visual inspection. Analyzed parameters were the number of colonies, colony diameter, shape, color, and speed of growth. The results showed that *Beauveria bassiana* strain PPRI 5339 and Bilobalide were compatible under all tested conditions.

For evaluating control of southern green stink bug (*Nezara viridula*), Bilobalide, *Beauveria bassiana* strain PPRI 5339, or mixtures thereof were formulated using a solution containing water and acetone (98.75:1.25). *Beauveria bassiana* strain PPRI 5339 was at room temperature for one hour before use.

Seven days old Lima bean plants were dipped into each treatment. Once dried, plants were artificially infested with four second instar southern green stink bugs. Percentage of mortality (sick+ death insects) was evaluated at 5 days. The results were listed in Table 12.

TABLE 12

| Active compound/ active mixture | Concentration | Ratio | Observed efficacy (%) | Calculated efficacy according to Colby (%) |
|---|---|---|---|---|
| *Beauveria bassiana* strain PPRI 5339 | 4 × 10E7 CFU/ml | — | 37 | — |
| Bilobalide | 50 ppm | — | 33 | — |
| *Beauveria bassiana* strain PPRI 5339 + Bilobalide | 4 × 10E7 CFU/ml 50 ppm | 2 × 10E5 CFU/ml:1 ppm | 100 | 58 |

The invention claimed is:

1. A pesticidal mixture comprising as active compounds
   1) at least one compound (I), which is a component of the ginkgo tree selected from the group consisting of bilobalide, ginkgolide A, ginkgolide B, ginkgolide C, ginkgolide J and ginkgolide M,
   and
   2) alpha-cypermethrin;
   in a synergistically effective amount, wherein the weight ratio of compound I and alpha-cypermethrin is from 5000:1 to 1:5.

2. The pesticidal mixture of claim 1, wherein the weight ratio of compound I and alpha-cypermethrin is from 1000:1 to 1:2.

3. A pesticidal composition comprising a liquid or solid carrier and the mixture of claim 1.

4. A seed treated with the mixture of claim 1 in an amount of from 0.1 g to 100 kg per 100 kg of seeds.

5. A seed treated with the mixture of claim 2 in an amount of from 0.1 g to 100 kg per 100 kg of seeds.

6. A method for controlling pests from the family of Pentatomidae, comprising the step of contacting the pests, their food supply, habitat or breeding grounds with the pesticidal mixture of claim 1.

7. A method for controlling pests from the family of Pentatomidae, comprising the step of contacting the pests, their food supply, habitat or breeding grounds with the pesticidal mixture of claim 2.

* * * * *